US010624964B2

(12) United States Patent
Lopez

(10) Patent No.: US 10,624,964 B2
(45) Date of Patent: Apr. 21, 2020

(54) METHODS AND COMPOSITIONS FOR STIMULATING IMMUNE RESPONSE USING POTENT IMMUNOSTIMULATORY RNA MOTIFS

(71) Applicant: THE TRUSTEES OF THE UNIVERSITY OF PENNSYLVANIA, Philadelphia, PA (US)

(72) Inventor: Carolina B. Lopez, Wynnewood, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 86 days.

(21) Appl. No.: 15/571,096

(22) PCT Filed: Apr. 29, 2016

(86) PCT No.: PCT/US2016/030242
§ 371 (c)(1),
(2) Date: Nov. 1, 2017

(87) PCT Pub. No.: WO2016/179034
PCT Pub. Date: Nov. 10, 2016

(65) Prior Publication Data
US 2018/0169222 A1 Jun. 21, 2018

Related U.S. Application Data
(60) Provisional application No. 62/155,740, filed on May 1, 2015.

(51) Int. Cl.
| | | |
|---|---|---|
| *A61K 39/39* | (2006.01) | |
| *C07H 21/02* | (2006.01) | |
| *A61K 39/12* | (2006.01) | |
| *A61P 35/00* | (2006.01) | |
| *C12N 15/117* | (2010.01) | |
| *A61P 31/14* | (2006.01) | |
| *A61K 39/00* | (2006.01) | |

(52) U.S. Cl.
CPC ............ *A61K 39/39* (2013.01); *A61K 39/12* (2013.01); *A61P 31/14* (2018.01); *A61P 35/00* (2018.01); *C07H 21/02* (2013.01); *C12N 15/117* (2013.01); *A61K 2039/53* (2013.01); *A61K 2039/55511* (2013.01); *A61K 2039/55561* (2013.01); *C12N 2310/17* (2013.01); *C12N 2320/31* (2013.01); *C12N 2760/18821* (2013.01)

(58) Field of Classification Search
None
See application file for complete search history.

(56) References Cited

U.S. PATENT DOCUMENTS

| | | | |
|---|---|---|---|
| 5,593,972 A | 1/1997 | Weiner et al. | |
| 5,703,055 A | 12/1997 | Felgner et al. | |
| 5,739,118 A | 4/1998 | Carrano et al. | |
| 5,837,533 A | 11/1998 | Boutin | |
| 2009/0304738 A1* | 12/2009 | Moran ............... | A61K 39/39 424/205.1 |
| 2010/0311171 A1 | 12/2010 | Nakanishi et al. | |
| 2012/0039916 A1 | 2/2012 | Zurawski et al. | |

FOREIGN PATENT DOCUMENTS

| | | |
|---|---|---|
| WO | WO 90/14837 A1 | 12/1990 |
| WO | WO 92/19265 A1 | 11/1992 |
| WO | WO 93/13202 A1 | 7/1993 |
| WO | WO 94/16737 A1 | 8/1994 |
| WO | WO 96/10038 A1 | 4/1996 |
| WO | WO 2014/151265 A1 | 9/2014 |

OTHER PUBLICATIONS

Accession No. AB855654.1, submitted on Sep. 21, 2013.*
AC146623, GenBank Accession No. AC146623, Otolemur gamettii clone CH256-392L9, Working Draft Sequence, 3 ordered pieces, Oct. 23, 2003 [online]. Retrieved on Apr. 20, 2018] <URL https://www.ncbi.nlm.nih.gov/nuccore/AC146623>.
AC150456, GenBank Accession No. AC150456, Callithrix jacchus clone CH259-272E24, Working Draft Sequence, 5 ordered pieces, Aug. 10, 2004 [online]. [Retrieved on Apr. 20, 2018] <URL https://www.ncbi.nlm.nih.gov/nuccore/AC150456>.
Alving et al., "Adjuvants for human vaccines," Curr Opin Immunol 24:310-315 (2012).
Anchisi et al., "RIG-I ATPase Activity and Discrimination of Self-RNA versus Non-Self-RNA," mBio 6(2):e02349-14 (2015).
Avery's Drug Treatment: Principles and Practice of Clinical Pharmacology and Therapeutics, 3rd edition, ADIS Press, LTD., Williams and Wilkins, Baltimore, Md. (1987) (Table of Contents).
Bal et al., "Advances in transcutaneous vaccine delivery: Do all ways lead to Rome?" J. Control Release 148:266-282 (2010).
Baldwin et al., "The importance of adjuvant formulation in the development of a TB vaccine," J. Immunol 188(5):2189-2197 (2012).
Berkow et al., eds., The Merck Manual, 15th edition, Merck and Co., Rahway, N.J. (1987) (Table of Contents).
Berkow et al., eds., The Merck Manual, 16th edition, Merck and Co., Rahway, N.J., 1992 (Table of Contents).
Bunka et al., "Aptamers come of age—at last," Nature Reviews Microbiology 4:588-596 (2006).
Calain et al., "Molecular Cloning of Natural Paramyxovirus Copy-Back Defective Interfering RNAs and Their Expression from DNA," Virology 191:62-71 (1992).

(Continued)

*Primary Examiner* — Agnieszka Boesen
(74) *Attorney, Agent, or Firm* — Baker Botts, LLP

(57) ABSTRACT

The presently disclosed subject matter relates to methods and compositions relating to immunostimulatory RNA motifs that act as adjuvants and/or immunostimulatory agents to enhance host immune responses.

8 Claims, 53 Drawing Sheets

Specification includes a Sequence Listing.

(56) References Cited

OTHER PUBLICATIONS

Caskey et al., "Synthetic double-stranded RNA induces innate immune responses similar to a live viral vaccine in humans," J Exp. Med 208(12):2357-2366 (2011).
Clegg et al., "Adjuvant solution for pandemic influenza vaccine production," PNAS USA 109(43):17585-17590 (2012).
Deutsch et al., "Nongenetic Complementation in VSV: Asymmetric Contribution of the L Proteins of Each Parent in the Rescue of Group I TS Mutants," Virology 124:366-379 (1983).
Dixit et al., "Intracellular pathogen detection by RIG-I-like Receptors," Advances in Immunology 117:99-125 (2013).
Dranoff et al., "Vaccination with irradiated tumor cells engineered to secrete murine granulocyte-macrophage colony-stimulating factor stimulates potent, specific, and long-lasting anti-tumor immunity," PNAS USA 90:3539-3543 (1993).
Ebadi, Pharmacology, Little, Brown and Co., Boston, Mass. (1985) (Table of Contents).
Engelhorn et al., "Molecular cloning and characterization of a Sendai virus internal deletion defective RNA," J Gen Virol 74:137-141 (1993).
Foon, K., "Vaccine Therapies for Epithelial Cancers," 2000, ASCO Educational Book Spring: pp. 730-738.
Goodman et al., eds., Goodman and Gilman's The Pharmacological Basis of Therapeutics, 8th edition, Pergamon Press, Inc., Elmsford, N.Y. (1990) (Table of Contents).
Gosai et al., "Global Analysis of the RNA-Protein Interaction and RNA Secondary Structure Landscapes of the *Arabidopsis* Nucleus," Mol. Cell 57:376-388 (2015).
Goubau et al., "Antiviral immunity via RIG-I-mediated recognition of RNA bearing 5'-diphosphates," Nature 514:372-375 (2014).
HE605209, GenBank Accession No. HE605209, Candida parapsilosis strain CDC317 annotated contig 006110, Oct. 26, 2011 [online]. [Retrieved on Apr. 20, 2018] <URL https://www.ncbi.nlm.nih.gov/nuccore/HE605209>.
Hermesh et al., "Buying Time—The Immune System Determinants of the Incubation Period to Respiratory Viruses," Viruses 2:2541-2558 (2010).
International Search Report dated Nov. 7, 2016 in International Application No. PCT/US16/30242.
Kato et al., "Differential roles of MDA5 and RIG-I helicases in the recognition of RNA viruses," Nature 441:101-105 (2006).
Katzung, ed. Basic and Clinical Pharmacology, Fifth Edition, Appleton and Lange, Norwalk, Conn. (1992) (Table of Contents).
Kawai et al., "IPS-1, an adaptor triggering RIG-I- and Mda5-mediated type I interferon induction," Nat Immunol 6(10):981-988 (2005).
Khayat et al., "Overview of Medical Treatments of Metastatic Malignant Melanoma," 2000, ASCO Educational Book Spring: pp. 414-427.
Kim et al., "Specific Association of Human Telomerase Activity with Immortal Cells and Cancer," Science 266:2011-2015 (1994).
Kolakofsky, "Isolation and Characterization of Sendai Virus DI-RNAs," Cell 8:547-555 (1976).
Kumar et al., "Pathogen Recognition by the Innate Immune System," International Reviews of Immunology 30:16-34 (2011).
Kwon et al., "Elimination of residual metastatic prostate cancer after surgery and adjunctive cytotoxic T lymphocyte-associated antigen 4 (CTLA-4) blockade immunotherapy," PNAS USA 96(26):15074-15079 (1999).
Lake et al., "A Better Way for a Cancer Cell to Die," New Engl J of Med 354(23):2503-2504 (2006).
Logothetis, C., "Developmental Therapy for Regionally Advanced Prostate Carcinoma," 2000 ASCO Educational Book Spring: pp. 300-302.
Lopez, "Defective Viral Genomes: Critical Danger Signals of Viral Infections," Journal of Virology 88(16):8720-8723 (2014).
Majumder et al., "Aptamers: from bench side research towards patented molecules with therapeutic applications," Expert Opin. Ther. Patents 19(11):1603-1613 (2009).
Mercado-Lopez et al., "Highly immunostimulatory RNA derived from a Sendai virus defective viral genome," Vaccine 31:5713-5721 (2013).
Moltedo et al., "Cutting edge: Stealth Influenza Virus Replication Precedes the Initiation of Adaptive Immunity," J Immunol 183:3569-3573 (2009).
Nallagatla et al., "5'-Triphosphate-Dependent Activation of PKR by RNAs with Short Stem-Loops," Science 318:1455-1458 (2007).
Nordly et al., "Immunity by formulation design: Induction of high CD8+ T-cell responses by poly(I:C) incorporated into the CAF01 adjuvant via a double emulsion method," J Controlled Release 150:307-317 (2011).
Patel et al., "ATPase-driven oligomerization of RIG-I on RNA allows optimal activation of type-I interferon," EMBO Reports 14:780-787 (2013).
Pavot et al., New insights in mucosal vaccine development, Vaccine 30:142-154 (2012).
Peisley et al., "Cooperative assembly and dynamic disassembly of MDA5 filaments for viral dsRNA recognition," PNAS USA 108(52):21010-21015 (2011).
Peisley et al., "RIG-I Forms Signaling-Competent Filaments in an ATP-Dependent, Ubiquitin-Independent Manner," Mol. Cell 51:573-583 (2013).
Peluso et al., "Initiation and replication of vesicular stomatitis virus genome RNA in a cell-free system," PNAS USA 80:3198-3202 (1983).
Petsch et al., "Protective efficacy of in vitro synthesized, specific mRNA vaccines against influenza A virus infection," Nat Biotechnol 30(12):1210-1216 (2012).
Pichlmair et al., "Activation of MDA5 Requires Higher-Order RNA Structures Generated during Virus Infection," Journal of Virology 83(20):10761-10769 (2009).
Pichlmair et al., "RIG-I-Mediated Antiviral Responses to Single-Stranded RNA Bearing 5'-Phosphates," Science 314:997-1001 (2006).
Plattet et al., "Sendai virus RNA polymerase scanning for mRNA start sites at gene junctions," Virology 362:411-420 (2007).
Raj et al., "Imaging individual mRNA molecules using multiple singly labeled probes," Nat Meth 5(10):877-879 (2008).
Re et al., "Genomic and Copy-Back 3' Termini in Sendai Virus Defective Interfering RNA Species," Journal of Virology 45(2):659-664 (1983).
Restifo et al., "Cancer Vaccines," Cancer: Principles and Practice of Oncology, Fifth Edition, 61:3023-3043 (1997).
Rosenberg et al., "A New Era for Cancer Immunotherapy Based on the Genes that Encode Cancer Antigens," Immunity 10:281-287 (1999).
Rosenberg, S., 2000, "Development of Cancer Vaccines," ASCO Educational Book Spring: pp. 60-62.
Saito et al., "Innate immunity induced by composition-dependent RIG-1 recognition of hepatitis C virus RNA," Nature 454:523-527 (2008).
Salinas et al., "Replication and packaging properties of short Paramyxovirus defective RNAs," Virus Research 109:125-132 (2005).
Samuel, "Antiviral actions of interferons," Clinical Microbiology Reviews 14(4):778-809 (2001).
Schlee et al., "Recognition of 5' Triphosphate by RIG-I Helicase Requires Short Blunt Double-Stranded RNA as Contained in Panhandle of Negative-Strand Virus," Immunity 31:25-34 (2009).
Schneider-Ohrum et al., "Adjuvants that stimulate TLR3 or NLPR3 pathways enhance the efficiency of influenza virus-like particle vaccines in aged mice," Vaccine 29:9081-9092 (2011).
Schnell et al., "Uridine Composition of the Poly-U/UC Tract of HCV RNA Defines Non-Self Recognition by RIG-I," PLoS Pathog 8(8):e1002839 (2012).
Schönborn et al., "Monoclonal antibodies to double-stranded RNA as probes of RNA structure in crude nucleic acid extracts," Nucleic Acids Res 19(11):2993-3000 (1991).
Seo et al., "Obesity-dependent changes in interstitial ECM mechanics promote breast tumorigenesis," Science Trans Med 7(301):301ra130, 13 pages (2015).
Seth et al., "Identification and Characterization of MAVS, a Mitochondrial Antiviral Signaling Protein that Activates NF-κb and IRF3," Cell 122:669-682 (2005).

(56) References Cited

OTHER PUBLICATIONS

Shioda et al., "Determination of the complete nucleotide sequence of the Sendai virus genome RNA and the predicted amino acid sequences of the F, HN and L proteins," Nucleic Acids Res 14(4):1545-1563 (1986).
Strähle et al., "Activation of the Beta Interferon Promoter by Unnatural Sendai Virus Infection Requires RIG-I and Is Inhibited by Viral C Proteins," J Virology 81(22):12227-12237 (2007).
Strähle et al., "Sendai virus defective-interfering genomes and the activation of interferon-beta," Virology 351:101-111 (2006).
Suto et al., "A Mechanism for the Specific Immunogenicity of Heat Shock Protein-Chaperoned Peptides," Science 269:1585-1588 (1995).
Tamura et al., "Immunotherapy of Tumors with Autologous Tumor-Derived Heat Shock Protein Preparations," Science 278:117-120 (1997).
Tapia et al., "Defective Viral Genomes Arising in vivo Provide Critical Danger Signals for the Triggering of Lung Antiviral Immunity," PLoS Pathog 9(10):e1003703 (2013).
Thim et al., "Immunoprotective activity of a Salmonid Alphavirus Vaccine: Comparison of the immune responses induced by inactivated whole virus antigen formulations based on CpG class B oligonucleotides and poly I:C alone or combined with an oil adjuvant," Vaccine 30:4828-4834 (2012).
Uzri et al., "Nucleotide Sequences and Modifications That Determine RIG-I/RNA Binding and Signaling Activities," J Virology 83(9):4174-4184 (2009).
Weber et al., "Double-Stranded RNA is Produced by Positive-Strand RNA Viruses and DNA Viruses but not in Detectable Amounts by Negative-Strand RNA Viruses," J Virology 80(10):5059-5064 (2006).
Witteveldt et al., "The influence of viral RNA secondary structure on interactions with innate host cell defences," Nucleic Acids Research 42(5):3314-3329 (2014).
Wu et al., "Molecular Imprinting as a Signal-Activation Mechanism of the Viral RNA Sensor RIG-I," Molecular Cell 55:511-523 (2014).
Wu et al., "Structural Basis for dsRNA Recognition, Filament Formation, and Antiviral Signal Activation by MDA5," Cell 152:276-289 (2013).
Xu et al., "VISA Is an Adapter Protein Required for Virus-Triggered IFN-β Signaling," Mol. Cell 19:727-740 (2005).
Yoneyama et al., "Viral RNA detection by RIG-I-like receptors," Curr Opin Immunol 32:48-53 (2015).
Yoo et al., "Sensing viral invasion by RIG-I like receptors," Current Opinion in Microbiology 20:131-138 (2014).
Yount et al, "MDA5 Participates in the Detection of Paramyxovirus Infection and is Essential for the Early Activation of Dendritic Cells in Response to Sendai Virus Defective Interfering Particles," J Immunol 180:4910-4918 (2008).
Yount et al., "A Novel Role for Viral-Defective Interfering Particles in Enhancing Dendritic Cell Maturation," J Immunol 177:4503-4513 (2006).
Zavada et al., "Human Cell Surface Proteins Selectively Assembled into Vesicular Stomatitis Virus Virions," Virology 127:345-360 (1983).
Zhao et al., "Antagonism of the interferon-induced OAS-RNase L pathway by murine coronavirus ns2 protein is required for virus replication and liver pathology," Cell Host Microbe 11(6):607-616 (2012).
Zink, "Immunizing Agents and Diagnostic Antigens," Chapter 73 in Pharmaceutical Sciences (1980), pp. 1324-1341.

\* cited by examiner

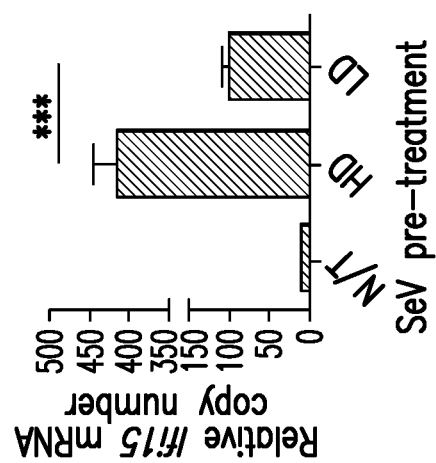
FIG. 1B
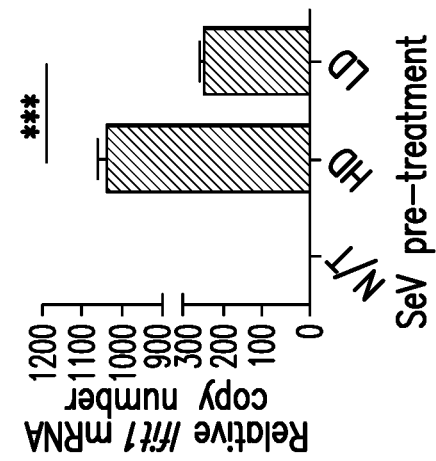
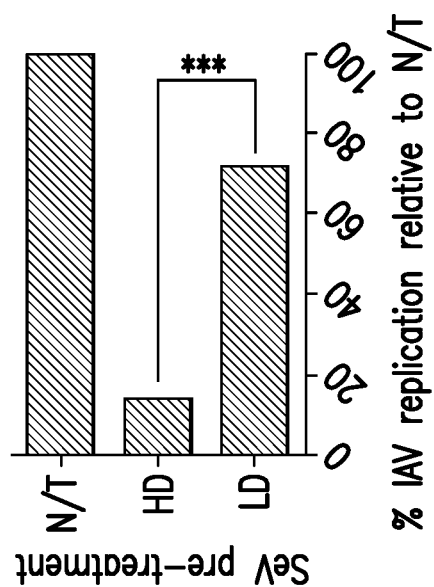
FIG. 1A

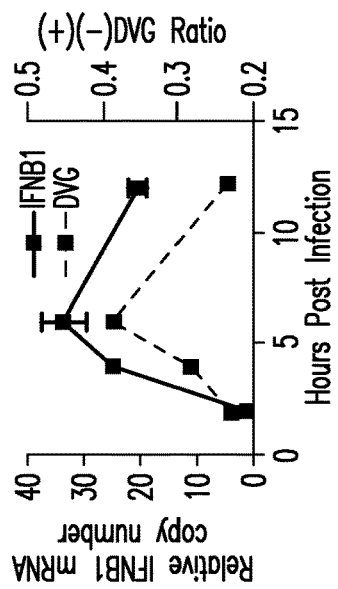
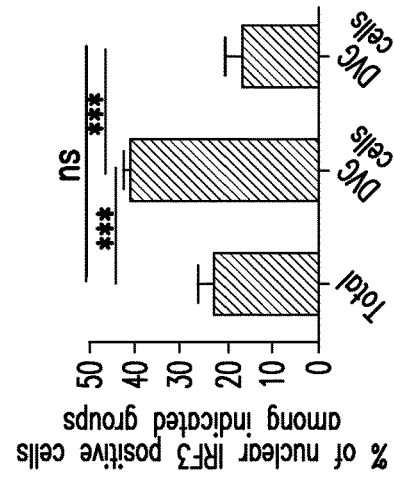
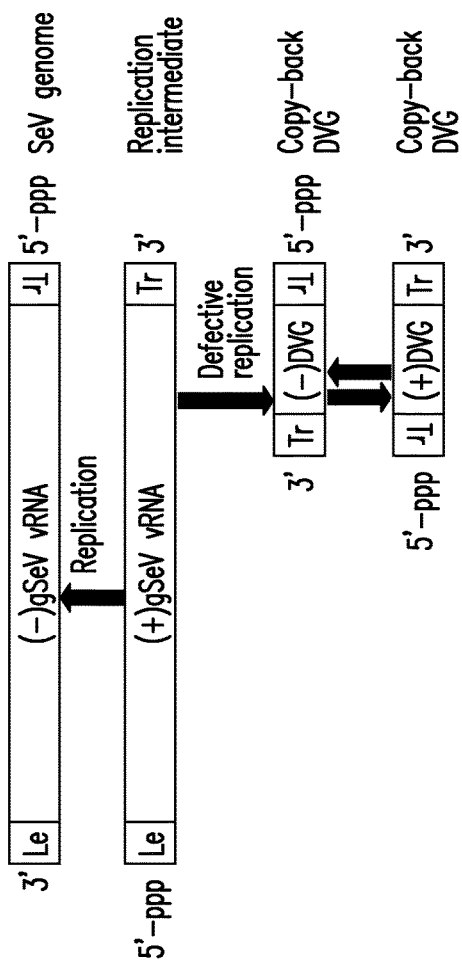
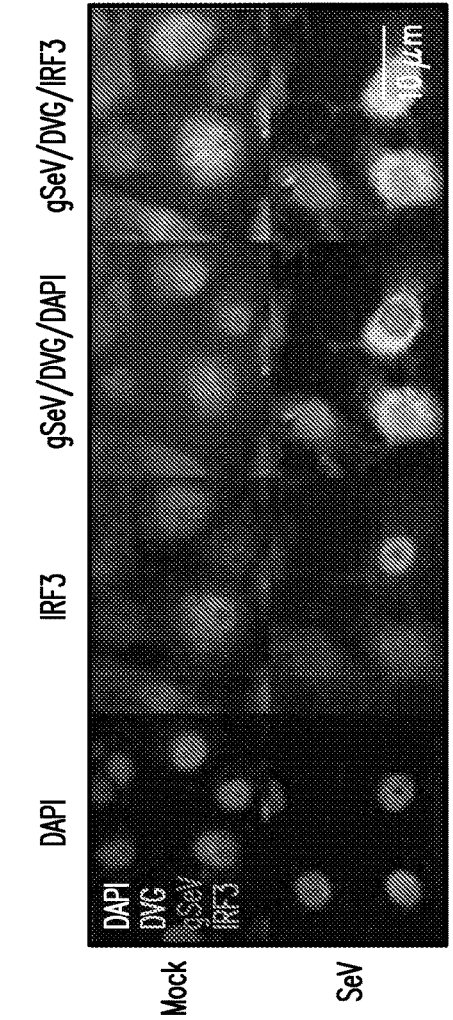
FIG. 2A
FIG. 2B
FIG. 2C
FIG. 2D

DVG-546

DVG-354

DVG-268

C97G

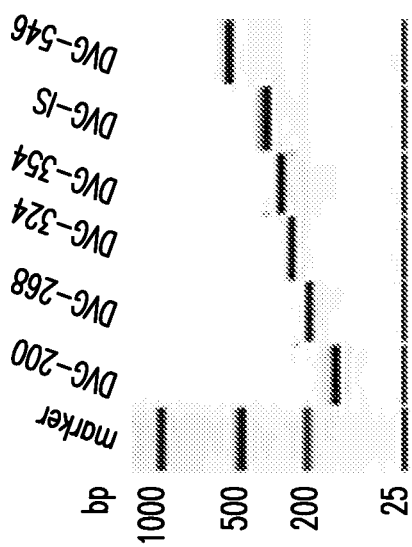
FIG. 5A
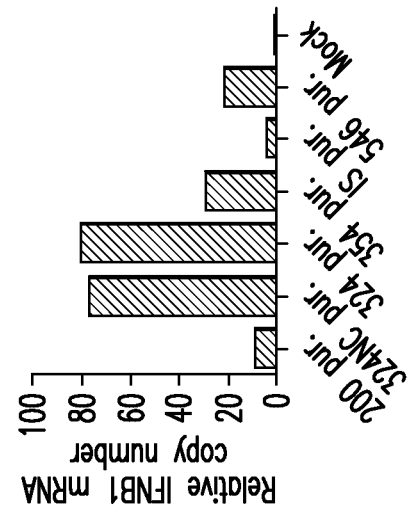
FIG. 5C
| DVG-RNA | Endotoxin concentration (EU/100µg)* |
|---|---|
| DVG-268 | <=1.2 |
| DVG-324 | <=1.2 |
| DVG-324NC | 0.12–1.2 |
| DVG-354 | <=1.2 |
| DVG-546 | 0.12–1.2 |
| DVG-200 | <=1.2 |
| DVG-IS | <=1.2 |
FIG. 5B

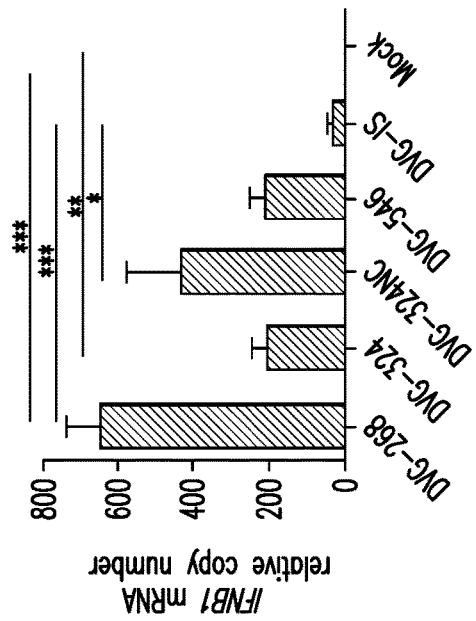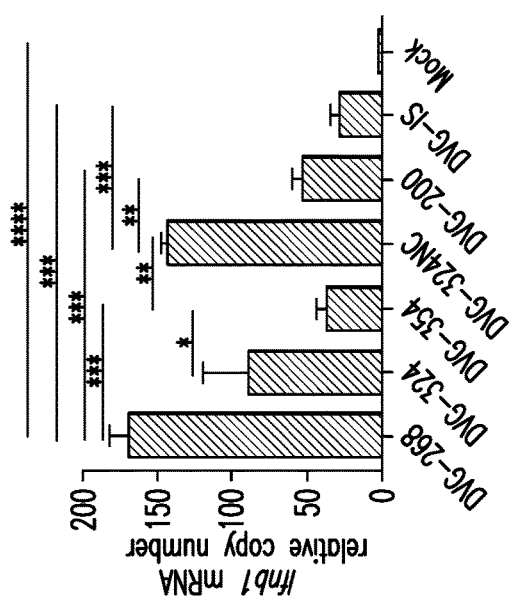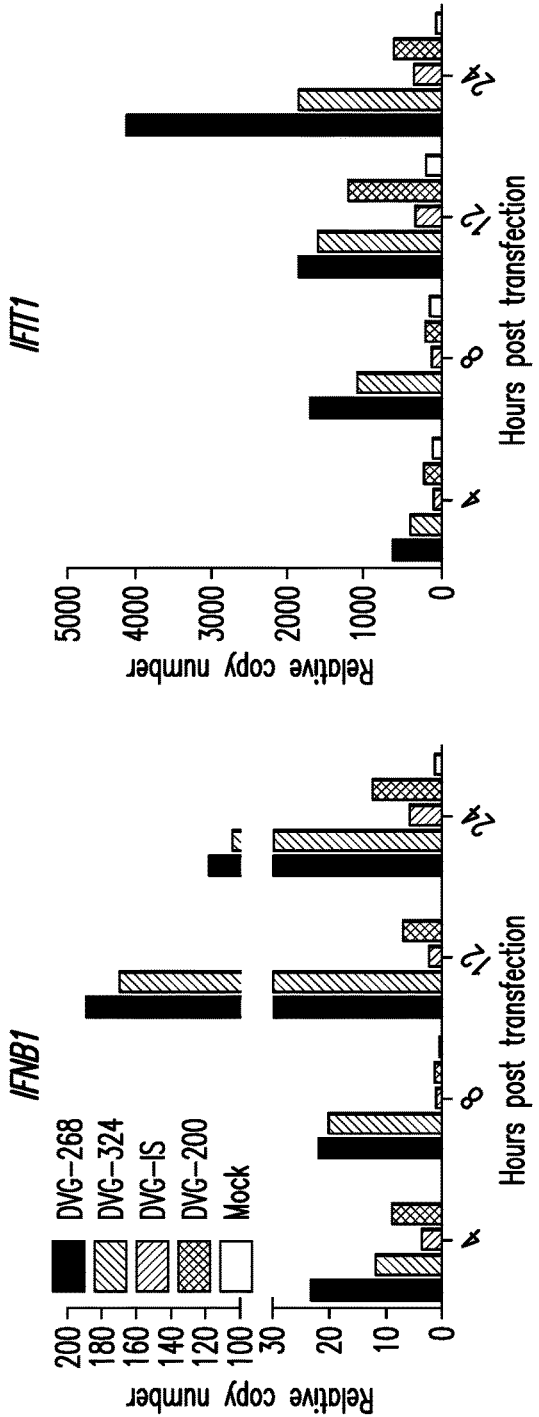
FIG. 6A
FIG. 6B
FIG. 6C

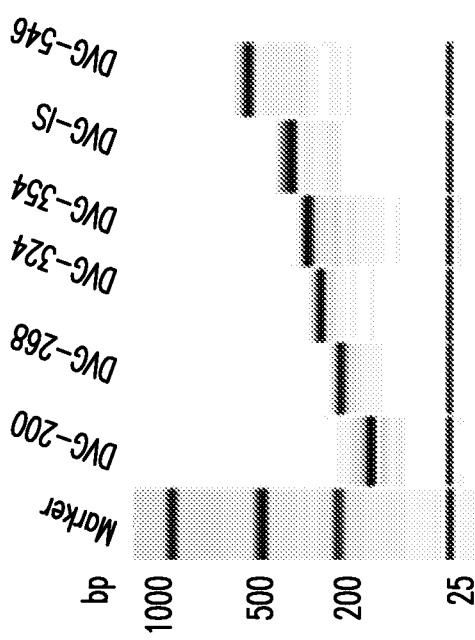
FIG. 7A
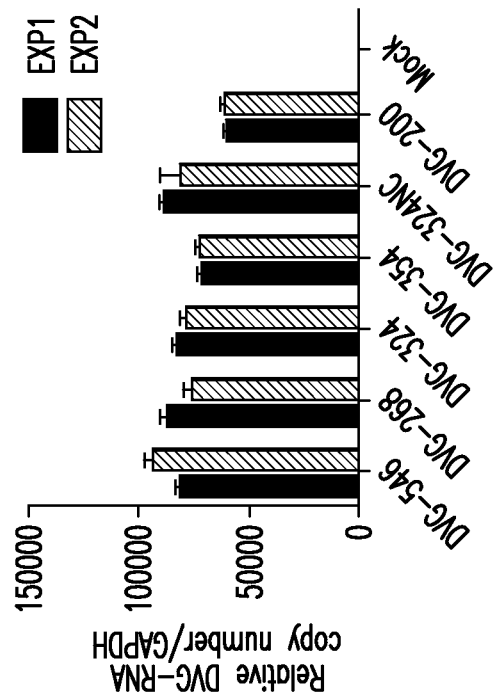
FIG. 7B
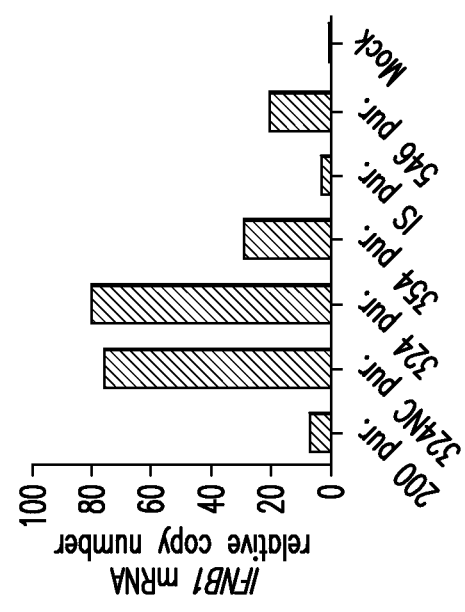
FIG. 7C
FIG. 7D

DVG-546

DVG-546$_\Delta$70-114

DVG-546

DVG-546 motif 1+

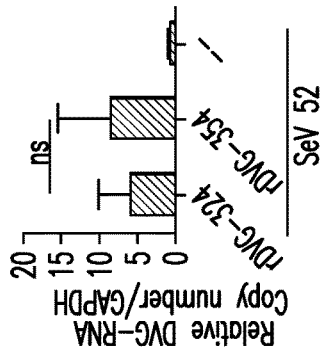
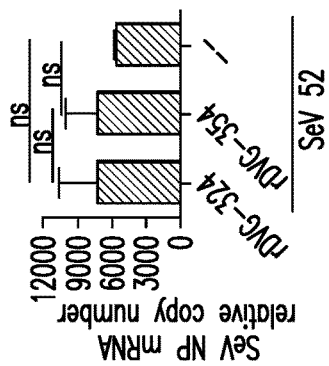
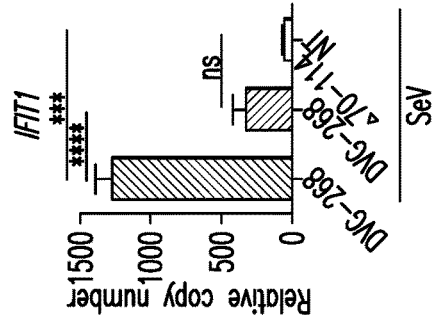
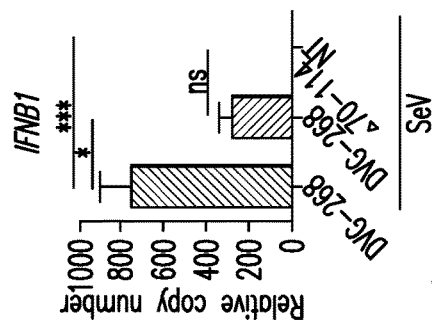
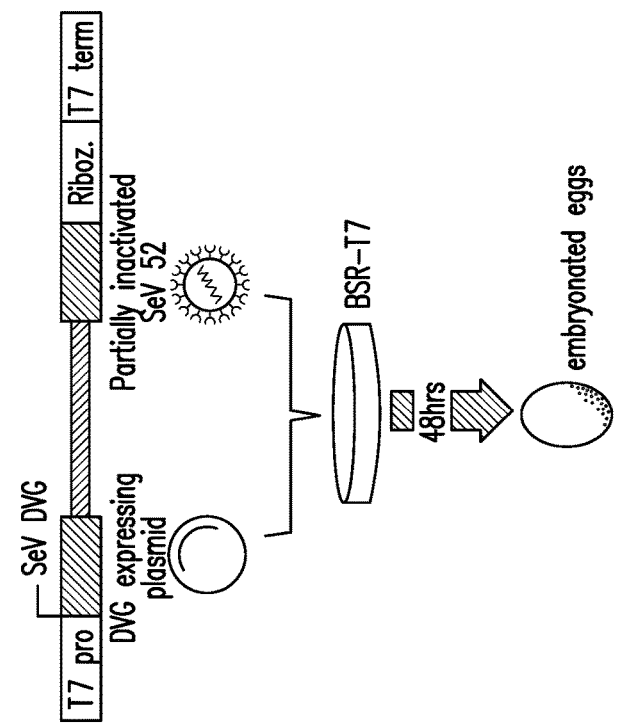
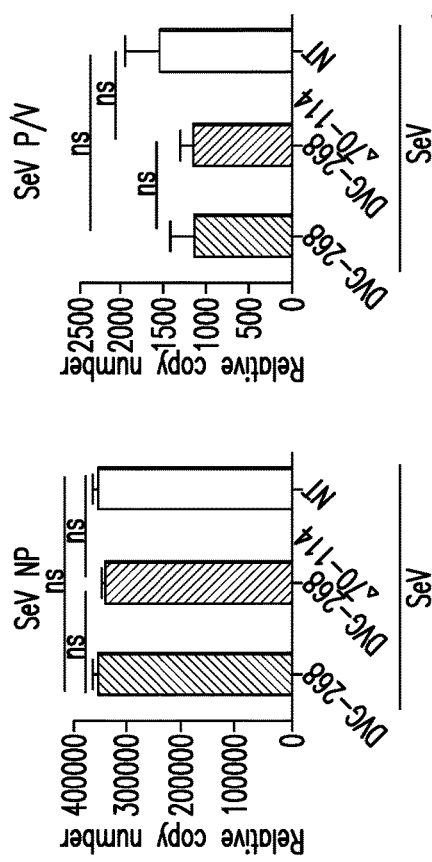
FIG. 9A
FIG. 9B
FIG. 9C

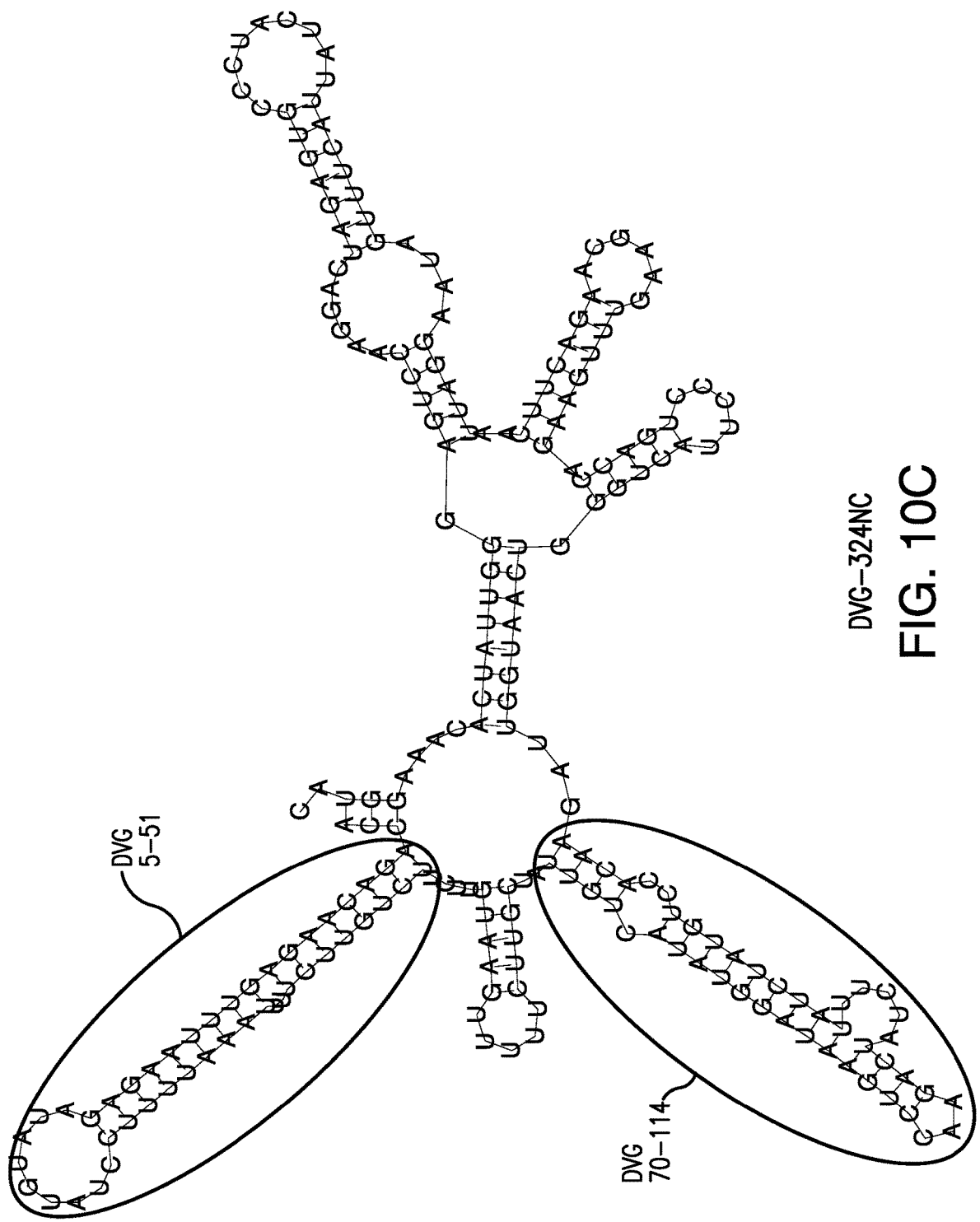

PLUS DVG70-114
(full length:143nt)

PLUS DVG5-51
(full length:144nt)

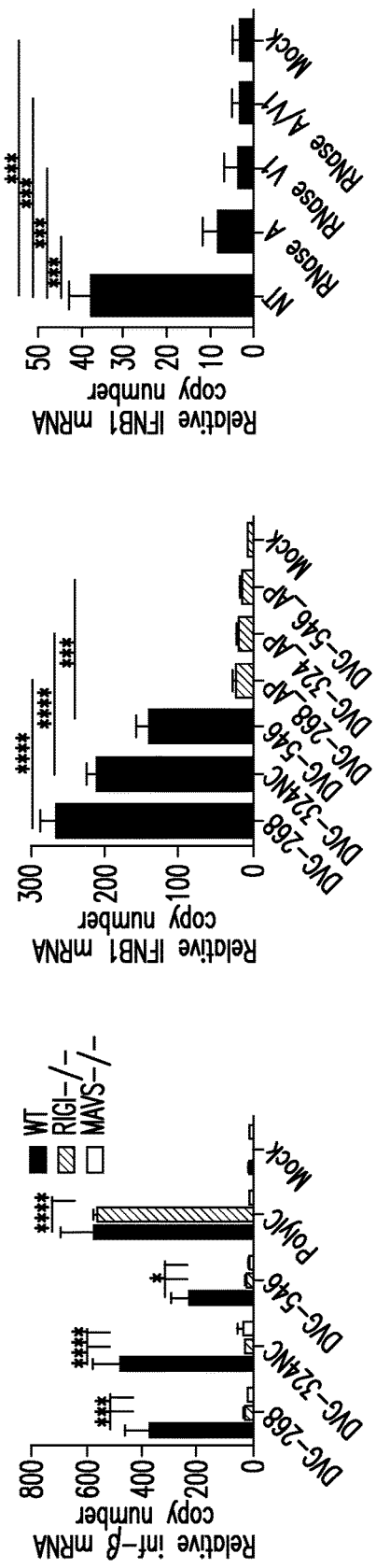
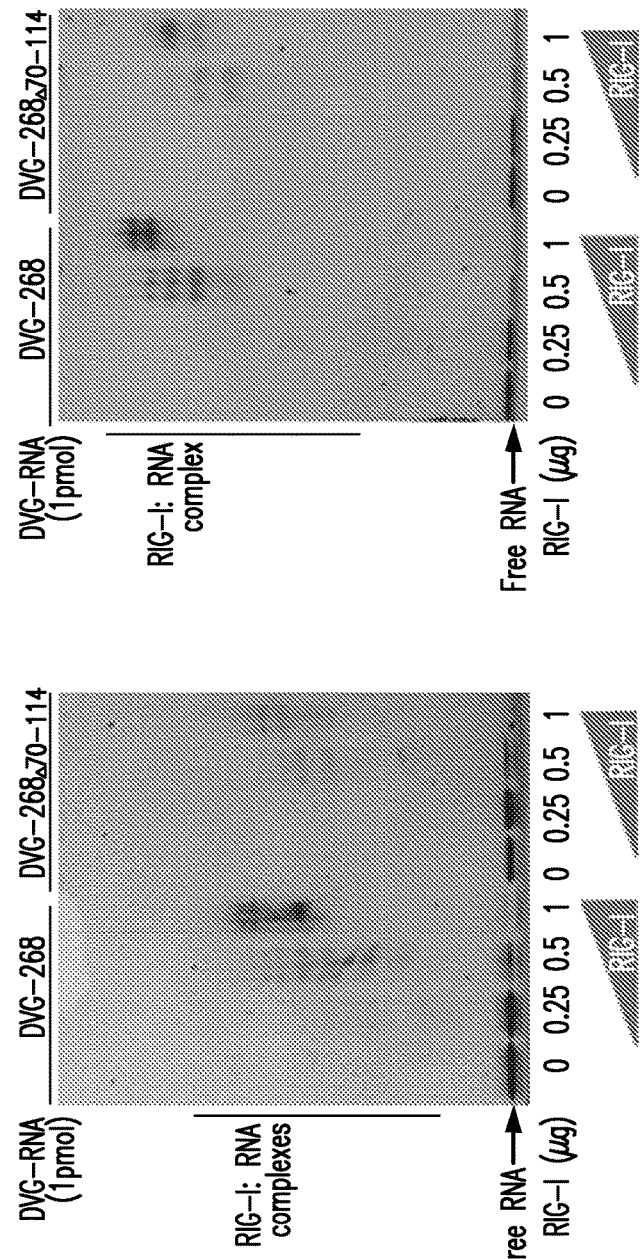
FIG. 13A, FIG. 13B, FIG. 13C, FIG. 13D, FIG. 13E

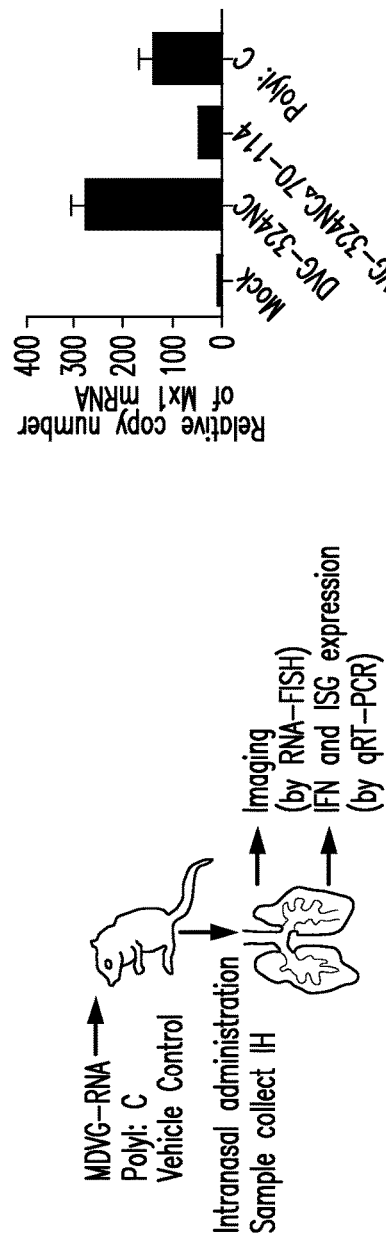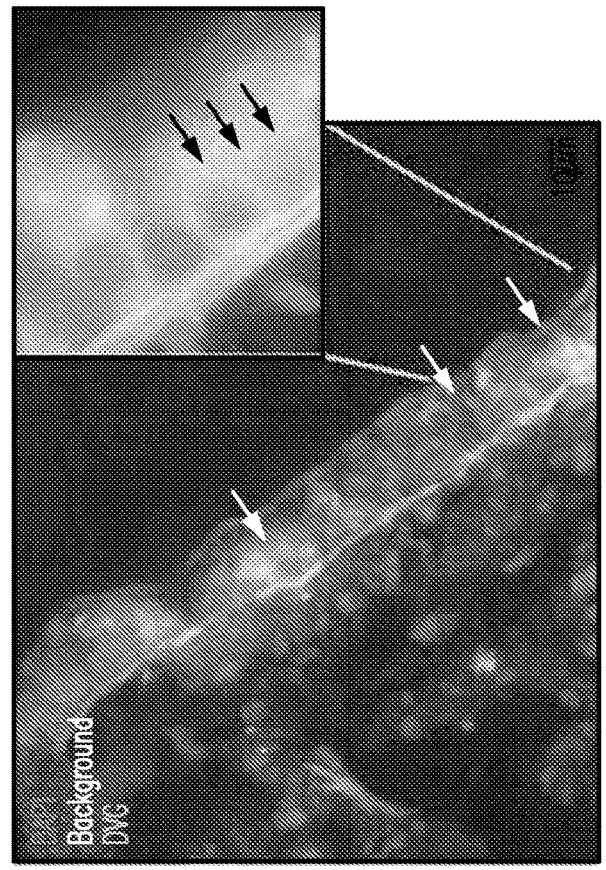
FIG. 15A
FIG. 15B
FIG. 15C

SEQ ID NO:1 DVG$_{70-114}$ Motif (45nt, from 5' to 3')
UUGUCAUAUGGAUAAGUCCAAGACUAUCUUUAUCUAUGUCCACAA

FIG. 16

Stabilizing mutations:
SEQ ID NO:2 DVG$_{70-114}$ Motif1+ (47nt, from 5' to 3')
UUGUCAUAU<u>A</u>GGAUAAGUCCAAGACUAUCUUUAUCU<u>U</u>AUGUCCACAA

FIG. 17

SEQ ID NO:3 DVG$_{70-114}$ U106G (45nt, from 5'-3')
UUGUCAUAUGGAUAAGUCCAAGACUAUCUUUAUCUA<u>G</u>GUCCACAA

FIG. 18

SEQ ID NO:4 DVG$_{70-114}$ C97G (45nt, from 5'-3')
UUGUCAUAUGGAUAAGUCCAAGACUAU<u>G</u>UUUAUCUAUGUCCACAA

FIG. 19

SEQ ID NO:5 DVG70-114 A89U (45nt, from 5' to 3')
UUGUCAUAUGGAUAAGUCCUAGACUAUCUUUAUCUAUGUCCACAA

FIG. 20

| Primers | Forward/reverse primers (5' to 3') |
|---|---|
| 47-114 | GTTCTTGTATAAGTTTTCTCTAGATTGGTAACTGGGTCATTCC |
| 45-51 | GGGAATGACCCAGTTACCAATTCTAGATAAAACTTACAAGAAC |
| T106G | CGAATCACTATAGGAGACATGTAAGTTTTTTCTTATGTC |
| | GACATAAGAAAAACTTACATGTCCTATAGTGATTCG |
| T106G_A77C | GACAATACCAAGAAGAACTTACATCGTCCTATAGTGACTG |
| | CAGTCACTATAGGACGATGTAAGTTCTTCTTGGTATTGTC |
| A89T | GTTTTTCTTTCTATTGTCATCGATAAGTCCAAGACTATC |
| | GATAGTCTTGGACTTATCGATGACAATAGAAAGAAAAAC |
| C97G | GCTATTGTCATAGTCGAATAAGTCCTAGACTATCTTATCTATGTCCAC |
| | GTGGACATAGATAAGATAGTCTAGGACTTATTCGACTATGACAATAGC |
| Met0+ | GGATAAGTCCAAGACTATCTTATCTATGTCGACATAGATAAGTCCAC |
| | CCAATCTGTGGACTTATCTATGTCGACATAGATAAGATAGTCTTGGACTTATCC |
| Met0- | GCTATTGTCATAGATAAGATAGTCCAAGACTATCTTATCTATGTCCAC |
| | GTGGACATAGATAAGATAGTCTTGGACTATCTTATCTATGACAATAGC |
| | CTATTGTCATAGGATAAGTCCAAGACTATCTTATCGACTATTGTCCACAAG |
| | CTTGTGGACAATAGTCGATAAGATTGTTGGACTTATCCTATGACAATAG |
| X-region_DV670-114 R* | TTGTGGACATAGATAAGAT |
| | AGTCTTGGACATTATCATATGACTAACTTGACCTCCACAGAGCCAGTATCA |
| X-region_DV65-51 R* | GAAGACCAAGAAAATTTAAAACGATACATACTTTAAGCTTGATCATTCCACTTGGATGGTCAGTATCA |
| | ACCGCCAGTATCA |

*Only reverse primer sequences are provided here. Use X-region F for pairing the mutagenesis.

FIG. 21

| Human Genes Primers | Forward/reverse primers (5' to 3') |
| --- | --- |
| GAPDH | GCAAATTCCATGGCACCGT/ TCGCCCCACTTGATTTTGG |
| ACTB | AGAGCTACGAGCTGCCTGAC/ CGTGGATGCCACAGGACT |
| IFNB1 | GTCAGAGTCGAAATCCTAAG/ ACAGCATCTGCTGGTTGAAG |
| IFIT1 | GGATTCTGTACAATACACTAGAAACCA/ CTTTTGGTTACTTTTCCCCTATCC |
| Mice Genes Primers | |
| *Tuba1b* | TGCCTTTGTGCACTGGTATG/ CTGGAGCAGTTTGACGACAC |
| *Rps11* | CGTGACGAAGATGAAGATGC/ GCACATTGAATCGCACAGTC |
| *Ifnb* | AGATGTCCTCAACTGCTCTC/ AGATTCACTACCAGTCCCAG |
| *Ifit1* | CAACCAAGTGTTCCAATGCTCCTTC/ TTGCCTGCTAGACAGGGTCAGAAAG |
| Viral Genes Primers | |
| *SeV Np* | TGCCCTGGAAGATGAGTTAG/ GCCTGTTGGTTTGTGGTAAG |
| *DVG* | CCTCAGGTTCCTGATCTCAC/ ACCAGACAAGAGTTTAAGAGATATGTATT |

FIG. 22

DDO (DVG-268)

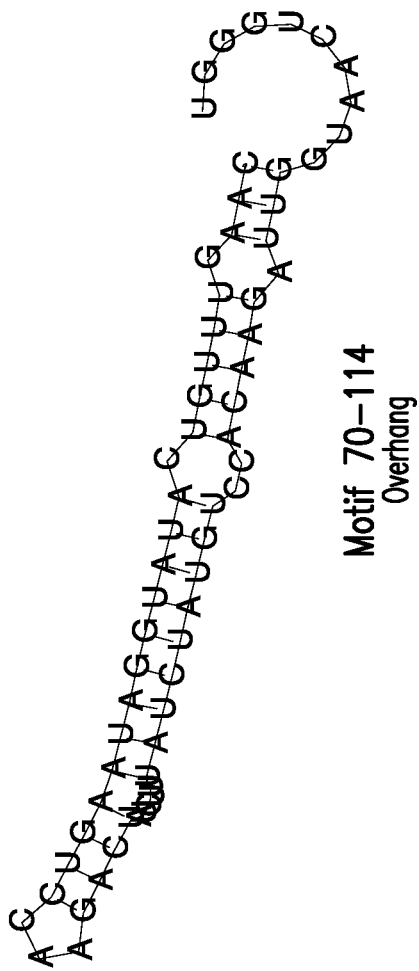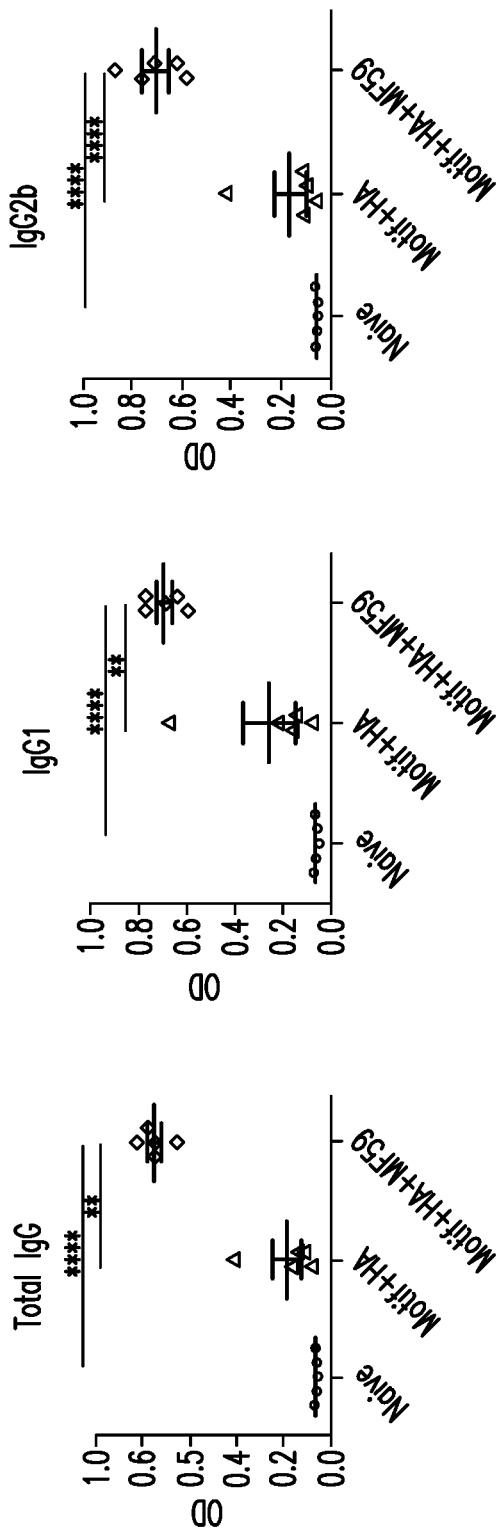
FIG. 27

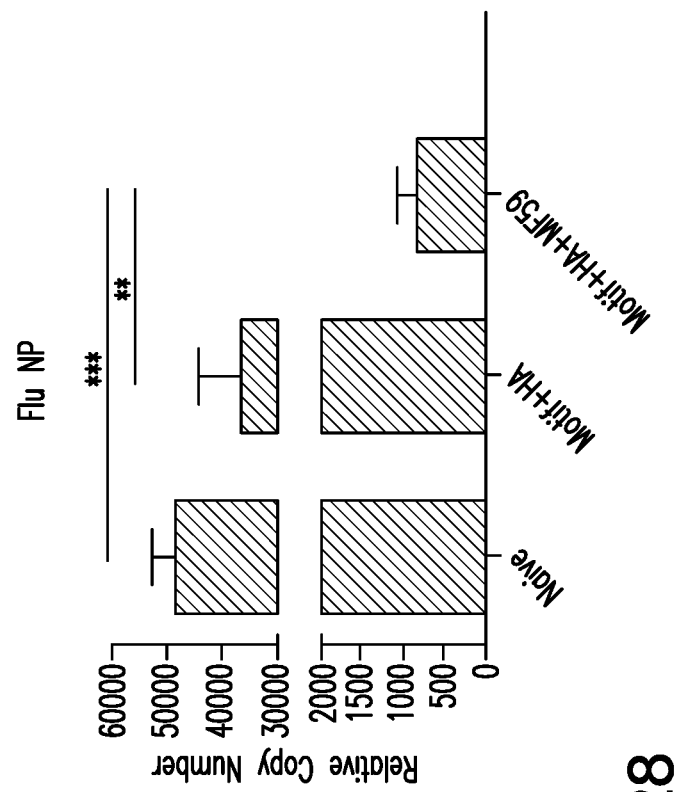
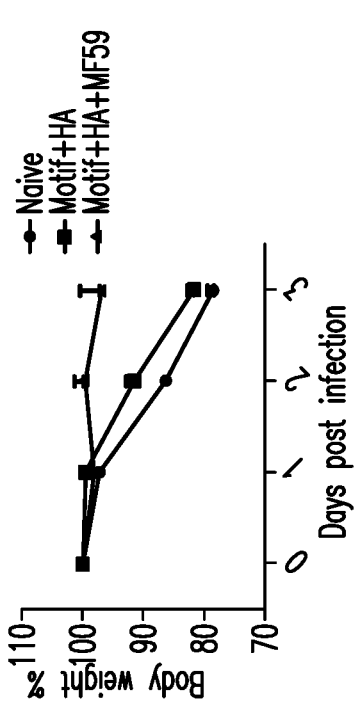
FIG. 28

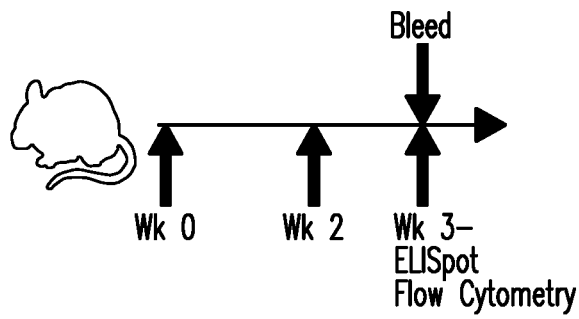
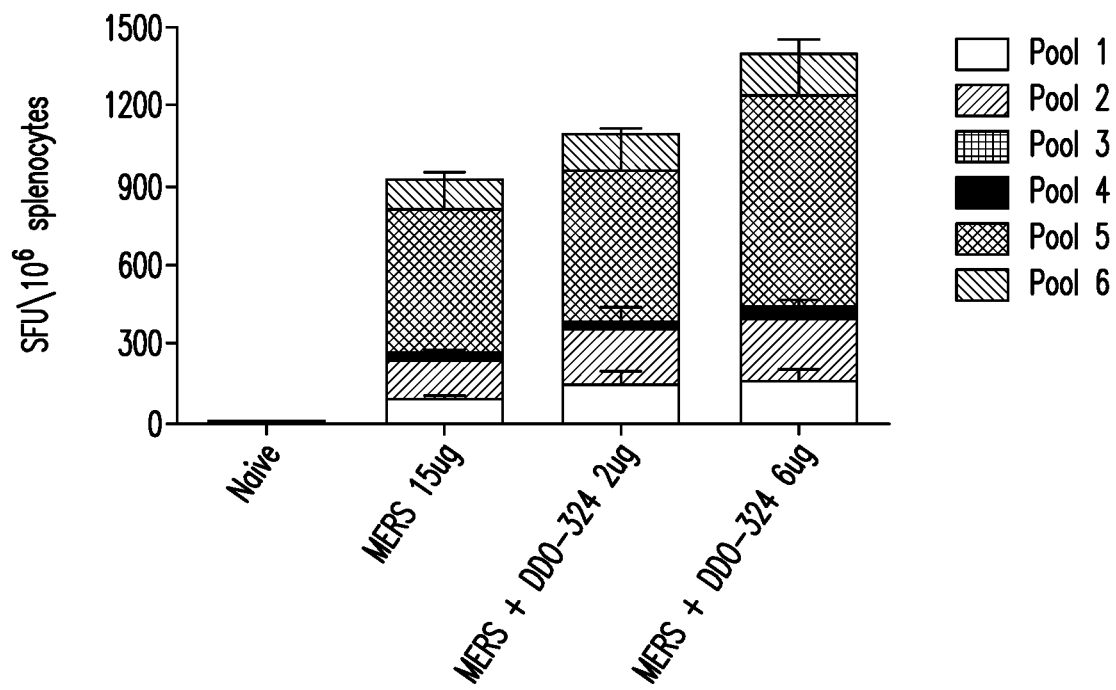
FIG. 31

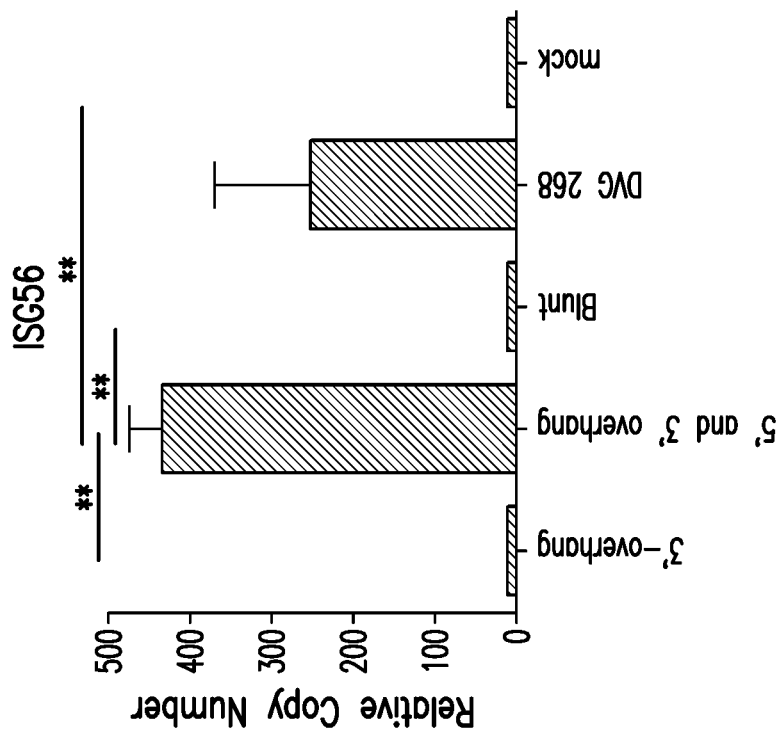
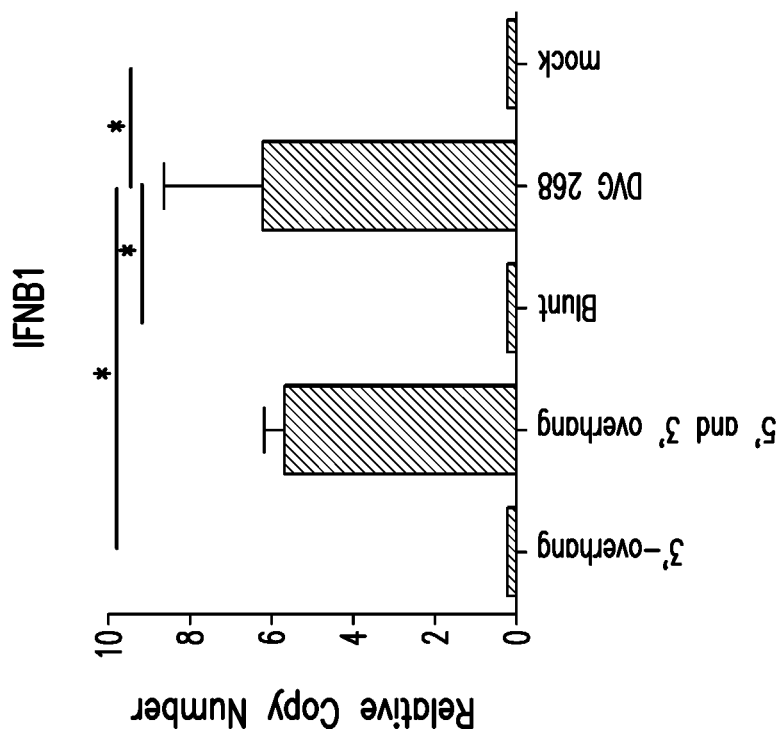
FIG. 32

SEQUENCE LISTING

```
<160> NUMBER OF SEQ ID NOS: 87

<210> SEQ ID NO 1
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
uugucauaug gauaagucca agacuaucuu uaucuauguc cacaa           45

<210> SEQ ID NO 2
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
uugucauaua ggauaagucc aagacuaucu uuaucuuaug uccacaa         47

<210> SEQ ID NO 3
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
uugucauaug gauaagucca agacuaucuu uaucuagguc caca            44

<210> SEQ ID NO 4
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uugucauaug gauaagucca agacuauguu uaucuauguc cacaa           45
```

```
<210> SEQ ID NO 5
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
uugucauaug gauaaguccu agacuaucuu uaucuauguc cacaa              45

<210> SEQ ID NO 6
<211> LENGTH: 225
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 6
accagacaag aguuuaagag auauguaucc uuuuaaauuu ucuugucuuc uuguaaguuu    60
uucuugcuau ugucauaugg auaaguccaa gacuaucuuu aucuaugucc acaagauugg   120 uaacugagguc auucccugac cagaaguuug aagcaagacu ucaauuagga auaguuucau  180
uaucaucccg ugagaucagg aaccugaggg uuaucacaaa gguac                  225

<210> SEQ ID NO 7
<211> LENGTH: 546
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 7
accagacaag aguuuaagag auauguaucc uuuuaaauuu ucuugucuuc uuguaaguuu    60
uucuugcuau ugucauaugg auaaguccaa gacuaucuuu aucuaugucc acaagauugg   120
uaacuggguc auucccugac cagaaguuug aagcaagacu ucaauuagga auaguuucau   180
uaucaucccg ugagaucagg aaccugaggg uuaucacaaa aacuuauua gacagguuug    240 aggauauuau acauaguaua acguauagau uccucaccaa agaaauaaag aucuugauga   300
agauuuuagg ggcagucaag auguucgggg ccaggcaaaa ugaauacacg accgugauuu   360
augauggauc acugggugau aucgagccau ugacagcuc guaauaauua gucccuaucg    420
ugcagaacga ucgaagcucc gcgguaccug gaagucuugg acuuauccau augcaauag    480 uaagaaaaac uuacaagaag acaagaaaau uuaauaggau acauaucucu uaaacucuug   540
ucuggu                                                             546

<210> SEQ ID NO 8
<211> LENGTH: 324
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 8
accagacaag aguuuaagag auauguaucc uuuuaaauuu ucuugucuuc uuguaaguuu    60
uucuugcuau ugucauaugg auaaguccaa gacuaucuuu aucuaugucc acaagauugg   120
uaacuggguc auucccugac cagaaguuug aagcaagacu ucaauuagga auaguuucau   180
```

| | | |
|---|---|---|
| uaucaucccg ugagaucagg aaccugaggg uuaucacaaa gguaccugga agucuuggac | 240 | |
| uuauccauau gacaauagua agaaaaacuu acaagaagac aagaaaauuu aauaggauac | 300 | |
| auaucucuua aacucuuguc uggu | 324 | |

<210> SEQ ID NO 9
<211> LENGTH: 268
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 9

| | |
|---|---|
| accagacaag aguuuaagag auauguaucc uuuuaaauuu ucuugcuuc uuguaaguuu | 60 |
| uucuugcuau ugucauaugg auaaguccaa gacuaucuuu aucuaugcc acaagauugg | 120 |
| uaacuggguc auucccugac cagaaguuug aagcaagacu ucccgguacc uggaagucuu | 180 |
| ggacuuaucc auaugacaau aguaagaaaa acuuacaaga agacaagaaa auuuaauagg | 240 |
| auacauaucu cuuaaacucu ugucuggu | 268 |

<210> SEQ ID NO 10
<211> LENGTH: 200
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 10

| | |
|---|---|
| accagacaag aguuuaagag auauguaucc uuuuaaauuu ucuugcuuc uuguaaguuu | 60 |
| uucuugcuau ugucauaugg auaaguccaa gacuauggua ccggaaguc uuggacuuau | 120 |
| ccauaugaca auaguaagaa aaacuuacaa gaagacaaga aaauuuaaua ggauacauau | 180 |
| cucuuaaacu cuugucuggu | 200 |

<210> SEQ ID NO 11
<211> LENGTH: 353
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 11

| | |
|---|---|
| ccuuuaucua uguccacaag auugguaacu gggucauucc cugaccagaa guugaagca | 60 |
| agacuucaau uaggaauagu uucauuauca ucccgugaga ucaggaaccu gaggguuauc | 120 |
| acaaaaacuu uauugacag guugaggau auuauacaua guauaacgua uagauuccuc | 180 |
| accaaagaaa uaaagauuuu gaugaagauu uuaggggcag ucaagauguu cggggccagg | 240 |
| caaaaugaau acacgaccgu gauugaugau ggaucacugg gugauaucga gccauaugac | 300 |
| agcucguaau aauuagcccc uaucgugcag aacgaucgaa gcuccgcggu acc | 353 |

<210> SEQ ID NO 12
<211> LENGTH: 268
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 12

```
accagacaag aguuuaagag auauguaucc uuuuaaauuu ucuugucuuc uuguaaguuu      60
uucuugcuau ugucauaugg auaaguccaa gacuaucuuu aucuaggucc acaagauugg     120
uaacuggguc auucccugac cagaaguuug aagcaagacu ucccgguacc uggaagucuu     180
ggacuuaucc auaugacaau aguaagaaaa acuuacaaga agacaagaaa auuuaauagg     240
auacauaucu cuuaaacucu ugucuggu                                       268
```

<210> SEQ ID NO 13
<211> LENGTH: 268
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 13

```
accagacaag aguuuaagag auauguaucc uuuuaaauuu ucuugucuuc uuguaaguuu      60
uucuugcuau ugucauaugg auaaguccua gacuaucuuu aucuauguCC acaagauugg     120
uaacuggguc auucccugac cagaaguuug aagcaagacu ucccgguacc uggaagucuu     180
ggacuuaucc auaugacaau aguaagaaaa acuuacaaga agacaagaaa auuuaauagg     240
auacauaucu cuuaaacucu ugucuggu                                       268
```

<210> SEQ ID NO 14
<211> LENGTH: 268
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 14

```
accagacaag aguuuaagag auauguaucc uuuuaaauuu ucuugucuuc uuguaaguuu      60
uucuugcuau ugucauaugg auaaguccaa gacuauguuu aucuaugucc acaagauugg     120
uaacuggguc auucccugac cagaaguuug aagcaagacu ucccgguacc uggaagucuu     180
ggacuuaucc auaugacaau aguaagaaaa acuuacaaga agacaagaaa auuuaauagg     240
auacauaucu cuuaaacucu ugucuggu                                       268
```

<210> SEQ ID NO 15
<211> LENGTH: 501
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 15

```
accagacaag aguuuaagag auauguaucc uuuuaaauuu ucuugucuuc uuguaaguuu      60
uucuugcuag auuggguaacu gggucauucc cugaccagaa guuugaagca agacuucaau    120
uaggaauagu uucauuauca ucccgugaga ucaggaaccu gagggguuauc acaaaaacuu    180 uauuagacag guuugaggau auuauacaua guauaacgua uagauccuuc accaaagaaa    240
uaaagaucuu gaugaagauu uuaggggcag ucaagauguu cggggccagg caaaaugaau    300
acacgaccgu gauugaugau ggaucacugg gugauaucga gccauaugac agcucguaau    360
aauuagcccc uaucgugcag aacgaucgaa gcuccgcggu accuggaagu cuuggacuua    420
uccauaugac aauaguaaga aaaacuuaca agaagacaag aaauuuaaau aggauacaua    480
```

```
ucucuuaaac ucuugucugg u                                              501
```

<210> SEQ ID NO 16
<211> LENGTH: 548
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 16

```
accagacaag aguuuaagag auauguaucc uuuuaaauuu ucuugucuuc uuguaaguuu     60
uucuugcuau ugucauauag gauaagucca agacuaucuu uaucuuaugu ccacaagauu    120
gguaacuggg ucauucccug accagaaguu ugaagcaaga cuucaauuag gaauaguuuc    180
auuaucaucc cgugagauca ggaaccugag gguuaucaca aaaacuuuau uagacagguu    240
ugaggauauu auacauagua uaacguauag auuccucacc aaagaaauaa agaucuugau    300
gaagauuuua ggggcaguca agauguucgg ggccaggcaa aaugaauaca cgaccgugau    360
ugaugaugga ucacuggguu auaucgagcc auaugacagc ucguaauaau uagucccuau    420
cgugcagaac gaucgaagcu ccgcgguacc uggaagucuu ggacuauccc auaugacaau    480
aguaagaaaa acuuacaaga agacaagaaa auuuaauagg auacauaucu cuuaaacucu    540
ugucuggu                                                             548
```

<210> SEQ ID NO 17
<211> LENGTH: 98
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17

```
gguggcucca ucuuagcccu agucacggcu agcugugaaa gguccgugag ccgcuugacu     60
gcagagagug cugauacugg ccucucugca gaucaagu                             98
```

<210> SEQ ID NO 18
<211> LENGTH: 143
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 18

```
gguggcucca ucuuagcccu agucacggcu agcugugaaa gguccgugag ccgcuugacu     60
gcagagagug cugauacugg ccucucugca gaucaaguuu gucauaugga uaguccaag     120
acuaucuuua ucuaugucca caa                                            143
```

<210> SEQ ID NO 19
<211> LENGTH: 144
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 19

```
gguggcucca ucuuagcccu agucacggcu agcugugaaa gguccgugag ccgcuugacu     60
```

```
gcagagagug ugauacuggc cucucugcag aucaagugac aagaguuuaa gagauaugua        120
uccuuuuaaa uuuucuuguc uucu                                              144

<210> SEQ ID NO 20
<211> LENGTH: 180
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 20
accagacaag aguuuaagag auauguaucc uuuuaaauuu ucuugcuuc uuguaaguuu         60 uucuugcuag auugguaacu gggucauucc cugaccagaa guugaagca agacuucaau        120 uaggaauagu ucauuauca ucccgugaga ucaggaaccu gagguuauc acaaagguac         180

<210> SEQ ID NO 21
<211> LENGTH: 223
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 21
accagacaag aguuuaagag auauguaucc uuuuaaauuu ucuugcuuc uuguaaguuu         60 uucuugcuag auugguaacu gggucauucc cugaccagaa guugaagca agacuucccg        120 guaccuggaa gucuuggacu uauccauaug acaauaguaa gaaaaacuua caagaagaca       180
agaaaauuua auaggauaca uaucucuuaa acucuugucu ggu                         223

<210> SEQ ID NO 22
<211> LENGTH: 55
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
uugucauaug gauaagucca agacuaucuu uaucuaugua cacaagauug guaac            55

<210> SEQ ID NO 23
<211> LENGTH: 65
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
caaguuuguc auauggauaa guccaagacu aucuuuaucu auguccacaa gauugguaac       60
ugggu                                                                   65

<210> SEQ ID NO 24
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
```
caaguuuguc auauggauaa guccaagacu aucuuuaucu auguccacaa        50

<210> SEQ ID NO 25
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gttcttgtaa gttttcttg ctagattggt aactgggtca ttccc              45

<210> SEQ ID NO 26
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gggaatgacc cagttaccaa tctagcaaga aaaacttaca agaac             45

<210> SEQ ID NO 27
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cgactcacta tagggaccat gtaagttttt cttgctattg tc                42

<210> SEQ ID NO 28
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gacaatagca agaaaaactt acatggtccc tatagtgagt cg                42

<210> SEQ ID NO 29
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gtccaagact atctttatct aggtccacaa gattggtaac tg                42

<210> SEQ ID NO 30
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gtccaagact atctttatct aggtccacaa gattggtaac tg                42

<210> SEQ ID NO 31
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gtttttcttg ctattgtcat ctggataagt ccaagactat c                 41

<210> SEQ ID NO 32
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gatagtcttg gacttatcca gatgacaata gcaagaaaaa c                 41

<210> SEQ ID NO 33
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gctattgtca tatggataag tcctagacta tctttatcta tgtccac           47

<210> SEQ ID NO 34
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtggacatag ataaagatag tctaggactt atccatatga caatagc           47

<210> SEQ ID NO 35
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ggataagtcc aagactatgt ttatctatgt ccacaagatt gg                42

<210> SEQ ID NO 36
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ccaatcttgt ggacatagat aaacatagtc ttggacttat cc                42

<210> SEQ ID NO 37
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gctattgtca tataggataa gtccaagact atctttatct tatgtccac          49

<210> SEQ ID NO 38
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtggacataa gataaagata gtcttggact tatcctatat gacaatagc          49

<210> SEQ ID NO 39
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ctattgtcat aggataagtc caagactatc tttatcttgt ccacaag            47

<210> SEQ ID NO 40
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cttgtggaca agataaagat agtcttggac ttatcctatg acaatag            47

<210> SEQ ID NO 41
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
taatacgact cactataggt ggctccatct tagccta                       38

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
acttgatctg cagagaggcc agtatca                                  27

```
<210> SEQ ID NO 43
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
taatacgact cactataggc catcctgttt ttttccc                              37

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aaaggaaaga aaaggaaaaa aagagg                                          26

<210> SEQ ID NO 45
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ttgtggacat agataaagat agtcttggac ttatccatat gacaaacttg atctgcagag     60
aggccagtat ca                                                         72

<210> SEQ ID NO 46
<211> LENGTH: 73
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gaagacaaga aaatttaaaa ggatacatat ctcttaaact cttgtcactt gatctgcaga     60
gaggccagta tca                                                        73

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggtgaggaat ctatacgtta tac                                             23

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
```

-continued cctcaggttc ctgatctc                                           18

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ggtgaggaat ctatacgtta tac                                     23

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cctcaggttc ctgatctc                                           18

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
accagacaag agtttaagag atatg                                   25

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
agcaagaaaa acttacaaga agaca                                   25

<210> SEQ ID NO 53
<211> LENGTH: 452
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 53
accagacaag aguuuaagag auauguaucc uuuuaaauuu ucuugcuuc uuguaaguuu     60 uucuugcuau ugucauaugg auaaguccaa gacuaucuuu aucauguccc acaagauugg   120
uaacuggguc auucccugac cagaaguuug aagcaagacu ucaauuagga auaguuucau   180
uaucaucccg ugagaucagg aaccugaggg uuauacaaaa aacuuuauua gacagguuug   240
aggauauuau acauaguaua acguauagau uccucaccaa agaaauaaag aucuugauga   300
agauuuuagg ggcagucaag auguucgggg ccaggcaaaa ugaauacacg accgugauug   360
augauggauc acuggguugau aucgagccau augacagcuc guaauaauua gucccuaucg   420
ugcagaacga ucgaagcucc gcgguaccug ga                               452

<210> SEQ ID NO 54
<211> LENGTH: 260
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 54
accagacaag aguuuaagag auauguaucc uuuuaaauuu ucuugcuuc uuguaaguuu    60 uucuugcuau ugcauaugg auaaguccaa gacuauggau cuugaugaag auuuuagggg   120
cagucaagau guucggggcc aggcaaaaug aauacacgac cgugauugau gauggaucac  180
ugggugauau cgagccauau gacagcucgu aauaauuagu cccuaucgug cagaacgauc  240
gaagcuccgc gguaccugga                                             260

<210> SEQ ID NO 55
<211> LENGTH: 200
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 55
ccuuuaucua uguccacaag auugguaacu gggucauucc cugaccagaa guugaagca    60 agacuucaau uaggaauagu uucauuauca ucccgugaga ucaggaaccu gaggguuauc  120
acaaaaacuu uauuagacag guuugaggau auuauacaua guauaacgua uagauuccuc  180
accaaagaaa uaaagauuuu                                              200

<210> SEQ ID NO 56
<211> LENGTH: 106
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 56
accagacaag aguuuaagag auauguaucc uuuuaaauuu ucuugcuuc uuguaaguuu    60 uucuugcuau ugcauaugg auaaguccaa gacuauggua ccugga                 106

<210> SEQ ID NO 57
<211> LENGTH: 54
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
uucuugcuau ugcauaugg auaaguccaa gacuaucuuu aucuauguccc acaa          54

<210> SEQ ID NO 58
<211> LENGTH: 174
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 58
accagacaag aguuuaagag auauguaucc uuuuaaauuu ucuugucuuc uuguaaguuu    60
uucuugcuau ugucauaugg auaagccaa gacuaucuuu aucuaugucc acaagauugg    120
uaacuggguc auucccugac cagaaguuug aagcaagacu ucccgguacc ugga         174

<210> SEQ ID NO 59
<211> LENGTH: 129
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 59
accagacaag aguuuaagag auauguaucc uuuuaaauuu ucuugucuuc uuguaaguuu    60
uucuugcuag auugguaacu gggucauucc cugaccagaa guugaagca agacuucccg    120 guaccugga                                                           129

<210> SEQ ID NO 60
<211> LENGTH: 174
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 60
accagacaag aguuuaagag auauguaucc uuuuaaauuu ucuugucuuc uuguaaguuu    60
uucuugcuau ugucauaugg auaagccaa gacuaucuuu aucuaggucc acaagauugg    120
uaacuggguc auucccugac cagaaguuug aagcaagacu cccgguacc ugga          174

<210> SEQ ID NO 61
<211> LENGTH: 174
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 61
accagacaag aguuuaagag auauguaucc uuuuaaauuu ucuugucuuc uuguaaguuu    60
uucuugcuau ugucauaugg auaagccua gacuaucuuu aucuaugucc acaagauugg    120
uaacuggguc auucccugac cagaaguuug aagcaagacu ucccgguacc ugga         174

<210> SEQ ID NO 62
<211> LENGTH: 174
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 62
accagacaag aguuuaagag auauguaucc uuuuaaauuu ucuugucuuc uuguaaguuu    60
uucuugcuau ugucauaugg auaagccaa gacuauguuu aucuaugucc acaagauugg    120 uaacugggguc auucccugac cagaaguuug aagcaagacu ucccgguacc ugga        174

<210> SEQ ID NO 63
<211> LENGTH: 225

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
accagacaag aguuuagag auauguaucc uuuuaaauuu ucuugucuuc uuguaaguuu      60
uucuugcuau ugucauaugg auaaguccaa gacuaucuuu aucuaugucc acaagauugg    120
uaacuggguc auucccugac cagaaguuug aagcaagacu caauuagga auaguuucau    180 uaucaucccg ugagaucagg aaccugaggg uuaucacaaa gguac                    225

<210> SEQ ID NO 64
<211> LENGTH: 407
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 64
accagacaag aguuuagag auauguaucc uuuuaaauuu ucuugucuuc uuguaaguuu      60
uucuugcuag auugguaacu ggguccauuc cugaccagaa guugaagca agacuucaau    120 uaggaauagu ucauuauca ucccgugaga ucaggaaccu gagggguuauc acaaaaacuu   180 uauuagacag guugaggau auuauacaua guauaacgua uagauuccuc accaaagaaa    240
uaaagaucuu gaugaagauu uuagggggcag ucaagauguu cggggccagg caaaaugaau   300
acacgaccgu gauugaugau ggaucacugg gugauaucga gccauaugac agcucguaau   360 aauuagucc uaucgugcag aacgaucgaa gcuccgcggu accugga                  407

<210> SEQ ID NO 65
<211> LENGTH: 454
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 65
accagacaag aguuuagag auauguaucc uuuuaaauuu ucuugucuuc uuguaaguuu      60
uucuugcuau ugucauauag gauaaguccaa agacuaucuu uaucuuaugu ccacaagauu  120
gguaacuggg ucauucccug accagaaguu ugaagcaaga cuucaauuag gaauaguuuc   180
auuaucaucc cgugagauca ggaaccugag gguuaucaca aaacuuuau uagacagguu   240 ugaggauauu auacauagua uaacguauag auuccucacc aaagaaauaa agaucuugau   300
gaagauuuua gggggcaguca agauguucgg ggccaggcaa aaugaauaca cgaccgugau   360
ugaugaugga ucacugggug auaucgagcc auaugacagc ucguaauaau uagucccuau   420
cgugcagaac gaucgaagcu ccgcgguacc ugga                                454

<210> SEQ ID NO 66
<211> LENGTH: 178
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 66
```
accauguaag uuuuucuugc uauugucaua uggauaaguc caagacuauc uuuaucuaug        60
uccacaagau ugguaacugg gucauuccu gaccagaagu uugaagcaag acuucaauua       120
ggaauaguuu cauuaucauc ccgugagauc aggaaccugu ggguuaucag aaagguac        178

<210> SEQ ID NO 67
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
gacaagaguu uaagagauau guauccuuuu aaauuuucuu gcuucu                     47

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gcaaattcca tggcaccgt                                                   19

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69 tcgcccact tgattttgg                                                    19

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
agagctacga gctgcctgac                                                  20

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cgtggatgcc acaggact                                                    18

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gtcagagtcg aaatcctaag                                                   20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
acagcatctg ctggttgaag                                                   20

<210> SEQ ID NO 74
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ggattctgta caatacacta gaaacca                                           27

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cttttggtta cttttcccct atcc                                              24

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
tgcctttgtg cactggtatg                                                   20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ctggagcagt ttgacgacac                                                   20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cgtgacgaag atgaagatgc                                              20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gcacattgaa tcgcacagtc                                              20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
agatgtcctc aactgctctc                                              20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
agattcacta ccagtcccag                                              20

<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
caaccaagtg ttccaatgct ccttc                                        25

<210> SEQ ID NO 83
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ttgcctgcta gacagggtca gaaag                                        25

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84

-continued

```
tgccctggaa gatgagttag                                              20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gcctgttggt ttgtggtaag                                              20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
cctcaggttc ctgatctcac                                              20

<210> SEQ ID NO 87
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
accagacaag agtttaagag atatgtatt                                    29
```

METHODS AND COMPOSITIONS FOR STIMULATING IMMUNE RESPONSE USING POTENT IMMUNOSTIMULATORY RNA MOTIFS

CROSS-REFERENCE TO RELATED APPLICATIONS

This application is a U.S. National Stage Patent Application under 35 U.S.C. § 371 of International Application No. PCT/US2016/30242, filed on Apr. 29, 2016, which claims priority to U.S. Provisional Application No. 62/155,740, filed May 1, 2015, which are incorporated by reference herein in their entirety.

STATEMENT REGARDING FEDERALLY SPONSORED RESEARCH OR DEVELOPMENT

This invention was made with government support under NIH Grant Numbers R01-AI083284 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on May 16, 2019, is named 081406_0316_SL.txt and is 29,314 bytes in size.

FIELD OF THE INVENTION

The presently disclosed subject matter relates, in certain embodiments, to immunostimulatory RNA motifs as well as methods for initiating or enhancing immune responses. In certain embodiments, these RNA motifs can be used as immunostimulatory agents to enhance host immune responses, as antivirals, as vaccine adjuvants, and/or as anti-tumor agents.

BACKGROUND

The immune system plays an important role in defense against specific microorganisms, for example viruses, specific fungi and bacteria, as well as in recognizing and inhibiting and/or eradicating tumor cells. Vaccinations are a long-known method of activating the immune system. Vaccination and immunization is the introduction of a non-virulent agent into a subject, in which the agent elicits the subject's immune system to mount an immunological response. Often, vaccine antigens are killed or attenuated forms of the microbes which cause the disease. The presence of non-essential components and antigens in these killed or attenuated vaccines has encouraged considerable efforts to refine vaccine components including developing well-defined synthetic antigens using chemical and recombinant techniques. The refinement and simplification of vaccines, however, has led to a concomitant loss in potency. Low-molecular weight synthetic antigens, though devoid of potentially harmful contaminants, are often not sufficiently immunogenic by themselves and do not produce an adequate immune response.

The immunogenicity of an antigen can be increased by administering it in a mixture with substances called adjuvants. Adjuvants increase the response against the antigen either by directly acting on the immunological system or by modifying the pharmacokinetic characteristics of the antigen, resulting in an increased interaction time between the antigen and the immune system. Additionally, the addition of an adjuvant can permit the use of a smaller dose of antigen to stimulate a similar immune response, thereby reducing the production cost of a vaccine.

Currently the most widely adjuvants used in humans are Aluminum salts. Aluminum salts have been useful for some vaccines like hepatitis B, diphtheria, tetanus, and toxoid; however, they are not useful for others like rabies, MMR, and typhoid. In addition, Aluminum salts fail to induce cell-mediated immunity, result in the induction of granulomas at the injection site and vary in effectiveness between batches of alum preparations.

Detection of specific viral pathogen-associated molecular patterns (PAMPs) by host pathogen recognition receptors (PRRs) is the first event in the defense against virus infection (1-3). During infection with RNA viruses, the RIG-I-like receptors (RLRs) RIG-I (retinoic acid-inducible gene I) and MDA5 (melanoma differentiation-associated protein 5) bind viral PAMPs present in the infected cell and initiate a signaling cascade mediated by the mitochondrial antiviral signaling molecule (MAVS), which culminates in the production of type I IFNs and other antiviral genes (4-6). This primary host response to infection is essential to control virus replication and to initiate protective antiviral immunity (7). RNA motifs that effectively trigger this pathway are disclosed herein, which can, in certain embodiments, be used to generate synthetic RLR ligands for strong induction of antiviral responses in the context of vaccination or antiviral therapies.

5'-di- or -triphosphates associated with double strand RNA (dsRNA) or with single strand RNA, with or without poly U/UC ssRNA stretches, trigger RIG-I stimulation (1, 3, 8-10). These structures are present in influenza A virus (IAV) (8, 11), Sendai virus (SeV) (12), Hepatitis C virus (HCV) (13-15), and reovirus (16, 17). MDA5 ligands are much less characterized and are presumed to be complex secondary RNA structures (18, 19).

During infection with viruses that are adapted to the host, viral-encoded proteins interfere with RLR activity allowing the virus to reach high titers prior to the onset of the antiviral response (20-22). The delay in detection of viral structures that are normally present in the viral genomes during natural infections indicates that additional factors are required for the effective triggering of antiviral responses in vivo. During infection with SeV, potent stimuli for the initiation of the antiviral response is provided by immunostimulatory defective viral genomes (iDVGs) generated during virus replication at high titers (23-25). SeV iDVGs trigger RLR signaling and initiate strong antiviral immunity both in vitro and during natural infections in vivo (26, 27). SeV iDVGs belong to the copy-back type of RNA DVGs and are produced when the viral polymerase is released from the template strand during replication and copies back the nascent strand (28). iDVGs are unable to replicate in the absence of helper virus as they lack essential replication machinery, and are not transcribed into proteins as they are flanked by the antigenomic promoter (29-32). A copy-back iDVG of 546 nucleotides (DVG-546) predominant in laboratory stocks of SeV strain Cantell (SeV C) has been characterized to be a strong trigger of RLRs signaling (12, 23, 26, 33). Although this activity largely depends on 5'triphosphates and the presence of dsRNA structures, prior to the instant disclosure, it was unclear whether additional RNA motifs optimize the immunostimulatory potential DVG-546 contributing to its efficient recognition even in the presence of virus-encoded antagonists of the antiviral response (25, 34).

SUMMARY

The present disclosure is based, in part, on an RNA motif ($DVG_{70-114}$) that is capable of eliciting an immune response. For example, but not by way of limitation, this motif can be harnessed to increase the immunostimulatory potential of otherwise inert RNAs and represents a novel immunostimulatory enhancer that can be used in the development of vaccine adjuvants and antivirals.

In certain embodiments, the instant disclosure provides methods for stimulating an immune response in a subject including administering to the subject, e.g., a mammalian subject or a non-mammalian subject, e.g., a human, bird, or fish, at least one antigen in conjunction with an RNA motif capable of inducing an antigen specific immune response in the subject.

In certain embodiments, the present disclosure provides methods of activating an antigen presenting cell, for example a dendritic cell, including contacting the cell with an antigen and an RNA motif capable of inducing an antigen specific immune response. In certain embodiments, the antigen presenting cell is isolated from a subject and activated ex vivo. The activated cell can then be introduced, or reintroduced, into the subject.

In certain embodiments, the instant disclosure provides methods for stimulating an immune response in a subject including administering to the subject an antibody conjugated to at least one RNA motif capable of inducing an antigen specific immune response in the subject.

In certain embodiments, the disclosure provides methods for stimulating an immune response in a subject to an immunostimulatory-inert virus including administering to the subject a portion of the inert virus's genome in which at least one RNA motif capable of inducing an antigen specific immune response in the subject is cloned into the genome.

In certain embodiments, the RNA motif comprises the nucleotide sequence of SEQ ID NO:1, or modified variants thereof having immunostimulatory activity. In certain embodiments, the RNA motif comprises the nucleotide sequence of SEQ ID NO:2. In certain embodiments, the RNA motif comprises the nucleotide sequence of SEQ ID NO:5. In certain embodiments, the antigen is, for example, a virus, bacterial, fungal, parasite, nucleotide, or peptide antigen.

In certain embodiments, the present disclosure also provides pharmaceutical compositions comprising an RNA motif comprising the nucleotide sequence of SEQ ID NO: 1, SEQ ID NO:2, SEQ ID NO:5, SEQ ID NO: 23, or a modified variant of SEQ ID NO:1 having immunostimulatory activity and a pharmaceutically acceptable carrier.

In certain embodiments, the present disclosure also provides pharmaceutical compositions comprising an RNA motif comprising the nucleotide sequence of SEQ ID NO: 1, SEQ ID NO:2, SEQ ID NO:5, SEQ ID NO: 23, or a modified variant of SEQ ID NO:1 having immunostimulatory activity, one or more adjuvant, and a pharmaceutically acceptable carrier.

In certain embodiments, the present disclosure also provides pharmaceutical compositions comprising an RNA motif comprising the nucleotide sequence of SEQ ID NO:1, SEQ ID NO:2, SEQ ID NO:5, SEQ ID NO: 23, or a modified variant of SEQ ID NO:1 having immunostimulatory activity, one or more antigens, and a pharmaceutically acceptable carrier.

In certain embodiments, the present disclosure also provides pharmaceutical compositions comprising an RNA motif comprising the nucleotide sequence of SEQ ID NO: 1, SEQ ID NO:2, SEQ ID NO:5, SEQ ID NO: 23, or a modified variant of SEQ ID NO:1 having immunostimulatory activity, conjugated to one or more adjuvant, and a pharmaceutically acceptable carrier.

In certain embodiments, the present disclosure also provides pharmaceutical compositions comprising an RNA motif comprising the nucleotide sequence of SEQ ID NO: 1, SEQ ID NO:2, SEQ ID NO:5, SEQ ID NO: 23 or a modified variant of SEQ ID NO:1 having immunostimulatory activity, conjugated to, combined with, or encapsulated by one or more nanoparticle, and a pharmaceutically acceptable carrier. In certain embodiments, the nanoparticle can be liposome.

In certain embodiments, the present disclosure also provides pharmaceutical compositions comprising an RNA motif comprising the nucleotide sequence of SEQ ID NO: 1, SEQ ID NO:2, SEQ ID NO:5, SEQ ID NO: 23, or a modified variant of SEQ ID NO:1 having immunostimulatory activity, inserted into one or more nucleotide sequence, and a pharmaceutically acceptable carrier. In certain embodiments, the nucleotide sequence can be an mRNA sequence.

In certain embodiments, the present disclosure provides an isolated RNA molecule comprising the nucleotide sequence of SEQ ID NO:1, SEQ ID NO:2, SEQ ID NO:5, SEQ ID NO: 23, or a modified variant of SEQ ID NO: 1 having immunostimulatory activity.

BRIEF DESCRIPTION OF THE FIGURES

FIG. 1A-FIG. 1B. DVGs promote protection from infection with an unrelated virus. (FIG. 1A) Mouse embryo fibroblasts (MEFs) were infected with SeV HD or SeV LD (MOI=1.5 $TCID_{50}$/cell) or left untreated (N/T) and challenged 6 h later with Influenza virus (IAV) (MOI of 1.5). Cells were harvested 12 h after a challenge, and the expression of IAV NP mRNA was examined by qRT-PCR. The data are the percentage of IAV NP mRNA relative to that of N/T cells. (FIG. 1B) Expression of antiviral genes examined by RT-qPCR. Results are expressed as the mean±the standard error of the mean of three independent experiments.

FIG. 2A-FIG. 2D. Accumulation of positive (+)DVG strands associates with strong expression of IFNB1 during infection. (FIG. 2A) Representation of genomic and copy-back DVG RNAs produced during SeV infection. (FIG. 2B) IFNB1 mRNA expression and ratio of (+)/(−)DVG RNA copy numbers determined by RT-qPCR from A549 cells infected with SeV-HD at a moi of 1.5 $TCID_{50}$/cell. Experiments were independently repeated at least three times. Each assay was performed in triplicates. A representative graph is shown. (FIG. 2C) Representative staining of (+)DVG (green), (+)SeV genome or mRNA (red), IRF3 (purple) and nuclei (DAPI, blue) on LLC-MK2 cells 6 h after SeV HD infection or mock controls. Image magnification: 100×. (FIG. 2D) Quantification of IRF3 nuclear translocation within total, DVG-containing cells, and DVG negative cells. Results are expressed as mean±SEM from three independent experiments. ***p<0.001 by one-way ANOVA with Bonferroni post hoc test. Data are expressed as copy numbers relative to the housekeeping gene GAPDH. ns=non-significant.

(FIG. 3A) Scheme of PCR amplification strategy utilized to detect and differentiate (+) and (−) strands of DVG-546. DVG reverse transcription was performed with the indicated primers for the (+) or (−) sense DVGs. RT-qPCR of each sense-specific RT product was performed with a combination of the DVG 1 and DVG J primers to produce identical PCR products at equivalent efficiencies. While the DVG1 primer will serve to reverse transcribe the (+) sense of both DVG-546 and the SeV HD genome, the DVG J primer spans the junction site between the inverse trailer and the internal DVG sequence, which is unique to the DVG-546 sequence and is not present in the SeV HD genome. (FIG. 3B) (+)DVG and (−)DVG qPCR efficiency test from TC-1 mouse lung epithelial cells infected with SeV HI) at a moi of 1.5 $TCID_{50}$/cell. Total RNA (lug) isolated 12 h after infection was reverse transcribed for either (+)DVG or (−)DVG. Ten-fold serial dilutions were analyzed for RT-qPCR and cycle threshold (Ct) values for each dilution were graphed relative to the $\log_{10}$ (pg) of initial RNA. The linear region of the standard curve is shown, and was used to determine the $R^2$ value and PCR efficiency, which was calculated as $10^{-1/slope}-1$. (FIG. 3C) Copy numbers of (+)DVGs and (−) DVGs over the course of an A549 infection with SeV HD at a moi of 1.5 $TCID_{50}$/cell. (FIG. 3D) IFNB1 mRNA expression and ratio of (+)/(−) DVG RNA determined by RT-qPCR from LLC-MK2 cells infected with SeV-HD at a moi of 1.5 $TCID_{50}$/cell. All experiments shown in FIG. 3B-FIG. 3D were independently repeated for three times and each assay was performed in triplicate. A representative data set is shown. Data are expressed as copy numbers relative to the housekeeping genes GAPDH.

(FIG. 4A) Representation of deletion DVG mutants. Length of the deletion (dashed line) and total final length of each molecule are indicated. DVG mutant with deletion of both complementary sequences (gray) is indicated as DVG-IS (internal sequence). (FIG. 4B) Expression of IFNB1 and IFIT1 mRNA measured by RT-qPCR from LLC-MK2 cells transfected for 6 h with 4.15 pmol ivtDVGs. Data correspond to the mean±SEM of all experiments (total n=5-11/group). *p<0.05, p<0.01, *p<0.001, ****p<0.0001 by one-way ANOVA with Bonferroni post hoc test. Data are expressed as copy numbers relative to the housekeeping gene GAPDH. (FIG. 4C) Folding prediction of highly stimulatory and poorly stimulatory DVG mutants using RNA fold Vienna software. A temperature option equal to 37° C. was chosen to determine structured based on minimal free energy. Candidate motif ($DVG_{70-114}$) is circled. FIG. 4C depicts partial secondary structural portions of DVG-268, DVG-324, DVG-546, DVG-354, DVG-200, and DVG-IS: SEQ ID NOS 58, 63, 53, 54, 56 and 55, respectively. (FIG. 4D) Relative position of the candidate stimulatory $DVG_{70-114}$ motif and its sequence in the genome of DVG-546. AU content of $DVG_{70-114}$ compared with DVG-546 and full-length genome is indicated in the adjacent table. FIG. 4D discloses SEQ ID NO 1. (FIG. 4E) Folding predictions for DVG-268 and its derived mutants. Structures of intact DVG-268 and $DVG_{70-114}$ motif deletion (A70-114) are shown. Position of $DVG_{70-114}$ is highlighted. Point mutations within the $DVG_{70-114}$ motif are indicated in the grey square. FIG. 4E depicts partial secondary structural portions of DVG-268, DVG-268Δ70-114, DVG-268U106G, DVG-268A89U, DVG-268C97G: SEQ ID NOS 58-62, respectively. (FIG. 4F) LLC-MK2 cells were transfected with 4.15 pmol of the indicated ivtDVG, IFNB1 and IFIT1 mRNA expression was analyzed by RT-qPCR at and 6 h post-transfection. (FIG. 4G) Murine TC-1 cells were transfected with 4.15 pmol of DVG-268 or DVG-268 Δ-70-114, and IFN-beta protein and mRNA levels were measured by ELISA and RT-qPCR, respectively. Data correspond to the mean±SEM of all experiments (total n=3/group). *p<0.05, p<0.01, *p<0.001, ****p<0.0001 by one-way ANOVA with Bonferroni post hoc test. Data are expressed as copy numbers relative to the housekeeping gene GAPDH. ns=non-significant.

FIG. 5A-FIG. 5B. Quality control of ivtDVG RNAs. (FIG. 5A) Electrophoretic analysis of ivtDVGs was performed on an Agilents's 2100 Bioanalyzer. (FIG. 5B). Endotoxin test for ivtDVGs used in the study. (FIG. 5C) Expression of IFNB1 mRNA by RT-qPCR of LLC-MK2 cells transfected for 6 h with 4.15 pmol gel-purified DVG-ivtDVG. The experiment was independently repeated three times and each assay was performed in triplicate. A representative qPCR is shown. RT-qPCR data are expressed as copy numbers relative to the housekeeping genes GAPDH.

FIG. 6A-FIG. 6C. ivtDVGs with intact stimulatory motif stimulate IFN responses in both mouse and human cells and is sustained for up to 24 h post transfection. (FIG. 6A) Expression of Ifnb mRNA by RT-qPCR of TC-1 cells transfected for 6 h with 4.15 pmol of the indicated ivtDVGs. (FIG. 6B) Expression of IFNB1 mRNA by RT-qPCR of A549 cells transfected for 6 h with 4.15 pmol of the indicated ivtDVGs. Each RT-qPCR assay was performed in triplicates. Data correspond to the average of all experiments (total n>3/group). *<0.05, p<0.001, *p<0.001, ****p<0.0001 by one-way ANOVA with Bonferroni post hoc test. RT-qPCR data are expressed as copy numbers relative to the housekeeping genes GAPDH for LL-CMK2 cells and Rps11 for TC-1 cells. (FIG. 6C) Expression of IFNB1 and IFIT1 mRNA at 4, 8, 12, and 24 h post transfection of LL-CMK2 with 4.15 pmol of the indicated ivtDVG RNA. One representative experiment out of three is shown. Data are expressed as copy numbers relative to the housekeeping genes GAPDH.

FIG. 7A-FIG. 7D. Quality control of ivtDVG RNAs. (FIG. 7A) Electrophoretic analysis of ivtDVGs was performed on an Agilent 2100 Bioanalyzer. (FIG. 7B). Endotoxin levels on ivtDVGs used in the study measured by Limulus assay. (FIG. 7C) Expression of IFNB1 mRNA by RT-qPCR of LLC-MK2 cells transfected for 6 h with 4.15 pmol gel-purified ivtDVG. The experiment was independently repeated three times and each assay was performed in triplicate. A representative qPCR is shown. RT-qPCR data are expressed as copy numbers relative to the housekeeping genes GAPDH. (FIG. 7D) The amount of ivtDVGs present upon each transfection was quantified 6 h post transfection by RT-qPCR using a common set of primers directed to the 5'-complementary end of the DVGs (DVG Comp). Two representative transfections in LL-CMK2 cells are shown (EXPs 1 and 2). Data are expressed as copy numbers relative to the housekeeping genes GAPDH.

(FIG. 8A) Eletrophoretic analysis for DVG-268 ivtDVGs on an Agilents's 2100 Bioanalyzer. (FIG. 8B) Eletrophoretic analysis for DVG-546 ivtDVGs on an Agilents's 2100 Bioanalyzer. (FIG. 8C) Folding prediction for DVG-546 motif deletion ($DVG-546_{Δ70-114}$) and the parental DVG-546. Motif $DVG_{70-114}$ is indicated with an oval. FIG. 8C depicts partial secondary structural portions of DVG-546 and DVG-546Δ70-114: SEQ ID NOS 53 and 64, respectively, in order of appearance. (FIG. 8D) Expression of IFNB1 mRNA by RT-qPCR in LLC-MK2 cells transfected for 6 h with 4.15 pmol of the indicated ivtDVG. (FIG. 8E) Folding prediction for DVG-546 motif1+ and the parental DVG-546. Motif DVG$_{70-114}$ is indicated with an oval. Mutated motif DVG$_{70-114}$ in DVG-546 motif1+ is indicated with an oval. (FIG. 8F) Expression of IFNB1 mRNA by RT-qPCR of LLC-MK2 cells transfected for 6 h with 4.15 pmol of ivtDVG illustrated in (FIG. 8E). FIG. 8E depicts partial secondary structural portions of DVG-546 and DVG-546motif1+: SEQ ID NOS 53 and 65, respectively, in order of appearance. All transfection experiments were independently repeated at least three times. Data correspond to the mean±SEM of all experiments (total n=3-5/group). p<0.01, *p<0.001, ****p<0.0001 by one-way ANOVA with Bonferroni post hoc test. Data are expressed as copy numbers relative to the housekeeping gene GAPDH.

FIG. 9A-FIG. 9D. Recombinant SeV iDVGs with an intact DVG$_{70-114}$ motif preserve their stimulatory activity in the context of infection. (FIG. 9A) Schematic of the recombinant SeV DVG generation system. BSR-T7 cells were infected with partially inactivated SeV 52 and transfected with a plasmid encoding either DVG-324 or DVG-354. Cells and supernatants were collected 48 h later and inoculated into 10-day-old embryonated chicken eggs. SeV containing rDVGs was collected from the allantoic fluid. T7 pro, T7 promoter sequence; Riboz., ribozyme; T7 term, T7 polymerase terminator sequence. (FIG. 9B) LL-CMK2 cells were infected with virus rDVG-324 or rDVG-354 at an MOI of 5 TCID50/cell and analyzed at 6 h postinfection by RT-qPCR for the expression of IFN-β1, IFIT1, and SeV NP mRNA. The data are the average of three independent experiments. *, P<0.05; , P<0.01; *, P<0.001; ****, P<0.0001; ns, nonsignificant (one-wayANOVA with Bonferroni's post hoc test and two-tailed t test in DVG RNA quantification). Data are expressed as the copy number relative to that of the housekeeping gene for GAPDH. (FIG. 9C and FIG. 9D) LL-CMK2 cells were infected with SeV LD at an MOI of 1.5 TCID50/cell and transfected 24 later with 4.15 pmol of DVG-268 or DVG-268$_{Δ70-114}$ RNA or left untreated (NT). Expression of SeV NP and SeV (P/V) (FIG. 9C) and antiviral genes (FIG. 9D) was measured at 6 h post transfection. The data are the average of three independent experiments. *, P<0.05; , P<0.01; *, P<0.001; ****, P<0.0001; ns, nonsignificant (one-way ANOVA with Bonferroni's post hoc test). Data are expressed as the copy number relative to that of the housekeeping gene for GAPDH.

(FIG. 10A) Illustration of DVG-324 and the related 3' complementary sequence deletion mutant (DVG-324NC). The relative position of immunostimulatory motif DVG$_{70-114}$ is highlighted in a grey square. Length of the deletion (dashed line is indicated. (FIG. 10B) Expression of IFNB1 and IFIT1 mRNA by RT-qPCR of LLC-MK2 cells transfected for 6 h with 4.15 pmol DVG-324, DVG-324NC or DVG-546. (FIG. 10C) Folding prediction for DVG-324NC lacking the 70-114 motif (DVG-324NC$_{Δ70-114}$), the parental DVG-324NC, and DVG-324NC$_{Δ5-51}$. Motif DVG70-114 and Motif DVG5-51 are indicated. FIG. 10C discloses SEQ ID NOS 6, 20 and 66, respectively, in order of appearance. (FIG. 10D) Expression of IFNB1 mRNA by RT-qPCR in LLC-MK2 cells transfected for 6 h with 4.15 pmol of the indicated ivtDVG. (FIG. 10E) Illustration of DVG$_{5-51}$ stem-loop motif (SEQ ID NO: 67) and its relative position on the DVG-324NC construct. (FIG. 10F) Expression of IFNB1 mRNA by RT-qPCR of LLC-MK2 cells transfected for 6 h with 4.15 pmol of the indicated ivtDVG. (FIG. 10G) Folding predictions of DVG-324NC motif1+ compared to DVG-324NC. FIG. 10G discloses SEQ ID NOS 1 and 2, respectively, in order of appearance. (FIG. 10H) Expression of IFNB1 mRNA by RT-qPCR of LLC-MK2 cells transfected for 6 h with 4.15 pmol of ivtDVG illustrated in (FIG. 10F). All transfection experiments were independently repeated for at least three times. Data correspond to the mean±SEM of all experiments (total n=3-5/group). *p<0.05, p<0.01, *p<0.001, ****p<0.0001 by one-way ANOVA with Bonferroni post hoc test. Data are expressed as copy numbers relative to the housekeeping gene GAPDH. ns=non-significant.

(FIG. 11A) Folding predictions of HCV X-region (SEQ ID NO: 17), X-region_DVG$_{70-114}$ (SEQ ID NO: 18) and X-region_DVG$_{5-51}$. Motif DVG$_{70-114}$ (SEQ ID NO: 19) is ballooned in the middle figure and motif DVG$_{5-51}$ is ballooned in figure on the right. (FIG. 11B) Expression of IFNB1 and IFIT1 mRNA measured by RT-qPCR of LLC-MK2 cells transfected for 6 h with 4.15 pmol gel purified X-region, X-region DVG$_{70-114}$ and X-region_DVG$_{5-51}$ ivtDVGs. Data correspond to the mean±SEM of all experiments (total n=3-5/group). *p<0.05, **p<0.01 by one-way ANOVA with Bonferroni post hoc test. Data are expressed as copy numbers relative to the housekeeping genes GAPDH. ns=non-significant.

FIG. 12. DVG derived ivtRNAs induced equivalent level of antiviral responses compared to known viral RIG-I ligands.

FIG. 13A-FIG. 13E. DVG$_{70-114}$ motif strongly stimulates RLR signaling. (FIG. 13A) Expression of Ifnb mRNA determined by RT-qPCR from WT, Mavs$^{-/-}$, and Ddx58$^{-/-}$ (RIG-I$^{-/-}$) MEFs transfected for 6 h with 4.15 pmol DVG-ivtDVG variants. (FIG. 13B) Expression of IFNB1 mRNA by RT-qPCR of LLC-MK2 cells transfected for 6 h with DVG-derived ivtDVGs untreated or treated with alkaline phosphatase (AP). (FIG. 13C) Expression of IFNB1 mRNA by RT-qPCR of LLC-MK2 cells transfected for 6 h with 4.15 pmol DVG-268 ivtDVGs not treated (NT) or treated with RNase A, RNase V1, RNase A/V1, or mock transfected. (FIG. 13D and FIG. 13E) EMSA of DVG-268 and DVG-268$_{Δ70-114}$ RNA to increasing doses of RIG-I deltaCARD in the absence (FIG. 13D) or presence (FIG. 13E) of 1 μM ATP. All experiments in FIG. 13A-FIG. 13E were independently repeated at least three times. Each RT-qPCR assay was performed in triplicates. Data correspond to the average of all experiments (total n>3/group). p<0.001, *p<0.001, ****p<0.0001 by two-way ANOVA (FIG. 13A) or one-way ANOVA (FIG. 13B and FIG. 13C) with Bonferroni post hoc test. RT-qPCR data are expressed as copy numbers relative to the housekeeping genes GAPDH and/or ACTB (for LL-CMK2 cells) and Rps11 for MEFs.

FIG. 15A-FIG. 15C. DVG$_{70-114}$ immunostimulatory activity in vivo. (FIG. 15A) Procedure for testing the activity of DVG$_{70-114}$ in vivo. C57BL6 mice were treated intranasally (i.n.) with 30 ul of PBS (mock) or 4 μg of polyI:C, DVG-324NC or DVG-324NCΔ70-114. (FIG. 15B) Expression of the antiviral gene Mx1 in whole lung homogenates collected 6 hpi. (FIG. 15C) RNA in situ hybridization on lungs extracted 6 h after inoculation of DVG-324NC. Green dots represent DVG-324NC bound by labeled probes.

FIG. 16. SEQ ID NO:1. DVG$_{70-114}$ Motif (45nt).

FIG. 17. SEQ ID NO:2. An exemplary modifying mutation: DVG$_{70-114}$ Motif1+ (47nt, from 5' to 3', additional nucleotides underlined).

FIG. 18. SEQ ID NO:3. An exemplary mutation that significantly reduces the motif activity: DVG$_{70-114}$ U106G (45nt, from 5'-3', mutated nucleotide is underlined).

FIG. 19. SEQ ID NO:4. An exemplary mutation that significantly reduces the motif activity: DVG$_{70-114}$ C97G (45nt, from 5'-3', mutated nucleotide is underlined).

FIG. 20. SEQ ID NO:5. An exemplary modifying mutation: DVG$_{70-114}$ A89U (45nt, from 5'-3', mutated nucleotide is underlined).

FIG. 21. Primers used in mutagenesis (SEQ ID NOS 25-46, respectively, in order of appearance).

FIG. 22. Primers used in quantitative PCR assays (SEQ ID NOS 68-87, respectively, in order of appearance).

FIG. 25 depicts a partial secondary structural portion of DVG-268: SEQ ID NO: 58.

FIG. 27. Motif 70-114 (SEQ ID NO: 23) (along with 5' and 3' overhang) induced strong protection to infectious challenge with single immunization. Level of IAV HA specific IgG, IgG1 and IgG2b antibodies in the serum were measured by ELISA. *<0.0001 and *<0.001 by One way-ANOVA with Bonferroni pos-hoc test. Ns=non-significant.

FIG. 28. Motif 70-114 induced strong protection to infectious challenge with single immunization. Expression of IAV NP mRNA in whole lung homogenate was analyzed by RT-qPCR. Data are shown as mRNA copy number relative to house keeping gene Rps11 and Gapdh. ***<0.001 by One way-ANOVA with Bonferroni pos-hoc test.

FIG. 31. DVG-324 inserted into MERS DNA vaccine enhanced immunostimulatory activity. MERS specific IFN-gamma ELISpot in C57BL/6.

FIG. 32. DVG70-114 motif alone conserve strong immunostimulatory activity in the presence of a 5' end overhang. 3'-overhang: DVG70-114 motif (SEQ ID NO: 22). 5' and 3'-overhang: DVG70-114 motif (SEQ ID NO: 23). Blunt: DVG70-114 motif alone (SEQ ID NO: 1). DVG-268:DDO. Mock: Untreated control.

DETAILED DESCRIPTION

Figure 3A:
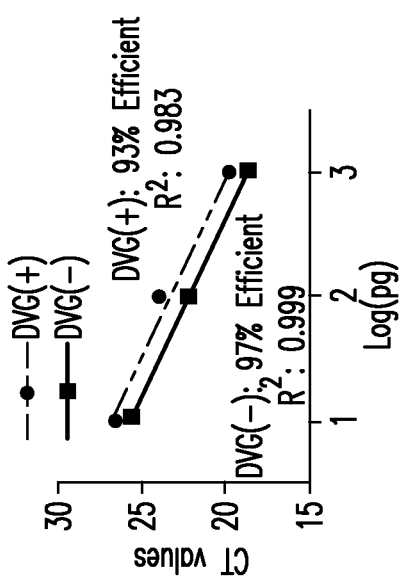
FIG. 3A-FIG. 3D. Production of DVG(+) during DVG replication closely matches induction of IFNB1.

The present disclosure is based, at least in part, on the discovery of an RNA motif (DVG$_{70-114}$) that is capable of eliciting a strong immune response. In certain embodiments, the RNA motif, DVG$_{70-114}$, facilitates recognition of viral RNA by RIG-I like receptors (RLRs) and/or Toll-like receptors (TLRs) and promotes the onset of the antiviral response. In certain embodiments, this RNA motif can be modified for stronger immunostimulatory activity and can be engineered into immunologically inert or weak RNA to enhance the RNA immunostimulatory potential. For example, the motif can be stabilized by modifying its sequence or using chemical molecules. In certain embodiments, the RNA motif DVG$_{70-114}$ or modified motif forms can be used as immunostimulants in vivo and used as adjuvants along with vaccines, antigens, and other substances to enhance host immune responses. Thus, in certain embodiments, DVG$_{70-114}$ or its modified motif forms represent novel PAMP enhancer motifs.

As described herein, the DVG$_{70-114}$ motif has been shown to confer strong immunostimulatory activity to inert RNA molecules (e.g., non-immunostimulatory virus molecules, non-viral RNA molecules, and the like). In certain embodiments, the immunostimulatory activity can be conferred upon an inert RNA molecule by cloning the motif, or modified forms of the motif, into the sequence of a naturally-occurring immunologically inert RNA molecule. For example, but not by way of limitation, the immunostimulatory activity of these motifs can be transferred to a naturally-occurring inert RNA molecule by cloning the motifs into the X-region of the hepatitis C virus (HCV) (a non-immunostimulatory small RNA derived from the HCV viral genome).

In certain embodiments, the immunostimulatory activity can be conferred upon any RNA molecule that contains or is modified to contain 5'triphosphates or phosphate analogs by cloning the motif into the sequence of the RNA molecule.

In certain embodiments, these motifs can also be attached to antibodies allowing for targeted delivery of the motifs allowing for localized immunostimulation. For example, but not by way of limitation, these motifs can be attached to an antibody directed to an antigen found on a specific tumor cell. As such, in certain embodiments these motifs enhance the host's immune response to the tumor cells. In certain embodiments, these motifs can be also targeted to antigen presenting cells, such as dendritic cells and macrophages, to trigger their maturation and activity. In certain embodiments these motifs are targeted to a specific organ to generate a localized inflammatory response, for example, but not limited to the lung, liver, kidney, heart, penis, uterus, eye, brain, intestine, skin, joints, or bone.

In certain embodiments these motifs can be conjugated with antigens and/or natural or synthetic nanoparticles, for example, but not limited to, liposomes, virus like particles, polymers, etc. for the development of novel vaccines. In certain embodiments, these motifs act as an immune-potentiator. In certain embodiments, motifs can be also conjugated to (or combined with) adjuvants to modify or improve their activity. For example, the motifs can be combined or conjugated with alum to promote the generation of a Th1-biased immune response. In certain embodiments the combination of these motifs with adjuvant emulsions, for example, but not limited to MF59.

In certain embodiments these motifs can be encapsulated with natural or synthetic nanoparticles, for example, but not limited to, liposomes, virus like particles, polymers, etc. for the development of novel vaccines.

In certain embodiments, the positive (+)RNA strands of SeV copy-back DVGs are associated with strong stimulation of the antiviral response. In certain embodiments, an increased ratio of (+)/(−)DVG strands positively correlated with the induction of IFNB1 expressing in vitro, and the accumulation of (+)RNA strands of SeV is positively associated with the induction of antiviral responses in cells infected with SeV. As such, the (+)RNA strands or their derivatives of SeV can also be used, in certain embodiments, as immunostimulants in vivo.

DEFINITIONS

According to the present disclosure, a "subject" or a "patient" is a human or non-human animal. Although the animal subject is preferably a human, the compounds and compositions of the invention have application in veterinary medicine as well, e.g., for the treatment of domesticated species such as canine, feline, murine, and various other pets; farm animal species such as bovine, equine, ovine, caprine, porcine, etc.; and wild animals, e.g., in the wild or in a zoological garden, such as non-human primates.

"Adjuvant" means any substance that increases the humoral or cellular immune response to an antigen. Adjuvants are generally used to accomplish two objectives: they slow the release of antigens from the injection site, and they stimulate the immune system.

"Antibody" refers to an immunoglobulin molecule that can bind to a specific antigen as the result of an immune response to that antigen. Immunoglobulins are serum proteins composed of "light" and "heavy" polypeptide chains having "constant" and "variable" regions and are divided into classes (e.g., IgA, IgD, IgE, IgG, and IgM) based on the composition of the constant regions.

"Antigen" or "immunogen" refers to any substance that stimulates an immune response. The term includes killed, inactivated, attenuated, or modified live bacteria, viruses, fungi or parasites or parasite eggs, etc. The term antigen also includes polynucleotides, polypeptides, recombinant proteins, synthetic peptides, protein extract, cells (including tumor cells), tissues, polysaccharides, or lipids, or fragments thereof, individually or in any combination thereof. The term antigen also includes antibodies, such as anti-idiotype antibodies or fragments thereof, and to synthetic peptide mimotopes that can mimic an antigen or antigenic determinant (epitope).

"RNA motif" as used herein includes, but is not limited to, the isolated RNA molecule $DVG_{70-114}$ (SEQ ID NO:1) or modified variants (e.g., SEQ ID NO:2, SEQ ID NO:5, SEQ ID NO:23) that signal for the activation of transcription factors that trigger the expression of antiviral and/or pro-inflammatory molecules.

"Modified variants", "modified RNA motif forms", or "modified motif forms" include mutant $DVG_{70-114}$ forms that results in enhancement of $DVG_{70-114}$ signaling. In certain embodiments, these modified variants are generated by the substitution, deletion, or addition of a nucleotide(s). For example, a modified motif form can include an additional A-U base pair in the long stem region of $DVG_{70-114}$ creating a 47 nucleotide stabilized variant (e.g. SEQ ID NO:2). As another example, a modified motif form can include additional nucleotides can be added either to the 5' or the 5' and 3' end of the $DVG_{70-114}$ (e.g., SEQ ID NO: 23).

"Immune response" in a subject refers to the development of a humoral immune response, a cellular immune response, or a humoral and a cellular immune response to an antigen. Immune responses can usually be determined using standard immunoassays and neutralization assays, which are known in the art.

"Cellular immune response" or "cell mediated immune response" is one mediated by T-lymphocytes or other white blood cells or both, and includes the production of cytokines, chemokines and similar molecules produced by activated T-cells, white blood cells, or both.

"Humoral immune response" refers to one that is mediated by antibodies.

"Immunologically protective amount" or "immunologically effective amount" or "effective amount to produce an immune response" of an antigen is an amount effective to induce an immunogenic response in the recipient. The immunogenic response can be sufficient for diagnostic purposes or other testing, or can be adequate to prevent signs or symptoms of disease, including adverse health effects or complications thereof, caused by infection with a disease agent. Either humoral immunity or cell-mediated immunity or both can be induced. The immunogenic response of an animal to an immunogenic composition can be evaluated, e.g., indirectly through measurement of antibody titers, lymphocyte proliferation assays, or directly through monitoring signs and symptoms after challenge with wild type strain, whereas the protective immunity conferred by a vaccine can be evaluated by measuring, e.g., reduction in clinical signs such as mortality, morbidity, temperature number, overall physical condition, and overall health and performance of the subject. The immune response can comprise, without limitation, induction of cellular and/or humoral immunity.

"Immunogenic" means evoking an immune or antigenic response. Thus an immunogenic composition would be any composition that induces an immune response.

"Immunostimulatory molecule" refers to a molecule that generates an immune response.

"Treatment," "treating," and the like refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a subject or patient and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

"Therapeutically effective amount" refers to an amount of an antigen or vaccine that would induce an immune response in a subject receiving the antigen or vaccine which is adequate to prevent or reduce signs or symptoms of disease, including adverse health effects or complications thereof, caused by infection with a pathogen, such as a virus or a bacterium. Humoral immunity or cell-mediated immunity or both humoral and cell-mediated immunity can be induced. The immunogenic response of a subject to a vaccine can be evaluated, e.g., indirectly through measurement of antibody titers, lymphocyte proliferation assays, or directly through monitoring signs and symptoms after challenge with wild type strain. The protective immunity conferred by a vaccine can be evaluated by measuring, e.g., reduction in clinical signs such as mortality, morbidity, temperature, overall physical condition, and overall health of the subject. The amount of a vaccine that is therapeutically effective can vary depending on the particular adjuvant used, the particular antigen used, or the condition of the subject, and can be determined by one skilled in the art.

"Pharmaceutical composition" and "pharmaceutical formulation," as used herein, refer to a composition which is in such form as to permit the biological activity of an active ingredient contained therein to be effective, and which contains no additional components which are unacceptably toxic to a patient to which the formulation would be administered.

"Pharmaceutically acceptable," as used herein, e.g., with respect to a "pharmaceutically acceptable carrier," refers to the property of being nontoxic to a subject. A pharmaceutically acceptable ingredient in a pharmaceutical formulation can be an ingredient other than an active ingredient that is nontoxic. A pharmaceutically acceptable carrier can include a buffer, excipient, stabilizer, and/or preservative.

"Lipids" refers to any of a group of organic compounds, including the fats, oils, waxes, sterols, and triglycerides, which are insoluble in water but soluble in nonpolar organic solvents, are oily to the touch, and together with carbohydrates and proteins constitute the principal structural material of living cells.

"Liposome" refers to a microscopic spherical particle formed by a lipid bilayer enclosing an aqueous compartment, used medicinally to carry a drug, antigen, vaccine, enzyme, or another substance to targeted cells in the body.

"Vaccine" refers to a composition that includes an antigen, as defined herein. Administration of the vaccine to a subject results in an immune response, generally against one or more specific diseases. The amount of a vaccine that is therapeutically effective can vary depending on the particular antigen used, or the condition of the subject, and can be determined by one skilled in the art. A vaccine can comprise a live attenuated virus in a suitable pharmaceutically, or physiologically acceptable carrier, such as isotonic saline or isotonic salts solution. The appropriate carrier will be evident to those skilled in the art and will depend in large part upon the route of administration. Alternatively, vaccines composed of polynucleotide molecules desirably contain optional polynucleotide facilitating agents or "co-agents", such as a local anesthetic, a peptide, a lipid including cationic lipids, a liposome or lipidic particle, a polycation such as polylysine, a branched, three-dimensional polycation such as a dendrimer, a carbohydrate, a cationic amphiphile, a detergent, a benzylammonium surfactant, or another compound that facilitates polynucleotide transfer to cells. Non-exclusive examples of such facilitating agents or co-agents useful in this disclosure are described in U.S. Pat. Nos. 5,593,972; 5,703,055; 5,739,118; 5,837,533; International Patent Application No. WO96/10038, published Apr. 4, 1996; and International Patent Application No WO94/16737, published Aug. 8, 1994, which are each incorporated herein by reference.

"Cancer" includes, for example, skin cancers (melanoma and squamous cell carcinoma), pancreatic cancer, kidney cancer, e.g., renal cell carcinoma (RCC), urogenital cancer, e.g., urothelial carcinomas in urinary bladder, kidney, pelvic and ureter, melanoma, prostate carcinoma, lung carcinomas (non-small cell carcinoma, small cell carcinoma, neuroendocrine carcinoma and carcinoid tumor), breast carcinomas (ductal carcinoma, lobular carcinoma and mixed ductal and lobular carcinoma), thyroid carcinomas (papillary thyroid carcinoma, follicular carcinoma and medullary carcinoma), brain cancers (meningioma, astrocytoma, glioblastoma, cerebellum tumors, medulloblastoma, ependymoma), ovarian carcinomas (serous, mucinous and endometrioid types), cervical cancers (squamous cell carcinoma in situ, invasive squamous cell carcinoma and endocervical adenocarcinoma), uterine endometrial carcinoma (endometrioid, serous and mucinous types), primary peritoneal carcinoma, mesothelioma (pleura and peritoneum), eye cancer (retinoblastoma), muscle (rhapdosarcoma and leiomyosarcoma), lymphomas, esophageal cancer (adenocarcinoma and squamous cell carcinoma), gastric cancers (gastric adenocarcinoma and gastrointestinal stroma tumor), liver cancers (hepatocellular carcinoma and bile duct cancer), small intestinal tumors (small intestinal stromal tumor and carcinoid tumor) colon cancer (adenocarcinoma of the colon, colon high grade dysplasia and colon carcinoid tumor), testicular cancer, and adrenal carcinoma.

A "tumor" includes any tumor resulting or associated with from any of the above cancers.

RNA Motifs

The presently disclosed subject matter provides, in certain embodiments, for immunostimulatory RNA motifs. In certain embodiments, the RNA motifs are used as adjuvants or immunostimulatory agents to activate antigen presenting cells, such as dendritic cells, or structural cells, such as fibroblasts and muscle, to trigger cytokine expression and enhance host immune responses to an antigen. In certain embodiments, the RNA motifs described herein have increased immunostimulatory activity as compared to DVG particles or DVG-derived RNA molecules containing larger portions of the DVG sequence. For example, but not by way of limitation, the motifs described herein can trigger an innate immune response in any cell. This is a major advantage of triggering the RLRs (e.g., RIG-I and MDA5) over Toll-like receptors (TLRs), as RLRs are expressed in all cells, while TLRs are mostly restricted to antigen presenting cells.

The stem region of motif DVG70-114 (nucleotides 75-82 and 100-109 of DVG-268) provides stability to the motif structure and can be modified to enhance stability by, for example, engineering additional base pairs, or replacing weak interactions (A:T) with stronger ones (C:G). Residues at the tip or bulk of the molecules could also be modified to enhance stability and binding to innate immune receptors. In addition, alterations in or to the sequence of the motif that maintain its structure can be introduce to maximize immune stimulation. Immunostimulatory activity can be measured by the methods described herein (e.g., in the Examples), and methods known in the art.

In certain embodiments, the RNA motif is $DVG_{70-114}$. In certain embodiments, the RNA motif is a modified variant of $DVG_{70-114}$. In certain embodiments, the modified RNA motifs can contain nucleotide substitutions, deletions, inversions and insertions of the $DVG_{70-114}$ motif, but still retain immunostimulatory activity. In certain embodiments, the modified RNA motif includes a $DVG_{70-114}$ with an elongated long stem region, but which still retain immunostimulatory activity. In certain embodiments, the modified RNA motif includes an additional A-U pair assertion into the $DVG_{70-114}$ long stem region (e.g., SEQ ID NO:2). In certain embodiments, the modified RNA motif includes a C-G insertion. In certain embodiments, the modified RNA motif includes a point mutation that maintains or enhances activity (e.g., SEQ ID NO:5).

In certain embodiments, the modified RNA motif can also be stabilized by adding an overhang (i.e., additional nucleotide residues) to either the 5' or 5' and 3' end of the DVG70-114 motif. In certain embodiments, either the 5' or 3' overhang are complementary. In certain embodiments, at least a portion of the 5' and 3' overhang extend the stem portion of the DVG70-114 motif. In certain embodiments, at least a portion of the 5' and 3' overhang is complementary. In certain embodiments, the additional nucleotides can be from the parent DVG-268 sequence (e.g., SEQ ID NO: 22). In certain embodiments, the additional nucleotides are not from the parent DVG-268 sequence (e.g., SEQ ID NO: 24). In certain embodiments, the additional nucleotides of one overhang can be from the parent DVG-268 sequence while the additional nucleotides of the other overhang are not (e.g., SEQ ID NO: 23).

In certain embodiments, 5 to 15 nucleotides can be added to the 5' end of the DVG70-114 motif. In certain embodiments, 5 to 10, 10 to 15, or 10 to 20 nucleotides can be added to the 5' end of the DVG70-114 motif. In certain embodiments, 5, 6, 7, 8, 9, 10, 11, 12, 13, 14, 15, 16, 17, 18, 19, or 20 nucleotides can be added to the 5' end of the DVG70-114 motif. In certain embodiment, 5 nucleotides can be added to the 5' end of the DVG70-114 motif (e.g., SEQ ID NO:24). In certain embodiments, 5 to 15 nucleotides can be added to the 3' end of the DVG70-114 motif. In certain embodiments, 5 to 10, 10 to 15, or 10 to 20 nucleotides can be added to the 3' end of the DVG70-114 motif. In certain embodiments, 5, 6, 7, 8, 9, 10, 11, 12, 13, 14, 15, 16, 17, 18, 19, or 20 nucleotides can be added to the 3' end of the DVG70-114 motif. In certain embodiment, 15 nucleotides can be added to the 3' end of the of the $DVG_{70-114}$ motif. In certain embodiment, 5 nucleotides can be added to the 5' end and 15 nucleotides can be added to the 3' end of the DVG70-114 motif (SEQ ID NO:23). In certain embodiments, the 5' and 3' overhang has 1, 2, 3, 4, 5, 6, 7, 8, 9, 10, 11, 12, 13, 14, or 15 complementary pairs. In certain embodiments, the 5' and 3' overhang has about 2 to about 5 complementary pairs. In certain embodiments, the 5' and 3' overhang has about 3 complementary pairs (e.g., SEQ ID NO:23).

In certain embodiments, the modified RNA motif can also be stabilized by chemical modifications. In certain embodiments, the modified RNA motif can also be modulated in a negative way with point mutations.

In certain embodiments, the motif can be in vitro transcribed or made synthetically and used as an RLR ligand in vitro or in vivo.

TABLE 1

Table of Sequences.

| Descriptor | Sequence |
|---|---|
| SEQ ID NO: 1 DVG70-114 Motif | UUGUCAUAUGGAUAAGUCCAAGACUAUCUUUA UCUAUGUCCACAA |
| SEQ ID NO: 2 DVG70-114 Motif1+ | UUGUCAUAU<u>A</u>GGAUAAGUCCAAGACUAUCUUU AUCU<u>U</u>AUGUCCACAA |
| SEQ ID NO: 3 DVG70-114 U106G | UUGUCAUAUGGAUAAGUCCAAGACUAUCUUUA UCUA<u>G</u>GUCCACA |
| SEQ ID NO: 4 DVG70-114 C97G | UUGUCAUAUGGAUAAGUCCAAGACUAU<u>G</u>UUUA UCUAUGUCCACAA |
| SEQ ID NO: 5 DVG70-114 A89U | UUGUCAUAUGGAUAAGUCC<u>U</u>AGACUAUCUUUA UCUAUGUCCACAA |
| SEQ ID NO: 6 DVG-324NC | ACCAGACAAG AGUUUAAGAG AUAUGUAUCC UUUUAAAUUU UCUUGUCUUC UUGUAAGUUU UUCUUGCUAU UGUCAUAUGG AUAAGUCCAA GACUAUCUUU AUCUAUGUCC ACAAGAUUGG UAACUGGGUC AUUCCCUGAC CAGAAGUUUG AAGCAAGACU UCAAUUAGGA AUAGUUUCAU UAUCAUCCCG UGAGAUCAGG AACCUGAGGG UUAUCACAAA GGUAC |
| SEQ ID NO: 7 DVG-546 | ACCAGACAAG AGUUUAAGAG AUAUGUAUCC UUUUAAAUUU UCUUGUCUUC UUGUAAGUUU UUCUUGCUAU UGUCAUAUGG AUAAGUCCAA GACUAUCUUU AUCUAUGUCC ACAAGAUUGG UAACUGGGUC AUUCCCUGAC CAGAAGUUUG AAGCAAGACU UCAAUUAGGA AUAGUUUCAU UAUCAUCCCG UGAGAUCAGG AACCUGAGGG UUAUCACAAA AACUUUAUUA GACAGGUUUG AGGAUAUUAU ACAUAGUAUA ACGUAUAGAU UCCUCACCAA AGAAAUAAAG AUCUUGAUGA AGAUUUUAGG GGCAGUCAAG AUGUUCGGGG CCAGGCAAAA UGAAUACACG ACCGUGAUUG AUGAUGGAUC ACUGGGUGAU AUCGAGCCAU AUGACAGCUC GUAAUAAUUA GUCCCUAUCG UGCAGAACGA UCGAAGCUCC GCGGUACCUG GAAGUCUUGG ACUUAUCCAU AUGACAAUAG UAAGAAAAAC UUACAAGAAG ACAAGAAAAU UUAAUAGGAU ACAUAUCUCU UAAACUCUUG UCUGGU |
| SEQ ID NO: 8 DVG-324 | ACCAGACAAG AGUUUAAGAG AUAUGUAUCC UUUUAAAUUU UCUUGUCUUC UUGUAAGUUU UUCUUGCUAU UGUCAUAUGG AUAAGUCCAA GACUAUCUUU AUCUAUGUCC ACAAGAUUGG UAACUGGGUC AUUCCCUGAC CAGAAGUUUG AAGCAAGACU UCAAUUAGGA AUAGUUUCAU UAUCAUCCCG UGAGAUCAGG AACCUGAGGG UUAUCACAAA GGUACCUGGA AGUCUUGGAC UUAUCCAUAU GACAAUAGUA AGAAAACUU ACAAGAAGAC AAGAAAAUUU AAUAGGAUAC AUAUCUCUUA AACUCUUGUC UGGU |
| SEQ ID NO: 9 DVG-268 | ACCAGACAAG AGUUUAAGAG AUAUGUAUCC UUUUAAAUUU UCUUGUCUUC UUGUAAGUUU UUCUUGCUAU UGUCAUAUGG AUAAGUCCAA GACUAUCUUU AUCUAUGUCC ACAAGAUUGG UAACUGGGUC AUUCCCUGAC CAGAAGUUUG AAGCAAGACU UCCCGGUACC UGGAAGUCUU GGACUUAUCC AUAUGACAAU AGUAAGAAAA ACUUACAAGA AGACAAGAAA AUUUAAUAGG AUACAUAUCU CUUAAACUCU UGUCUGGU |

TABLE 1-continued

Table of Sequences.

| Descriptor | Sequence |
|---|---|
| SEQ ID NO: 10 DVG-200 | ACCAGACAAG AGUUUAAGAG AUAUGUAUCC UUUUAAAUUU UCUUGUCUUC UUGUAAGUUU UUCUUGCUAU UGUCAUAUGG AUAAGUCCAA GACUAUGGUA CCUGGAAGUC UUGGACUUAU CCAUAUGACA AUAGUAAGAA AAACUUACAA GAAGACAAGA AAAUUUAAUA GGAUACAUAU CUCUUAAACU CUUGUCUGGU |
| SEQ ID NO: 11 DVG-IS | CCUUUAUCUA UGUCCACAAG AUUGGUAACU GGGUCAUUCC CUGACCAGAA GUUUGAAGCA AGACUUCAAU UAGGAAUAGU UUCAUUAUCA UCCCGUGAGA UCAGGAACCU GAGGGUUAUC ACAAAACUU UAUUAGACAG GUUUGAGGAU AUUAUACAUA GUAUAACGUA UAGAUUCCUC ACCAAAGAAA UAAGAUUUU GAUGAAGAUU UUAGGGGCAG UCAAGAUGUU CGGGGCCAGG CAAAAUGAAU ACACGACCGU GAUUGAUGAU GGAUCACUGG GUGAUAUCGA GCCAUAUGAC AGCUCGUAAU AAUUAGUCCC UAUCGUGCAG AACGAUCGAA GCUCCGCGGU ACC |
| SEQ ID NO: 12 DVG-268 U106G | ACCAGACAAG AGUUUAAGAG AUAUGUAUCC UUUUAAAUUU UCUUGUCUUC UUGUAAGUUU UUCUUGCUAU UGUCAUAUGG AUAAGUCCAA GACUAUCUUU AUCUAGGUCC ACAAGAUUGG UAACUGGGUC AUUCCUGAC CAGAAGUUUG AAGCAAGACU UCCCGGUACC UGGAAGUCUU GGACUUAUCC AUAUGACAAU AGUAAGAAAA ACUUACAAGA AGACAAGAAA AUUUAAUAGG AUACAUAUCU CUUAAACUCU UGUCUGGU |
| SEQ ID NO: 13 DVG-268 A89U | ACCAGACAAG AGUUUAAGAG AUAUGUAUCC UUUUAAAUUU UCUUGUCUUC UUGUAAGUUU UUCUUGCUAU UGUCAUAUGG AUAAGUCCUA GACUAUCUUU AUCUAUGUCC ACAAGAUUGG UAACUGGGUC AUUCCUGAC CAGAAGUUUG AAGCAAGACU UCCCGGUACC UGGAAGUCUU GGACUUAUCC AUAUGACAAU AGUAAGAAAA ACUUACAAGA AGACAAGAAA AUUUAAUAGG AUACAUAUCU CUUAAACUCU UGUCUGGU |
| SEQ ID NO: 14 DVG-268 C97G | ACCAGACAAG AGUUUAAGAG AUAUGUAUCC UUUUAAAUUU UCUUGUCUUC UUGUAAGUUU UUCUUGCUAU UGUCAUAUGG AUAAGUCCAA GACUAUGUUU AUCUAUGUCC ACAAGAUUGG UAACUGGGUC AUUCCUGAC CAGAAGUUUG AAGCAAGACU UCCCGGUACC UGGAAGUCUU GGACUUAUCC AUAUGACAAU AGUAAGAAAA ACUUACAAGA AGACAAGAAA AUUUAAUAGG AUACAUAUCU CUUAAACUCU UGUCUGGU |
| SEQ ID NO: 15 DVG-546Δ70-114 | ACCAGACAAG AGUUUAAGAG AUAUGUAUCC UUUUAAAUUU UCUUGUCUUC UUGUAAGUUU UUCUUGCUAG AUUGGUAACU GGGUCAUUCC CUGACCAGAA GUUUGAAGCA AGACUUCAAU UAGGAAUAGU UUCAUUAUCA UCCCGUGAGA UCAGGAACCU GAGGGUUAUC ACAAAACUU UAUUAGACAG GUUUGAGGAU AUUAUACAUA GUAUAACGUA UAGAUUCCUC ACCAAAGAAA UAAGAUUUU GAUGAAGAUU UUAGGGGCAG UCAAGAUGUU CGGGGCCAGG CAAAAUGAAU ACACGACCGU GAUUGAUGAU GGAUCACUGG GUGAUAUCGA GCCAUAUGAC AGCUCGUAAU AAUUAGUCCC UAUCGUGCAG AACGAUCGAA GCUCCGCGGU ACCUGGAAGU CUUGGACUUA UCCAUAUGAC AAUAGUAAGA AAAACUUACA AGAAGACAAG AAAAUUUAAU AGGAUACAUA UCUCUUAAAC UCUUGUCUGG U |
| SEQ ID NO: 16 DVG-546motif 1+ | ACCAGACAAG AGUUUAAGAG AUAUGUAUCC UUUUAAAUUU UCUUGUCUUC UUGUAAGUUU UUCUUGCUAU UGUCAUAUAG GAUAAGUCCA AGACUAUCUU UAUCUUAUGU CCACAAGAUU GGUAACUGGG UCAUUCCCUG ACCAGAAGUU UGAAGCAAGA CUUCAAUUAG GAAUAGUUUC AUUAUCAUCC CGUGAGAUCA GGAACCUGAG GGUUAUCACA AAACUUUAU UAGACAGGUU UGAGGAUAUU AUACAUAGUA UAACGUAUAG AUUCCUCACC AAAGAAAUAA GAUCUUGAU GAAGAUUUUA GGGGCAGUCA AGAUGUUCGG GGCCAGGCAA AUGAAUACA CGACCGUGAU UGAUGAUGGA UCACUGGGUG AUAUCGAGCC AUAUGACAGC UCGUAAUAAU UAGUCCCUAU CGUGCAGAAC GAUCGAAGCU CCGCGGUACC UGGAAGUCUU GGACUUAUCC AUAUGACAAU AGUAAGAAAA ACUUACAAGA AGACAAGAAA AUUUAAUAGG AUACAUAUCU CUUAAACUCU UGUCUGGU |
| SEQ ID NO: 17 X-region (full length 98nt) | GGUGGCUCCA UCUUAGCCCU AGUCACGGCU AGCUGUGAAA GGUCCGUGAG CCGCUUGACU GCAGAGAGUG CUGAUACUGG CCUCUCUGCA GAUCAAGU |
| SEQ ID NO: 18 PLUS DVG70-114 | GGUGGCUCCA UCUUAGCCCU AGUCACGGCU AGCUGUGAAA GGUCCGUGAG CCGCUUGACU GCAGAGAGUG CUGAUACUGG CCUCUCUGCA GAUCAAGUUU GUCAUAUGGA UAAGUCCAAG ACUAUCUUUA UCUAUGUCCA CAA |
| SEQ ID NO: 19 PLUS DVG5-51 | GGUGGCUCCA UCUUAGCCCU AGUCACGGCU AGCUGUGAAA GGUCCGUGAG CCGCUUGACU GCAGAGAGUG UGAUACUGGC CUCUCUGCAG AUCAAGUGAC AAGAGUUUAA GAGAUAUGUA UCCUUUUAAA UUUUCUUGUC UUCU |
| SEQ ID NO: 20 DVG-324NCΔ70-114 | ACCAGACAAG AGUUUAAGAG AUAUGUAUCC UUUUAAAUUU UCUUGUCUUC UUGUAAGUUU UUCUUGCUAG AUUGGUAACU GGGUCAUUCC CUGACCAGAA GUUUGAAGCA AGACUUCAAU UAGGAAUAGU UUCAUUAUCA UCCCGUGAGA UCAGGAACCU GAGGGUUAUC ACAAAGGUAC |
| SEQ ID NO: 21 DVG-268Δ70-114 | ACCAGACAAG AGUUUAAGAG AUAUGUAUCC UUUUAAAUUU UCUUGUCUUC UUGUAAGUUU UUCUUGCUAG AUUGGUAACU GGGUCAUUCC CUGACCAGAA GUUUGAAGCA AGACUUCCCG GAAAAACUUA CAAGAAGACA AGAAAAUUUA AUAGGAUACA UAUCUCUUAA ACUCUUGCU GGU |
| SEQ ID NO: 22 DVG70-114 5p03p10 (3'overhang) | UUGUCAUAUGGAUAAGUCCAAGACUAUCUUUA UCUAUGUCCACAAGAUUGGUAAC |
| SEQ ID NO: 23 DVG70-114 5p5x3p15 (5' and 3' overhang) | CAAGUUUGUCAUAUGGAUAAGUCCAAGACUAU CUUUAUCUAUGUCCACAAGAUUGGUAACUGGG U |
| SEQ ID NO: 24 DVG70-114 (5' overhang) | CAAGUUU GUCAUAUGGA UAAGUCCAAG ACUAUCUUUA UCUAUGUCCA CAA |

Shading denotes the RNA motif, and underlining denotes base modifications.

Delivery of the RNA Motifs

In certain embodiments, delivery of RNA motifs into a subject or cell (e.g., dendritic cell) can be either direct, in which case the subject or cell is directly exposed to the naked nucleic acid, or indirect, in which case, cells are first transformed with the nucleic acids in vitro, then introduced or reintroduced into the patient.

The RNA motifs of the present disclosure can be directly administered in vivo, e.g., combined with an antigen or vaccine to form an adjuvant composition. In certain embodiments, the RNA motif (or motifs) (e.g., SEQ ID NO:1; SEQ ID NO:2; SEQ ID NO:5), or a modified variant of SEQ ID NO:1 having immunostimulatory activity, can be administered in vivo. In certain embodiments, the RNA motif is conjugated to additional nucleotides to impart its immunostimulatory activity. For example, the modified RNA motif can have additional nucleotides at the 5' or 5' and 3' end of the $DVG_{70-114}$ motif as described above (e.g., SEQ ID NO: 23). In certain embodiments, the $DVG_{70-114}$ motif can be conjugated to a natural or synthetic nanoparticles, for example, but not limited to, liposomes, virus like particles, polymers to impart its immunostimulatory activity.

Administered in vivo can be accomplished by any of numerous methods known in the art, e.g., by direct injection of naked RNA. For example, the RNA motif can be injected, aerosolized, electroporated in the skin or muscle, or used intranasally, etc. The RNA motif can also be administered by use of microparticle bombardment (e.g., a gene gun; Biolistic, Dupont), or coating with lipids, encapsulation in liposomes, microparticles, or microcapsules, or by administering them in linkage to a peptide. The nucleic acid-ligand complexes can also be formed in which the ligand comprises a fusogenic viral peptide to disrupt endosomes, allowing the nucleic acid to avoid lysosomal degradation. The RNA motifs can also be stabilized with cationic molecules, e.g., Poly-L Lysine, or attached to nanoparticles for delivery. In certain embodiments, the nanoparticles can also contain one or more antigen. In certain embodiments, the RNA motifs can be conjugated with antigen for delivery. For example, the RNA motif can be conjugated to parasite eggs, proteins, etc. The RNA motifs can also be delivered along with the antigen and an additional immunological adjuvant.

In certain embodiments, motifs can be also conjugated to or combined with adjuvants to modify or improve their activity. Immunological adjuvants include, but are not limited to: aluminum salts (alum), such as aluminum hydroxide, aluminum phosphate, aluminum sulfate, etc.; oil-in-water emulsion formulations (with or without other specific immunostimulating agents such as muramyl peptides (see below) or bacterial cell wall components) (e.g., mineral oil), such as for example MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 100Y microfluidizer (Microfluidics, Newton, Mass.), SAF, containing 10% Squalane, 0.4% Tween 80, 5% pluronic-blocked polymer L121, and thr-MDP either microfluidized into a submicron emulsion or vortexed to generate a larger particle size emulsion, and Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL) (e.g. 3-O-deacylated monophosphoryl lipid A; RIBI ImmunoChem Research, Inc., Hamilton, Mont.), trehalose dimycolate (TDM), and cell wall skeleton (CWS), preferably MPL+CWS (Detox™) (for a further discussion of suitable submicron oil-in-water emulsions for use herein, see e.g., U.S. Pat. No. 6,086,91); saponin adjuvants, such as Quil A, or QS21 (e.g., Stimulon™ (Cambridge Bioscience, Worcester, Mass.)) may be used or particle generated therefrom such as ISCOMs (immunostimulating complexes); Complete Freunds Adjuvant (CFA) and Incomplete Freunds Adjuvant (IFA); cytokines, such as interleukins (IL-1, IL-2, etc.), macrophage colony stimulating factor (M-CSF), tumor necrosis factor (TNF), etc.; detoxified mutants of a bacterial ADP-ribosylating toxin such as a cholera toxin (CT) (either in a wild-type or mutant form, e.g., wherein the glutamic acid at amino acid position 29 is replaced by another amino acid, preferably a histidine, in accordance with International Patent Application No. PCT/US99/22520), a pertussis toxin (PT), killed *Bordetella*, or an *E. coli* heat-labile toxin (LT), particularly LT-K63 (where lysine is substituted for the wild-type amino acid at position 63) LT-R72 (where arginine is substituted for the wild-type amino acid at position 72), CT-S 109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); CpG oligonucleotides and other immunostimulating sequences (ISSs); Amphigen, Avridine, L121/squalene, D-lactide-polylactide/glycoside, pluronic plyois, muramyl dipeptide; and other substances that act as immunostimulating agents to enhance the effectiveness of the composition. For example, the RNA motifs can be combined or conjugated with alum to promote the generation of an immune response (e.g. a Th1-biased immune response). In certain embodiments the combination of these motifs with adjuvant emulsions, for example, but not limited to MF59. In certain embodiments, the these motifs can be combined with MF59 to promote the generation of an immune response (e.g. a Th1-biased immune response). In certain embodiments, the motif is conjugated with MF59 to promote the generation of an immune response (e.g. a Th1-biased immune response).

In certain embodiments, the ratio of RNA motif to adjuvant can range from about 1 µg motif:about 100 µl adjuvant formulation. In certain embodiments, the ratio of RNA motif to adjuvant formulation can range from about 1 µg motif: about 95 µl adjuvant formulation; about 1 µg motif:about 90 µl adjuvant formulation; about 1 µg motif:about 85 µl adjuvant formulation; about 1 µg motif:about 80 µl adjuvant formulation; about 1 µg motif:about 75 µl adjuvant formulation; about 1 µg motif:about 70 µl adjuvant formulation; about 1 µg motif:about 65 µl adjuvant formulation; about 1 µg motif:about 60 µl adjuvant formulation; about 1 µg motif:about 55 µl adjuvant formulation; about 1 µg motif: about 50 µl adjuvant formulation; about 1 µg motif:about 45 µl adjuvant formulation; about 1 µg motif:about 40 µl adjuvant formulation; about 1 µg motif:about 35 µl adjuvant formulation; about 1 µg motif:about 30 µl adjuvant formulation; about 1 µg motif:about 25 µl adjuvant formulation; about 1 µg motif:about 20 µl adjuvant formulation; about 1 µg motif:about 15 µl adjuvant formulation; or about 1 µg motif:about 10 µl adjuvant formulation. In certain embodiments, the ratio of RNA motif to adjuvant formulation can be about 1 µg motif:about 40 µl adjuvant formulation.

In certain embodiments, the ratio of RNA motif to adjuvant formulation can be about 10-50 pmols of the motif: about 40 µl adjuvant formulation. In certain embodiments, the ratio of RNA motif to adjuvant formulation can be about 10 pmols motif:about 40 µl adjuvant formulation; about 12.5 pmols motif:about 40 µl adjuvant formulation; about 15 pmols motif:about 40 µl adjuvant formulation; about 17.5 pmols motif:about 40 µl adjuvant formulation; about 20 pmols motif:about 40 µl adjuvant formulation; about 22.5 pmols motif:about 40 µl adjuvant formulation; about 25 pmols motif:about 40 µl adjuvant formulation; about 27.5 pmols motif:about 40 µl adjuvant formulation; about 30 pmols motif:about 40 µl adjuvant formulation; about 32.5 pmols motif:about 40 µl adjuvant formulation; about 35 pmols motif:about 40 l adjuvant formulation; about 37.5 pmols motif:about 40 µl adjuvant formulation; about 40 pmols motif:about 40 µl adjuvant formulation; about 42.5 pmols motif:about 40 µl adjuvant formulation; about 45 pmols motif:about 40 µl adjuvant formulation; about 47.5 pmols motif:about 40 µl adjuvant formulation; or about 50 pmols motif:about 40 µl adjuvant formulation.

In certain embodiments, the RNA motifs can also be constructed as part of an appropriate vector (viral or otherwise). The term "vector" means the vehicle by which a nucleic acid sequence can be introduced into a cell. Vectors include plasmids, phages, viruses, etc. A "therapeutic vector", as used herein, refers to a vector which is acceptable for administration to an animal, and particularly to a human.

Vectors typically comprise the DNA of a transmissible agent, into which foreign nucleic acid molecule is inserted. A common way to insert one nucleic acid molecule into another segment of DNA involves the use of enzymes called restriction enzymes that cleave DNA at specific sites (specific groups of nucleotides) called restriction sites. Generally, the foreign nucleic acid molecule is inserted at one or more restriction sites of the vector DNA, and then is carried by the vector into a host cell along with the transmissible vector DNA.

Suitable vectors include viruses, such as adenoviruses, adeno-associated virus (AAV), lentiviral vectors, vaccinia, herpesviruses, paramyxoviruses, Sendai Virus, RNA-based viruses, Newcastle disease virus, baculoviruses, orthomyxovirus, RNA-based viruses, retroviruses, parvovirus, lentivirus, bacteriophages, cosmids, plasmids, fungal vectors, and other recombination vehicles typically used in the art.

Methods that can be used to deliver the RNAs of the present disclosure are described in, for example, but not by way of limitation, Clegg, C. H. et al. *Proc Natl Acad Sci USA* 109, 17585-17590, (2012); Thim, H. L. et al. *Vaccine* 30, 4828-4834, (2012); Alving, C. R., et al. *Curr Opin Immunol* 24, 310-315, (2012); Baldwin, S. L. et al. T *Immunol* 188, 2189-2197 (2012); Nordly, P. et al. *J Control Release* 150, 307-317, (2011); Schneider-Ohrum, K. et al. *Vaccine* 29, 9081-9092, (2011); Caskey, M. et al. *J Exp Med* 208, 2357-2366, 2011); Petsch, B. et al. Pr *Nat Biotechnol* 30, 1210-1216, (2012), the contents of which are expressly incorporated herein by reference).

In certain embodiments, the RNA motifs of the disclosed subject matter (either naked RNA or RNA linked to a delivery vehicle as described above), can be administered parenterally, e.g., subcutaneously or intramuscularly, aerosolized, electroporated in the skin or muscle, or used intranasally, etc., or delivered by any other suitable route for delivery of RNA alone or in combination with a vaccine. In another embodiment, the compositions of the disclosed subject matter can be administered topically onto the skin or to the mucosa of a subject (see, e.g., Pavot, V., *Vaccine* 2012 Jan. 5; 30(2):142-54 and Bal, S M *J. Control Release* 2010 Dec. 20; 148(3):266-82).

Delivery of the RNA Motifs with Antigens

As described herein, as an adjuvant, the RNA motifs of the presently disclosed subject matter can be administered in combination with vaccines, to stimulate the immune response to pathogens, toxins, and self-antigens. In certain embodiments, the RNA motif (or motifs) can be provided together with or conjugated to the antigen. In certain embodiments, the RNA motif (or motifs) can be can be conjugated to or encapsulated in a natural or synthetic nanoparticle, for example, but not limited to, liposomes, virus like particles, polymers to impart its immunostimulatory activity.

In certain embodiments, the RNA motif (or motifs) (e.g., SEQ ID NO:1; SEQ ID NO:2; SEQ ID NO:5), or a modified variant of SEQ ID NO:1 having immunostimulatory activity, can be administered in combination with vaccines, to stimulate the immune response to pathogens, toxins, and self-antigens. In certain embodiments, the RNA motif is conjugated to additional nucleotides and administered in combination with vaccines, to stimulate the immune response to pathogens, toxins, and self-antigens. For example, the modified RNA motif can have additional nucleotides at the 5' or 5' and 3' end of the DVG70-114 motif as described above (e.g., SEQ ID NO: 23).

In certain embodiments, the antigen can be any of a wide variety of substances capable of producing a desired immune response in a subject. The antigens used with these adjuvant compositions can be one or more of viruses (inactivated, attenuated, and modified live), bacteria, fungi, parasites, parasite eggs, nucleotides, polynucleotides, peptides, polypeptides, recombinant proteins, synthetic peptides, protein extract, cells (including tumor cells), tissues, polysaccharides, carbohydrates, fatty acids, teichioc acid, peptidoglycans, lipids, or glycolipids, individually or in any combination thereof. In certain embodiments, the antigens used with the adjuvants of the disclosed subject matter can also include immunogenic fragments of nucleotides, polynucleotides, peptides, polypeptides, that can be isolated from the organisms referred to herein. In certain embodiments, they can also be in the form of DNA vaccines.

Live, modified-live, and attenuated viral strains are those that either do not cause disease in a subject have been isolated in non-virulent form or have been attenuated using methods well known in the art, including serial passage in a suitable cell line or exposure to ultraviolet light or a chemical mutagen. Inactivated or killed viral strains are those which have been inactivated by methods known to those skilled in the art, including treatment with formalin, betapropriolactone (BPL), binary ethyleneimine (BEI), sterilizing radiation, heat, or other such methods.

In certain embodiments, two or more antigens can be combined to produce a polyvalent composition that can protect a subject against a wide variety of diseases caused by the pathogens. While conventional adjuvants are often limited in the variety of antigens with which they can be effectively used (either monovalently or polyvalently), the adjuvants described herein can be used effectively with a wide range of antigens, both monovalently and polyvalently. Thus, in certain embodiments, the antigens described herein can be combined in a single composition comprising the adjuvants described herein.

Some examples of pathogenic viruses that can be used as antigens in the compositions and methods of the present subject matter include hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria that can be used as antigens in the compositions and methods of the present subject matter include chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lymes disease bacteria.

Some examples of pathogenic fungi that can be used as antigens in the compositions and methods of the present subject matter include *Candida* (*albicans, krusei, glabrata, tropicalis*, etc.), *Cryptococcus neoformans, Aspergillus* (*fumigatus, niger*, etc.), Genus *Mucorales* (*Mucor, Absidia, Rhizophus*), *Sporothrix schenkii, Blastomyces dermatitidis, Paracoccidioides brasiliensis, Coccidioides immitis* and *Histoplasma capsulatum*.

Some examples of pathogenic parasites that can be used as antigens in the compositions and methods of the present subject matter include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi, Nippostrongylus brasiliensis*, and *Schistosomiasis*.

Tumor antigens can also be used in the adjuvant compositions of the present subject matter. Many strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology, Fifth Edition). In certain of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci U.S.A. 90 (80: 3539-43).

The study of gene expression and large scale gene expression patterns in various tumors has led to the definition of so called tumor specific antigens (Rosenberg, S A (1999) Immunity 10: 281-7). In many cases, these tumor specific antigens are differentiation antigens expressed in the tumors and in the cell from which the tumor arose, for example melanocyte antigens gp 100, MAGE antigens, Trp-2. More importantly, many of these antigens can be shown to be the targets of tumor specific T cells found in the host. The tumor antigen can also include the protein telomerase, which is required for the synthesis of telomeres of chromosomes and which is expressed in more than 85% of human cancers and in only a limited number of somatic tissues (Kim, N et al. (1994) Science 266, 2011-2013). (These somatic tissues can be protected from immune attack by various means). Tumor antigen can also be "neo-antigens" expressed in cancer cells because of somatic mutations that alter protein sequence or create fusion proteins between two unrelated sequences (i.e. bcr-abl in the Philadelphia chromosome), or idiotype from B cell tumors. Other tumor vaccines can include the proteins from viruses implicated in human cancers such a Human Papilloma Viruses (HPV), Hepatitis Viruses (HBV and HCV) and Kaposi's Herpes Sarcoma Virus (KHSV).

Another form of tumor specific antigen which can be used in conjunction with the compositions and methods of the presently disclosed subject matter is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) Science 269: 1585-1588; Tamura, Y. et al. (1997) Science 278: 117-120.

The RNA motifs and vaccination methods of the present disclosure can also be used in conjunction with anti-cancer therapies (e.g., chemotherapy), to augment cancerous cell death by creating a more immunogenic environment in a subject afflicted with cancer. Such combination therapy enhances cancer cell death and promotes a robust immune response capable of killing any residual cancer cells that have escaped treatment. (Lake et al. New Engl J of Med 354, 2503 (2006)). Other non-limiting examples of anti-cancer therapies that can be used with the compositions of the present disclosure include radiation, surgery, and hormone deprivation (Kwon, E. et al. (1999) Proc. Natl. Acad. Sci U.S.A. 96 (26): 15074-9). Angiogenesis inhibitors can also be used. Inhibition of angiogenesis leads to tumor cell death, which can feed tumor antigen into host antigen presentation pathways.

In certain embodiments, cancer cells (e.g., tumor cells) isolated from a subject can be exposed to the adjuvants of the present subject matter and used to treat dendritic cells ex vivo. The mature ex vivo treated dendritic cells are then re-introduced into the patient and promote a robust immune response directed against the cancer cells.

Delivery of the RNA Motifs to Confer Immunostimulatory Activity to Inert Nucleotide Molecules As described herein, the RNA motifs of the presently disclosed subject matter can be cloned into the genome of a non-immunostimulatory virus (i.e., inert virus) to confer immunostimulatory activity against the inert virus. In certain embodiments, the RNA motif is cloned onto the 5' end of a viral gene, the 3' end of a viral gene, and/or within the viral gene, yet will still retain immunostimulatory activity. The viral genome can be either RNA or DNA. In certain of such embodiments, the RNA stem-loop structure is maintained and/or stabilized.

In certain embodiments, the RNA motif $DVG_{70-114}$ is cloned into the X-region from hepatitis C virus (HCV). In certain embodiments, the RNA motif (or motifs) (e.g., SEQ ID NO:1; SEQ ID NO:2; SEQ ID NO:5, SEQ ID NO:23) is cloned into the viral genome of hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus or arboviral encephalitis virus, yet still retains immunostimulatory activity.

In certain embodiments, the RNA motif (or motifs) is cloned into pathogenic bacteria, fungi, parasites, or tumor antigens, yet still retains immunostimulatory activity. Exemplary bacteria, fungi, parasites, and tumor antigens are listed above with respect to the delivery of the RNA motifs along with antigens.

In certain embodiments, the RNA motif (or motifs) is cloned into a polynucleotide, yet still retains immunostimulatory activity. In certain embodiments, the polynucleotide can be cDNA, genomic DNA, RNA, mRNA, RNAi, siRNAs, shRNAs, miRNA, etc. In certain embodiments, the polynucleotide can be mRNA.

Delivery of the RNA Motifs Via Attachment to Antibodies

As described herein, the RNA motifs of the presently disclosed subject matter can be conjugated or linked to an antibody to confer targeted immunostimulatory activity at the location of antibody specific antigen. Such antibodies include, but are not limited to monoclonal antibodies, subject's species specific antibodies, mammalian antibodies, human antibodies, humanized antibodies, camelid antibodies, chimeric antibodies, and anti-idiotypic (anti-Id) antibodies (including, e.g., anti-Id antibodies to antibodies of the present disclosure). The antibodies can be of any isotype/class (e.g., IgG, IgE, IgM, IgD, IgA and IgY), or subclass (e.g., IgG1, IgG2, IgG3, IgG4, IgA1 and IgA2). In another embodiment, the RNA motifs are conjugated or linked to an antigen binding fragment.

The linkage can be covalent bonds, or non-covalent interactions such as through electrostatic forces. Various linkers, known in the art, can be employed in order to form the immunoconjugate. Additionally, the immunoconjugate can be provided in the form of a fusion protein that may be expressed from a polynucleotide encoding the immunoconjugate. A "fusion protein" refers to proteins created through the joining of two or more genes or gene fragments which originally coded for separate proteins (including peptides and polypeptides). Translation of the fusion gene results in a single protein with functional properties derived from each of the original proteins.

Pharmaceutical Compositions and Administration

In certain embodiments, the RNA motifs of the present disclosure can be formulated as pharmaceutical compositions or pharmaceutical formulations by admixture with a pharmaceutically acceptable carrier or excipient. In certain embodiments, the pharmaceutical formulations can include one or more RNA motifs and a physiologically acceptable diluent or carrier. In certain embodiments, the pharmaceutical composition can further include an antigen, drug, adjuvant, or tumor chemotherapy.

In certain embodiments, the pharmaceutical formulation can be a solid dosage form. In certain embodiments, the solid dosage form can be a tablet or capsule.

In certain embodiments, the pharmaceutical formulation can be a liquid formulation. In certain embodiments, the liquid formulation can be an oral solution or oral suspension.

In certain embodiments, the pharmaceutical formulation can be a transdermal drug delivery system, e.g., a patch, cream, gel, and/or microemulsion.

In certain embodiments, the pharmaceutical formulation can include liposomes, nanoparticles, and/or other carriers. In certain embodiments, the pharmaceutical formulation can include an adjuvant or enhancer, e.g., an enzyme inhibitor.

In certain embodiments, the pharmaceutical formulation can be a direct infusion. In certain embodiments, the pharmaceutical formulation can be an implantable device.

Many methods can be used to introduce the vaccine formulations described herein, these include but are not limited to oral, topical, intradermal, intramuscular, intraperitoneal, intravenous, subcutaneous, intra-pulmonary, rectal, vaginal and intranasal routes. All such routes are suitable for administration of these compositions, and can be selected depending on the patient and condition treated if there is a condition present, and similar factors by an attending physician. In certain embodiments, it is preferable to introduce a vaccine formulation via the natural route of infection of the pathogen for which the vaccine is designed. According to the desired route for administration, the compositions of the disclosure are prepared in the form of, for example, liquids, powders, aerosols, tablets, capsules, enteric coated tablets or capsules, or suppositories.

Selection of the appropriate dosage for the priming compositions of the present disclosure can be based upon the physical condition of the mammal, most especially including the general health and weight of the immunized mammal. Such selection and upward or downward adjustment of the effective dose is within the skill of the art.

Pharmaceutical compositions of the present disclosure, suitable for inoculation or for parenteral or oral administration, comprise attenuated or inactivated forms of mammalian viruses, for example, optionally further comprising sterile aqueous or non-aqueous solutions, suspensions, and emulsions. The composition can further comprise auxiliary agents or excipients, as known in the art. See, e.g, Berkow et al., eds., The Merck Manual, 15th edition, Merck and Co., Rahway, N.J. (1987); Goodman et al., eds., Goodman and Gilman's The Pharmacological Basis of Therapeutics, 8th edition, Pergamon Press, Inc., Elmsford, N.Y. (1990); Avery's Drug Treatment: Principles and Practice of Clinical Pharmacology and Therapeutics, 3rd edition, ADIS Press, LTD., Williams and Wilkins, Baltimore, Md. (1987); Osol, A., ed., Remington's Pharmaceutical Sciences, Mack Publishing Co, Easton, Pa. pp. 1324-1341 (1980); Katzung, ed. Basic and Clinical Pharmacology, Fifth Edition, Appleton and Lange, Norwalk, Conn. (1992), which references and references cited therein, are entirely incorporated herein by reference as they show the state of the art.

For example, a virus vaccine composition of the present disclosure can comprise from about $10^2$-$10^9$ plaque forming units (PFU)/ml, or any range or value therein, where the virus is attenuated. In certain embodiments, a vaccine composition comprising an inactivated virus can comprise an amount of virus corresponding to about 0.1 to 200 micrograms of an antigenic protein/ml or combinations thereof, or any range or value therein.

In certain embodiments, preparations for parenteral administration include sterile aqueous or non-aqueous solutions, suspensions, and/or emulsions, which can contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration can generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents. See, e.g., Berkow, infra, Goodman, infra, Avery's, infra, Osol, infra and Katzung, infra, which are incorporated in their entirety herein by reference.

In certain embodiments, a vaccine composition of the present disclosure, used for administration to an individual, can further comprise salts, preservatives, chemical stabilizers, buffers, adjuvants, or other substances which are desirable for improving the efficacy of the composition. Typically, stabilizers, adjuvants, and preservatives are optimized to determine the best formulation for efficacy in the target human or animal. Suitable exemplary preservatives include chlorobutanol potassium sorbate, sorbic acid, sulfur dioxide, propyl gallate, the parabens, ethyl vanillin, glycerin, phenol, and parachlorophenol. Suitable stabilizing ingredients which can be used include, for example, casamino acids, sucrose, gelatin, phenol red, N-Z amine, monopotassium diphosphate, lactose, lactalbumin hydrolysate, and dried milk. Normally, the adjuvant and the composition are mixed prior to presentation to the immune system, or presented separately, but into the same site of the mammal being immunized. Examples of adjuvants are discussed above. Additional examples of materials suitable for use in vaccine compositions are provided in Osol, A., ed., Remington's Pharmaceutical Sciences, Mack Publishing Co, Easton, Pa. (1980), pp. 1324-1341, which reference is incorporated in its entirety herein by reference.

In certain embodiments, heterogeneity in the vaccine can be provided by mixing different modified viruses of the disclosed subject matter, such as 2-50 modified viruses or any range or value therein.

In certain embodiments, a pharmaceutical composition according to the present disclosure can further or additionally comprise at least one viral chemotherapeutic compound, including, but not limited to, gamma globulin, amantadine, ribavirin, guanidine, hydroxybenzimidazole, interferon-alpha, interferon-beta, interferon-gamma, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir (neuraminidase inhibiting drugs oseltamivir, zanamivir). See, e.g., Katzung, infra, and the references cited therein on pages 798-800 and 680-681, respectively, which references are herein entirely incorporated by reference.

In certain embodiments, a pharmaceutical composition according to the present disclosure can further or additionally comprise an aptamer to target a specific cell as provided in Bunka D. and Stockley P., "Aptamer come of age—at last," Nature Reviews Microbiology and Majumder P, et al., "From bench side research towards patented molecules with therapeutic applications," Expert Opin Ther Pat. 2009 November; 19(11):1603-13, references which are herein entirely incorporated by reference.

In certain embodiments, the vaccine can also contain variable but small quantities of endotoxin, free formaldehyde, and preservative, which have been found safe and not contributing to the reactogenicity of the vaccines for humans.

In certain embodiments, the administration of a vaccine composition of the disclosure can be for either "prophylactic" or "therapeutic" purposes. When provided prophylactically, the compositions are provided before any symptom of infection becomes manifest. In certain embodiments, the prophylactic administration of the composition serves to prevent or attenuate any subsequent infection. When provided therapeutically, the vaccine is provided upon the detection of a symptom of actual infection. The therapeutic administration of the compound(s) serves to attenuate any actual infection. See, e.g, Berkow, infra, Goodman, infra, Avery, infra and Katzung, infra, which are entirely incorporated herein by reference.

In certain embodiments, an attenuated or inactivated vaccine composition of the present disclosure can thus be provided either before the onset of infection (so as to prevent or attenuate an anticipated infection) or after the initiation of an actual infection.

In certain embodiments, a vaccine or composition of the present disclosure is physiologically significant if its presence results in a detectable change in the physiology of a recipient patient that enhances at least one primary or secondary humoral or cellular immune response against at least one strain of an infectious virus.

In certain embodiments, the "protection" provided need not be absolute, i.e., the viral infection need not be totally prevented or eradicated, if there is a statistically significant improvement compared with a control population or set of patients. Protection can be limited to mitigating the severity or rapidity of symptom onset of infection or disease.

In certain embodiments, according to the present disclosure, an "effective amount" of a vaccine composition is one that is sufficient to achieve a desired biological effect. It is understood that the effective dosage can be determined by a medical practitioner based on a number of variables including the age, sex, health, and weight of the recipient, kind of concurrent treatment, if any, frequency of treatment, and the nature of the desired outcome. In certain embodiments, the ranges of effective doses provided below are not intended to limit the disclosed subject matter, but are provided as representative preferred dose ranges. However, in certain embodiments, the most preferred dosage will be tailored to the individual subject, as is understood and determinable by one of skill in the art, without undue experimentation. See, e.g., Betkow et al., eds., The Merck Manual, 16th edition, Merck and Co., Rahway, N.J., 1992; Goodman et al., eds., Goodman and Gilman's The Pharmacological Basis of Therapeutics, 8th edition, Pergamon Press, Inc., Elmsford, N.Y., (1990); Avery's Drug Treatment: Principles and Practice of Clinical Pharmacology and Therapeutics, 3rd edition, ADIS Press, LTD., Williams and Wilkins, Baltimore, Md. (1987), Ebadi, Pharmacology, Little, Brown and Co., Boston, Mass. (1985); and Katzung, infra, which references and references cited therein, are entirely incorporated herein by reference.

In certain embodiments, the dosage of an attenuated virus vaccine for a mammalian (e.g., human) adult can be from about $10^3$-$10^7$ plaque forming units (PFU)/kg, or any range or value therein. In certain embodiments, the dose of inactivated vaccine can range from about 1 to 50 micrograms of an antigenic protein. However, the dosage should be a safe and effective amount as determined by conventional methods, using existing vaccines as a starting point.

In certain embodiments, the dosage of immunoreactive protein in each dose of virus or modified virus vaccine can be standardized to contain a suitable amount, e.g., 1-50 micrograms or any range or value therein, or an amount recommended by the U.S. Public Health Service (PHS). Each 0.5-ml dose of vaccine preferably contains approximately 1-50 billion virus particles, and preferably 10 billion particles.

While this disclosure generally discusses immunization in the context of prophylactic methods of protection, the term "immunizing" is meant to refer to both prophylactic and/or therapeutic methods. Thus, in certain embodiments, a method of immunizing includes both methods of protecting an individual from pathogen challenge, as well as methods for treating an individual suffering from pathogen infection. Accordingly, the present disclosure can be used as a vaccine for prophylactic protection and/or in a therapeutic manner; that is, as a reagent for immunotherapeutic methods and preparations.

EXAMPLES

The following examples are put forth so as to provide those of ordinary skill in the art with a complete disclosure and description of how to make and use the presently disclosed subject matter, including, but not limited to the use of RNA molecule $DVG_{70-114}$ or modified variants thereof to induce or enhance immunostimulatory responses in a subject. The following examples are not intended to limit the scope of the presently disclosed subject matter. It is understood that various other embodiments may be practiced, given the general description provided above.

Example 1: DVGs Promote Protection to Infection with an Unrelated Virus

To examine whether SeV iDVGs induce a broad antiviral state that could protect against unrelated viral infections, mouse cells were infected either with SeV C containing high levels of copy-back iDVGs (SeV HD) or with SeV C depleted of iDVGs (SeV LD) or left untreated (N/T) and re-infected 6 h later with the unrelated IAV. Cells pre-infected with SeV HD were significantly more resistant to IAV replication than were cells pre-infected with SeV LD (FIG. 1A) and induced higher antiviral gene expression levels (FIG. 1B). These data indicate that SeV iDVGs stimulate a strong antiviral state that can protect against infection with unrelated viruses.

Figure 3B:
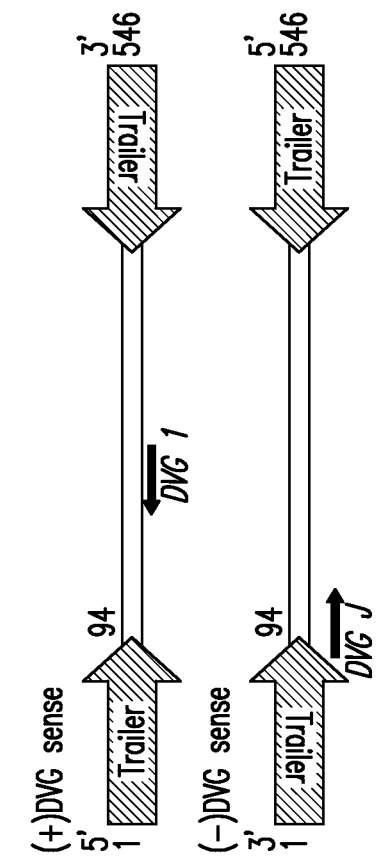
Figure 3C:
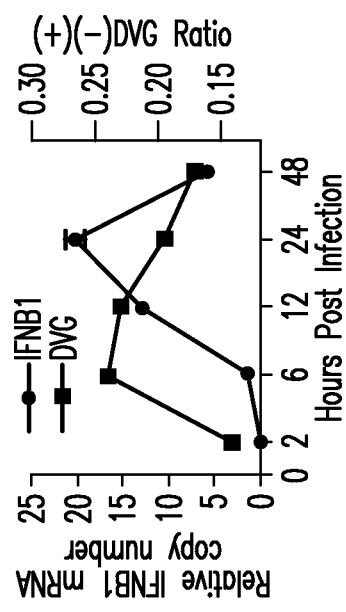
Figure 3D:
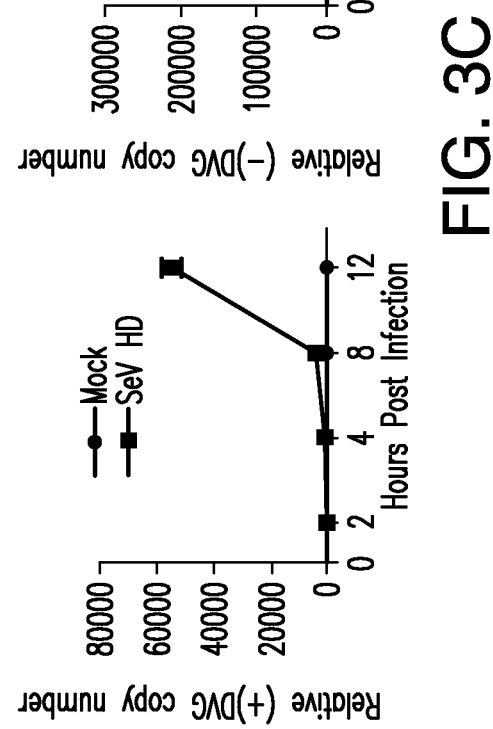

Because copy-back DVGs maintain the promoter elements necessary for replication, both positive and negative DVG RNA strands are present in infected cells (FIG. 2A). To narrow down the search for molecular motifs that confer strong stimulatory activity to iDVGs, it was first assessed whether a specific strand of iDVG preferentially activates the host antiviral response during infection. The number of (+) and (−) RNA strands of a predominant iDVGs (DVG-546) present during infection with SeV strain Cantell (denoted "high DVG": HD) (12, 35) was quantified and correlated to amounts with IFNB1 mRNA expression. The description and validation of this assay are shown in FIGS. 3A and 3B. Although copy numbers of (−)DVG strands were consistently higher than those of (+)DVG strands throughout the infection (FIG. 3C), an increased ratio of (+)/(−)DVG strands positively correlated with the induction of IFNB1 expression in infected humans A549 cells (FIG. 2B). The strong correlation between (+)DVG RNA and type I IFN expression was recapitulated in LLC-MK2 cells, a cell line highly permissive to SeV replication (FIG. 3D). Confirming the strong ability of (+)DVG RNA to stimulate the antiviral response, RNA-fluorescent in situ hybridization (RNA-FISH) in combination with immunofluorescence staining (IFA) showed that IRF3 translocation to the nucleus occurs predominantly in cells showing a strong DVG signal (FIGS. 2C and 2D). Thus, accumulation of (+) copy-back DVG is positively associated with the induction of antiviral responses in cells infected with SeV.

Figures 4A, 4B:
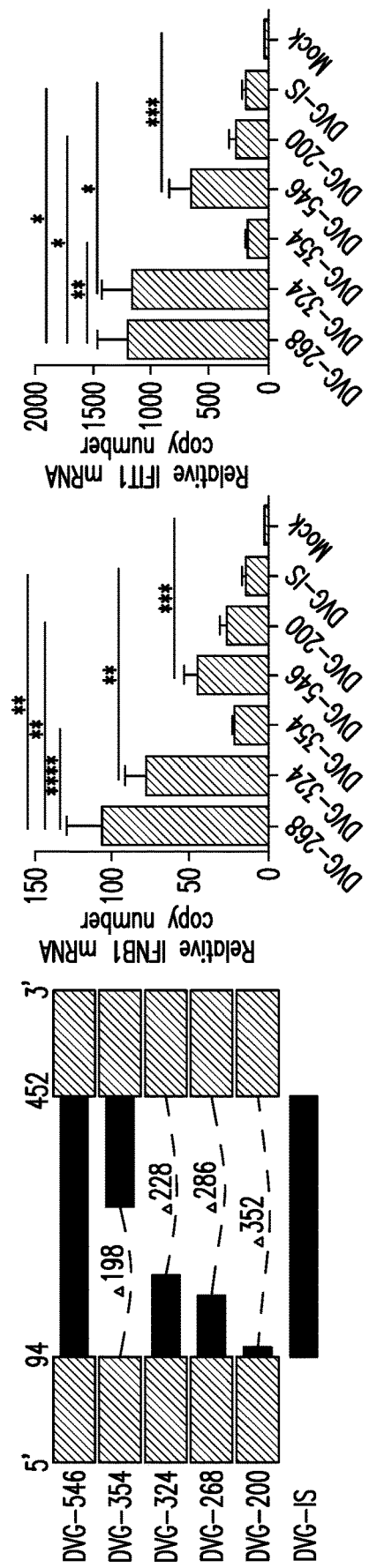
FIG. 4A-FIG. 4G. Identification of a candidate motif essential for type I IFN induction by DVG RNA.
Figure 4C:
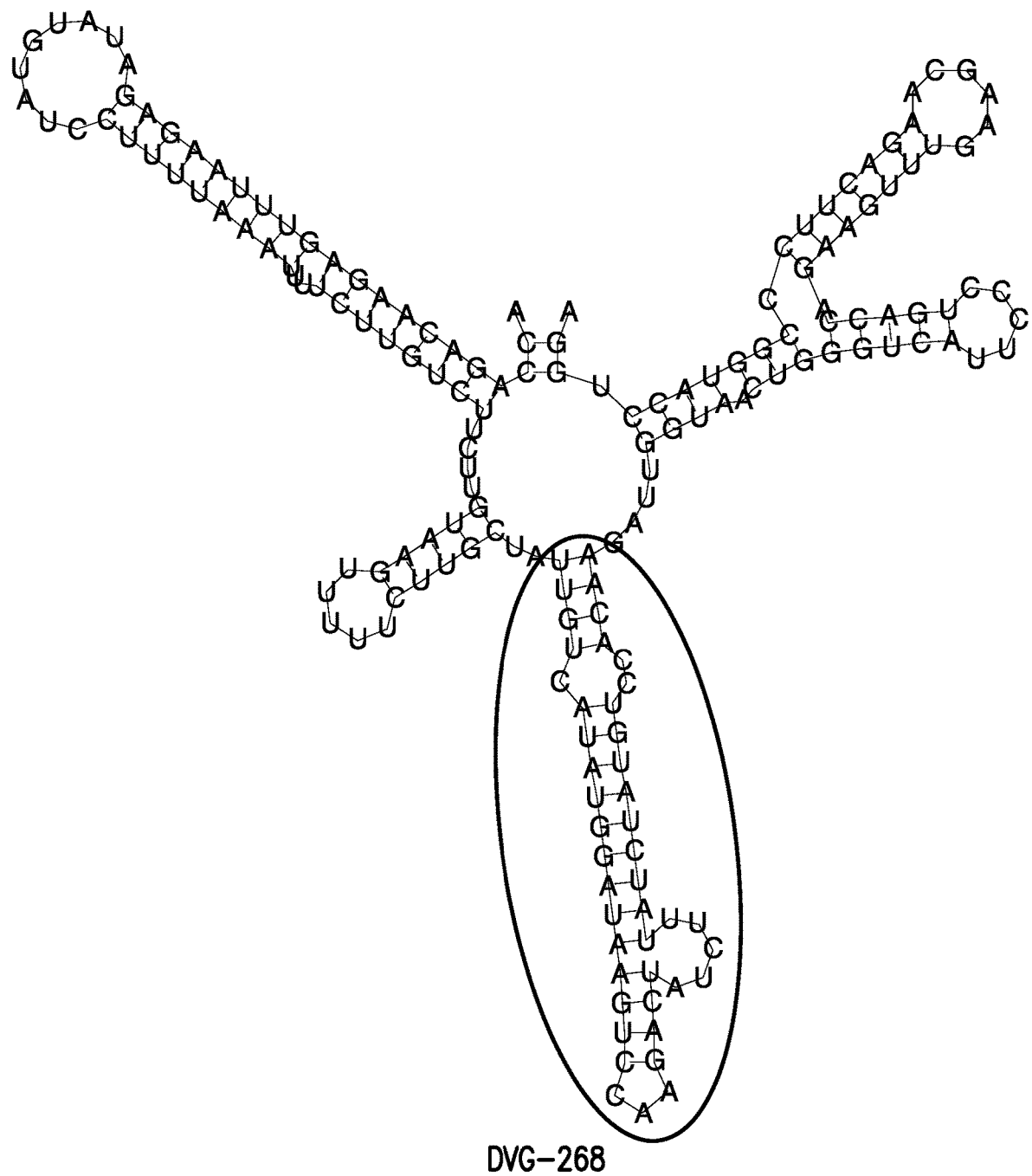
Figure 4C:
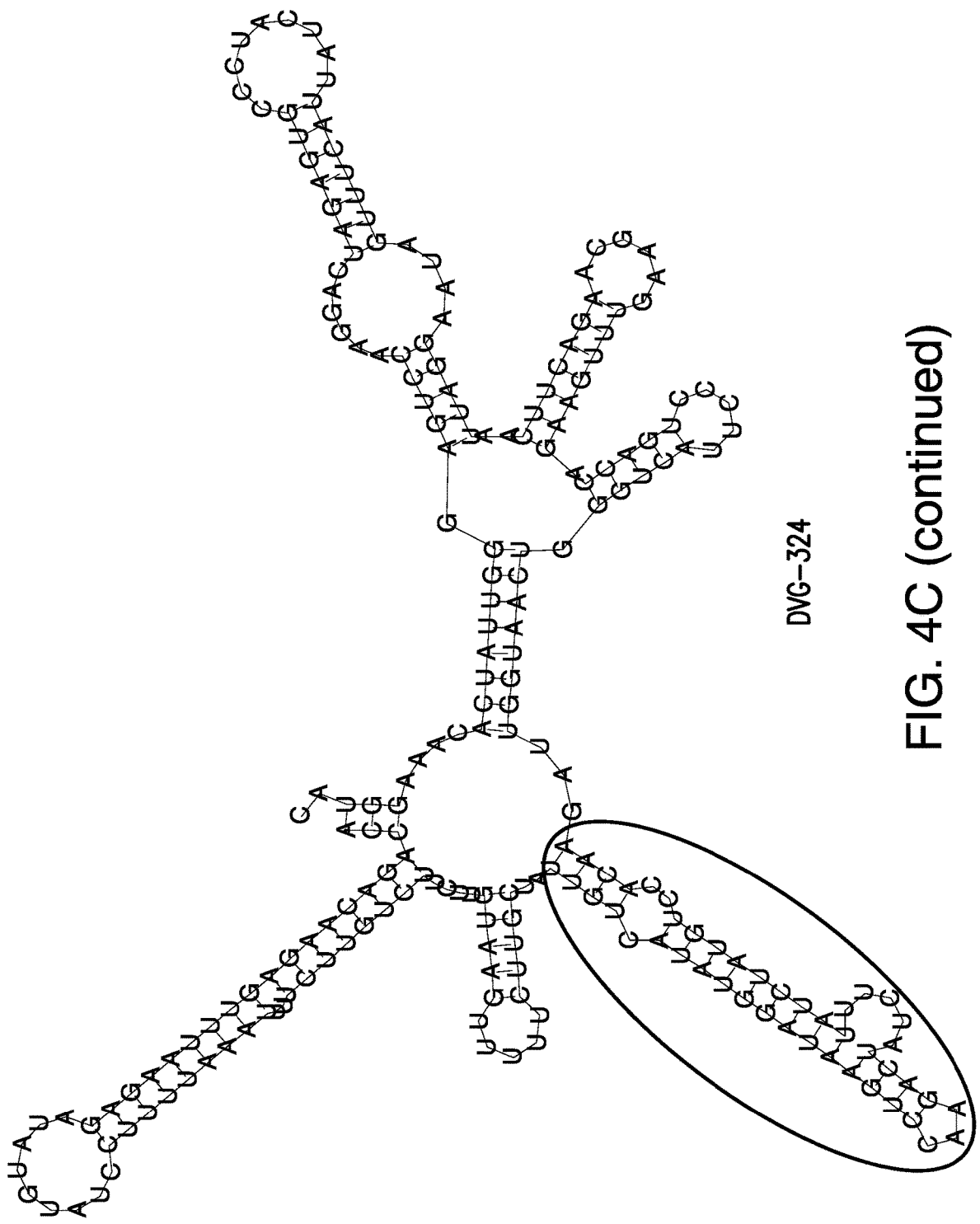
Figure 4C:
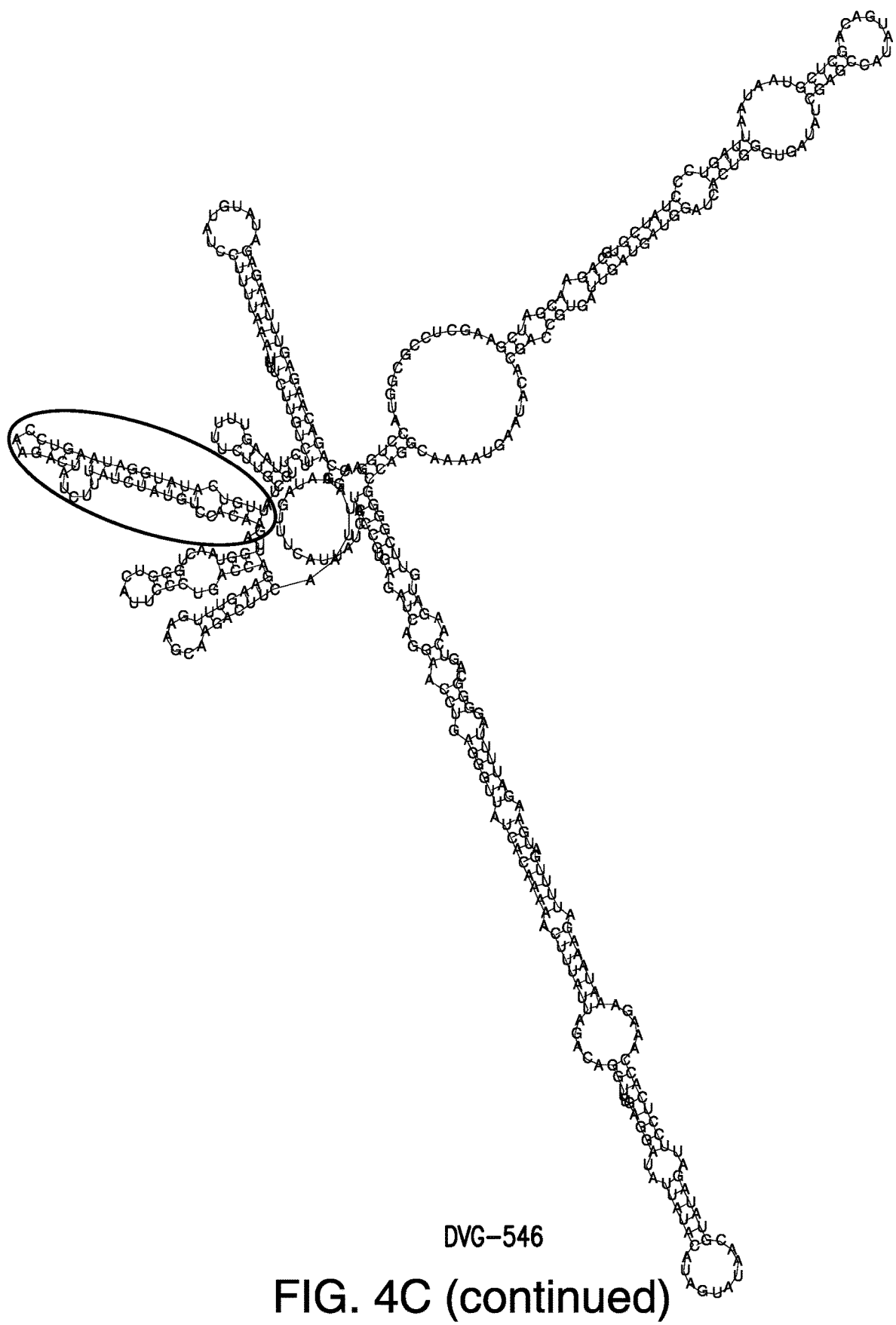
Figure 4C:
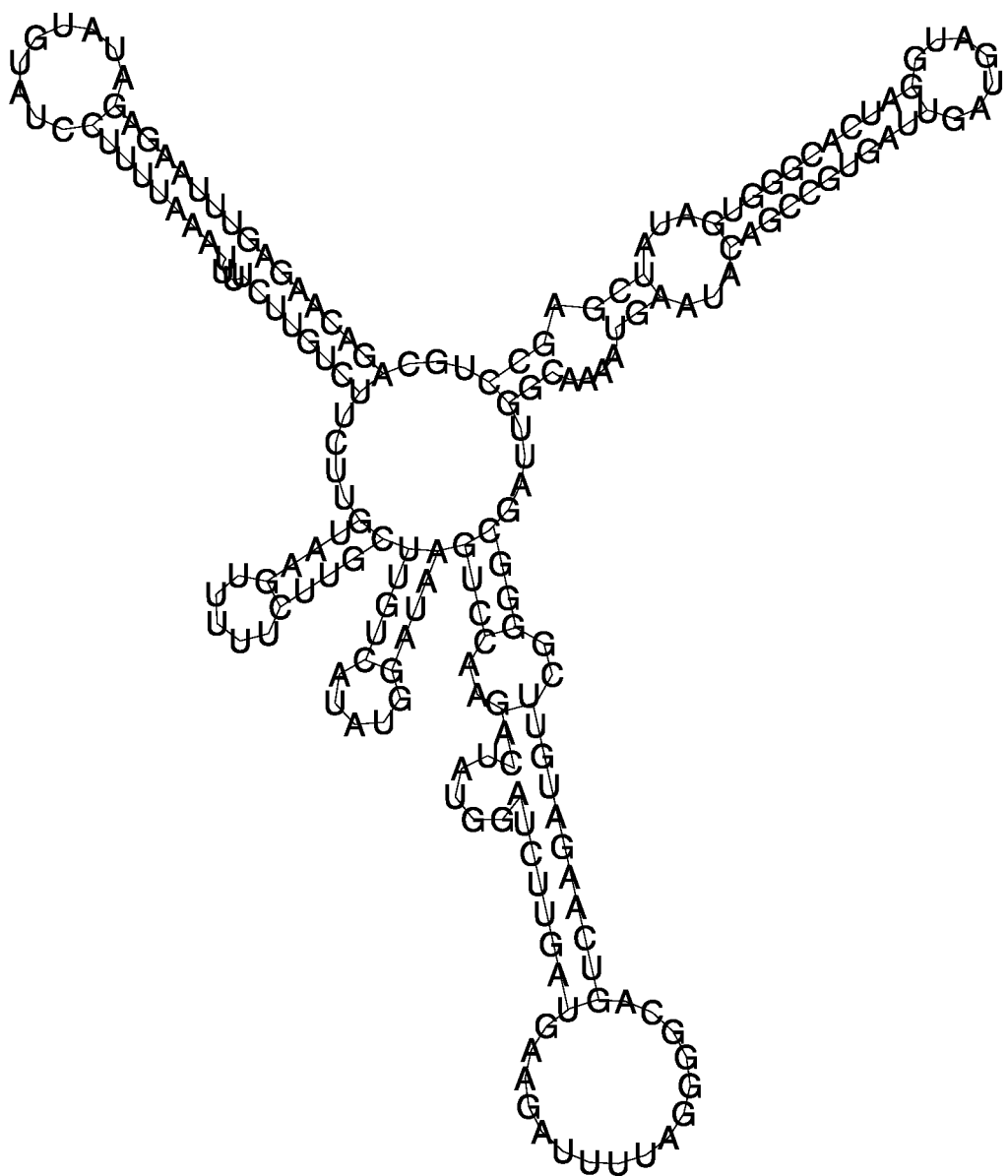
Figure 4C:
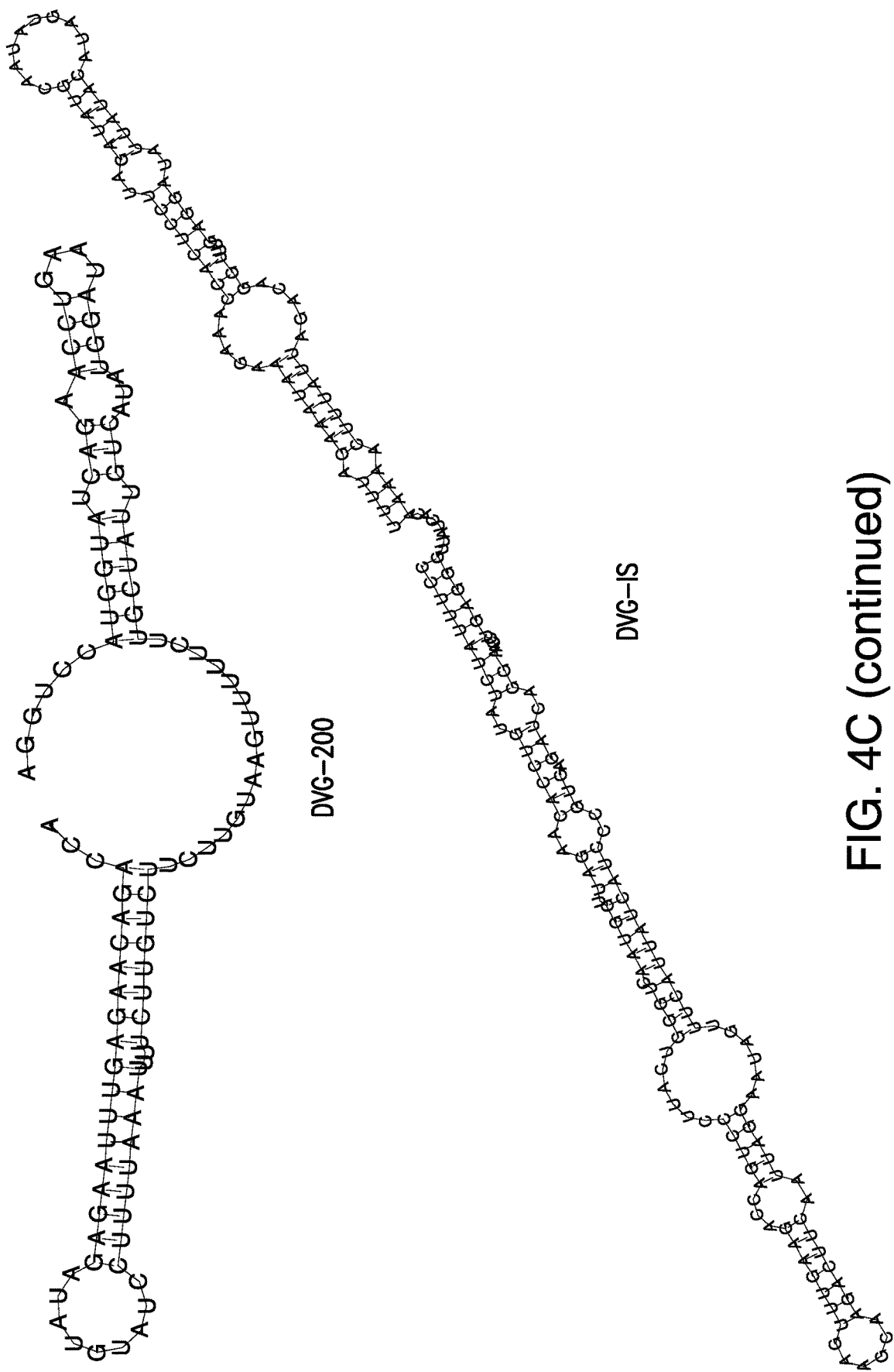

Example 2: Identification of a Candidate Motif Essential for Type I IFN Induction by (+)DVG RNA It was previously reported that alterations in the internal (non-complementary) region of DVG-546 drastically affect its stimulatory ability (26). Specifically, a DVG-mutant retaining the 5' end of the internal sequence (DVG-324) promoted enhanced expression of type I IFNs upon transfection, while a mutant missing the 5' end of the internal sequence (DVG-354) significantly lost its stimulatory capacity (26). These data suggest that a specific region towards the 5' end of the internal sequence plays an essential role in maximizing the stimulatory potential of DVG RNA. Additional mutants further confirmed this prediction. One mutant that retained a shorter 5' internal sequence (DVG-268; FIG. 4A-C) also showed potent immunostimulatory activity while mutants lacking either the complete internal sequence (DVG-200) or both complementary sequences (DVG IS, FIG. 4A-C) showed reduced ability to stimulate antiviral genes upon transfection. For all the studies reported here, ivtDVGs were tested for purity, endotoxin content, and activity after gel purification as shown in FIG. 5 (see also FIGS. 6 and 7). This differential activity of mutant DVG proteins was sustained over a 24-h time course, ruling out the possibility of different kinetics of IFN induction by the different mutant proteins (see FIG. 6C). For all of these studies, in vitro-transcribed DVG(ivtDVG) RNAs were purified from gels, tested for purity and endotoxin content, and transfected into cells at equal molarity (see FIG. 7A to 7D).

Figure 4D:
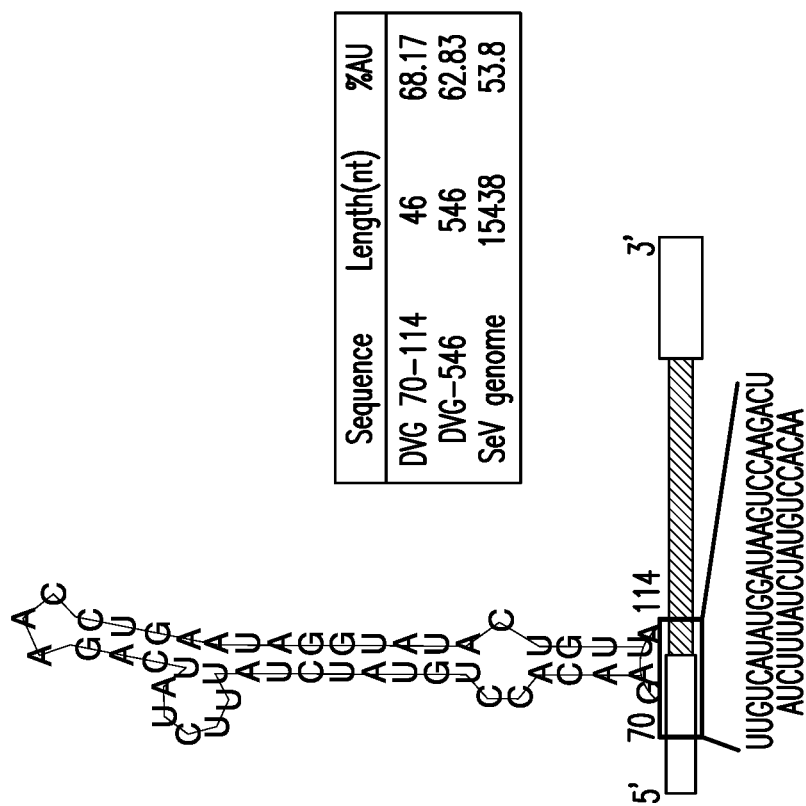

To identify the specific sequence and/or secondary RNA structure responsible for the strong stimulatory activity of iDVGs, the folding of mutants with either strong or weak ability to induce type I IFN expression was modeled in silico. Based on the modeling, structures present only in strong inducers as candidates to maximize the DVG stimulatory ability was identified (FIG. 4C). For in silico folding predictions, the 3' complementary sequence of the constructs was excluded since long complementarities strongly interfere with predictions based on minimal free energy resulting in predicted structures that significantly deviate from the natural folding of the molecule. In these conditions, a candidate stem loop domain formed by nucleotides 70-114 ($DVG_{70-114}$) was identified that was only observed in DVG mutants showing strong stimulatory ability (FIG. 4D). This region is enriched in A/U nucleotides when compared to the positive sense SeV genome or the full length DVG-546 (FIG. 4D). $DVG_{70-114}$ spans the 3' end of the 5' complementary sequence and the 5' end of the internal sequence, consistent with a partial requirement for sequences of the complementary and internal regions of the DVG RNA. This analysis identified $DVG_{70-114}$ as a candidate motif that provides strong immunostimulatory activity to SeV iDVG RNA.

Figure 4E:
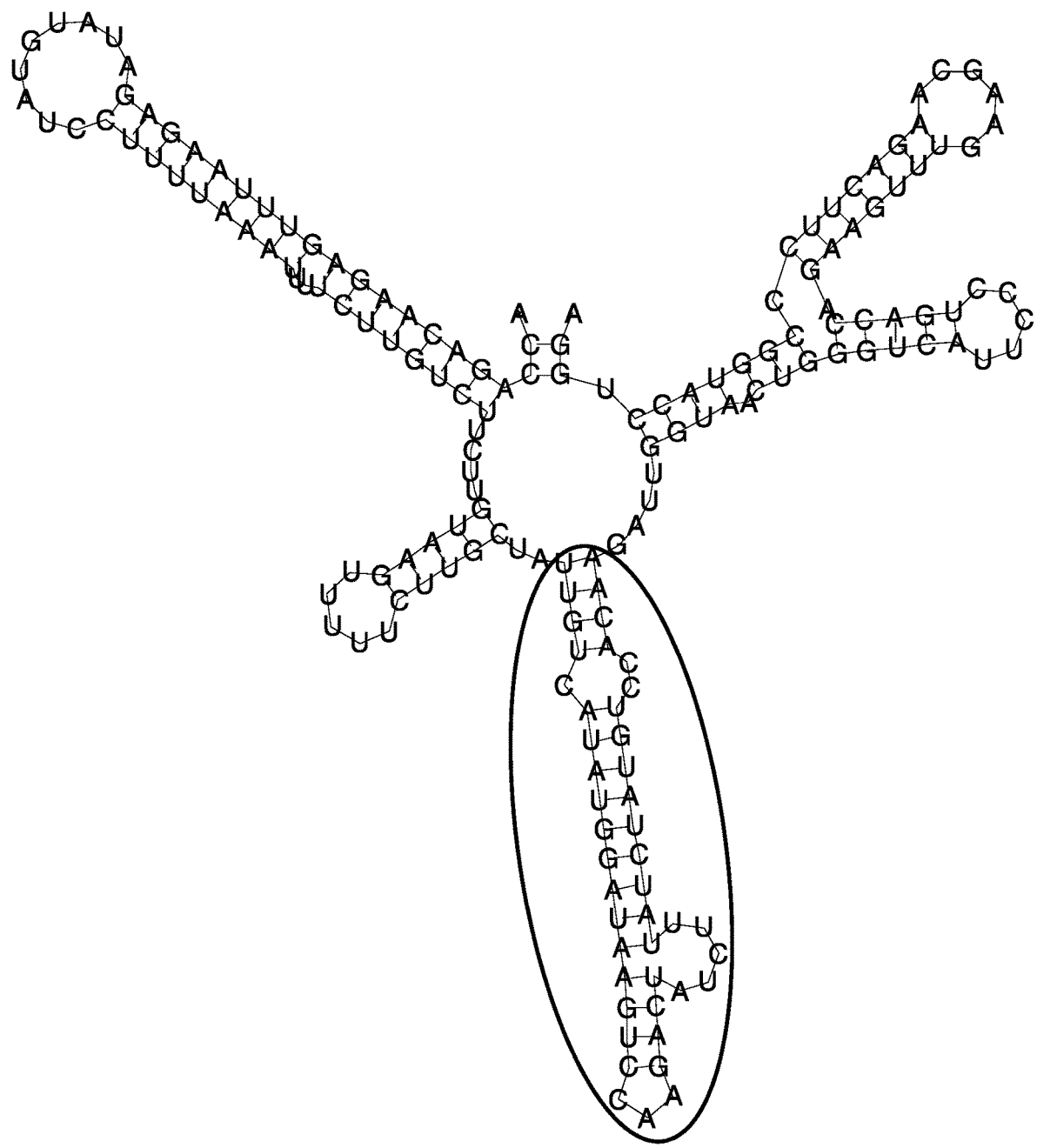
Figure 4E:
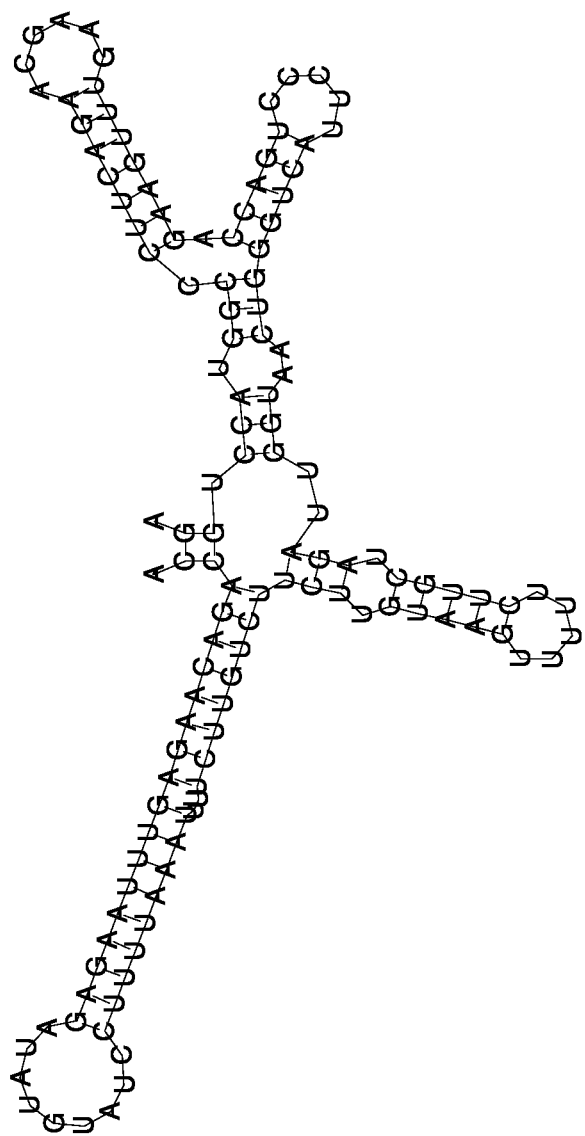
Figure 4E:
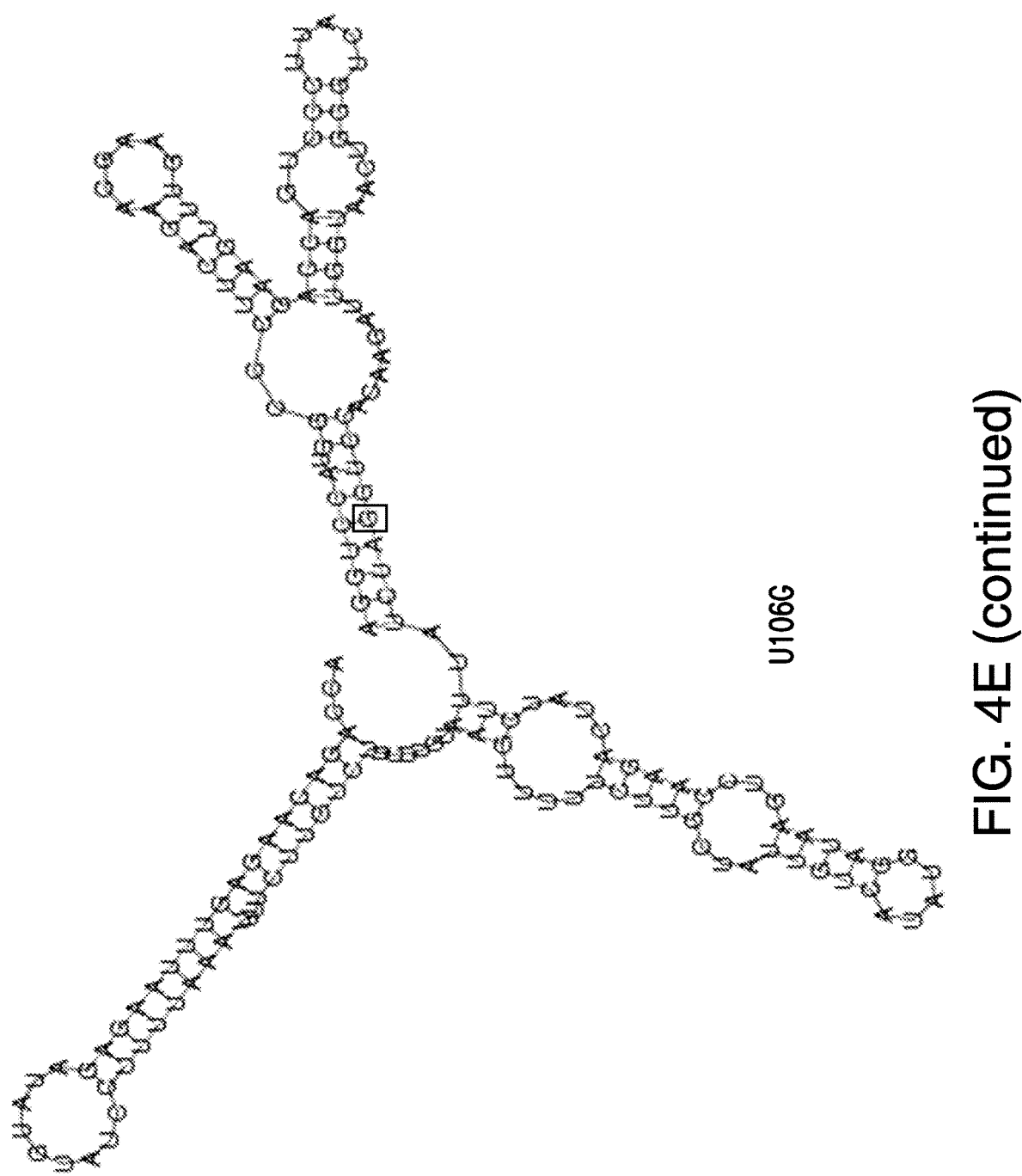
Figure 4E:
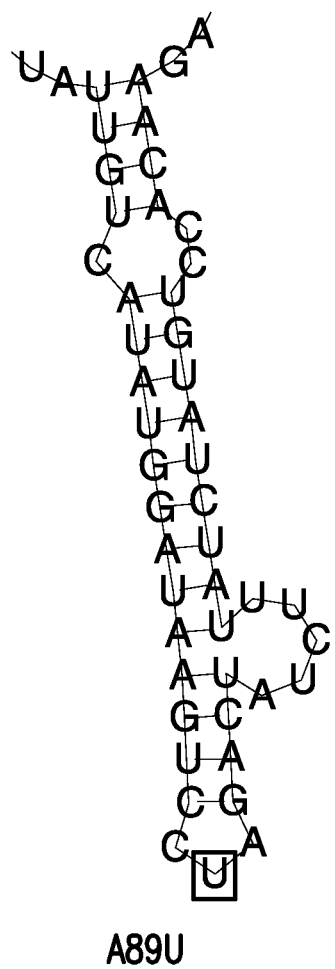
Figure 4E:
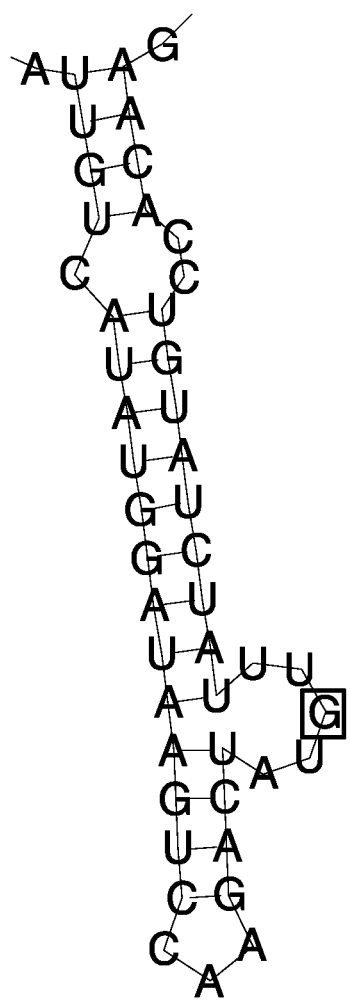
Figure 4F:
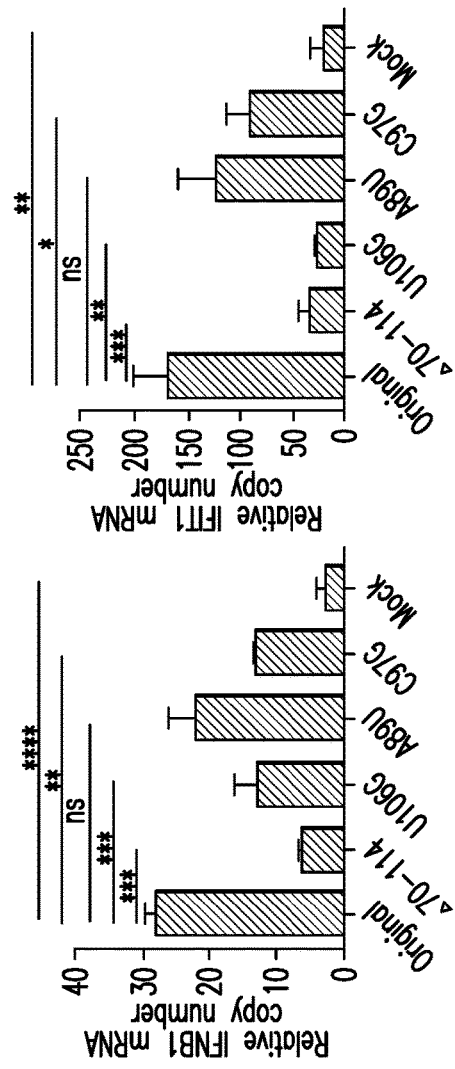
Figure 4G:
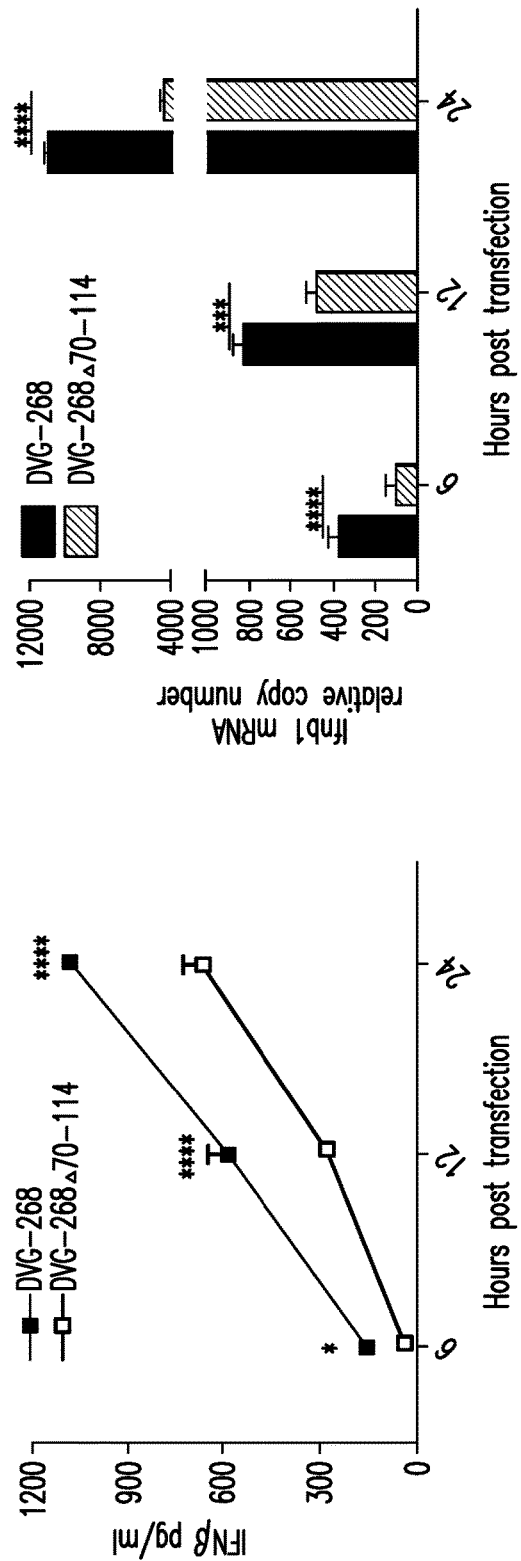
Figure 8B:
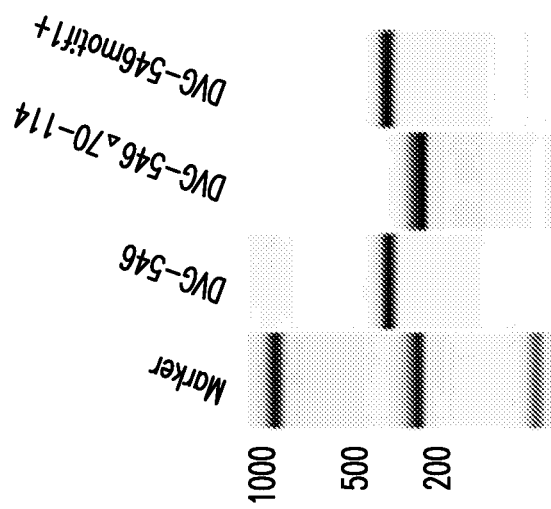
FIG. 8A-FIG. 8F. Verification of motif $DVG_{70-114}$ activity in ivtDVG-546.
Figure 8A:
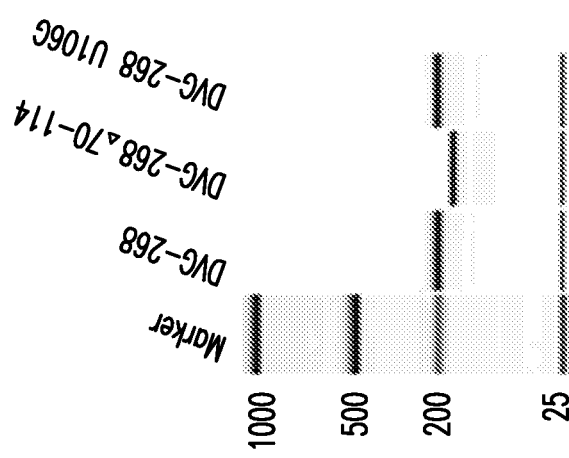
Figure 8C:
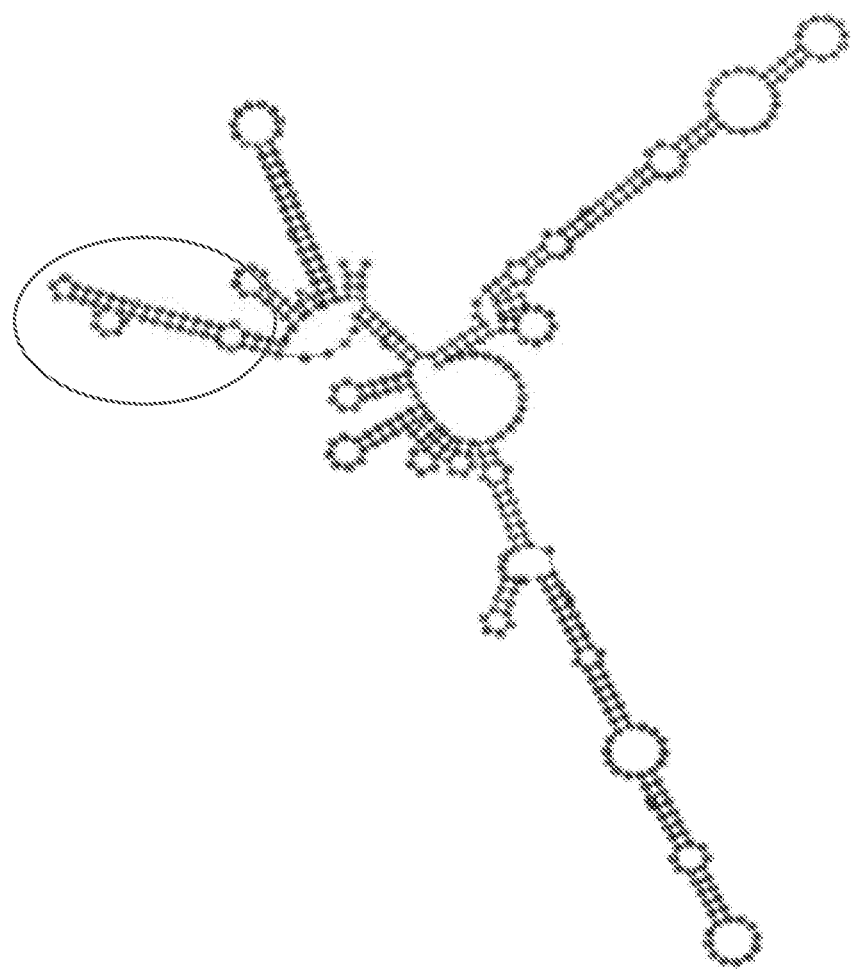
Figure 8C:
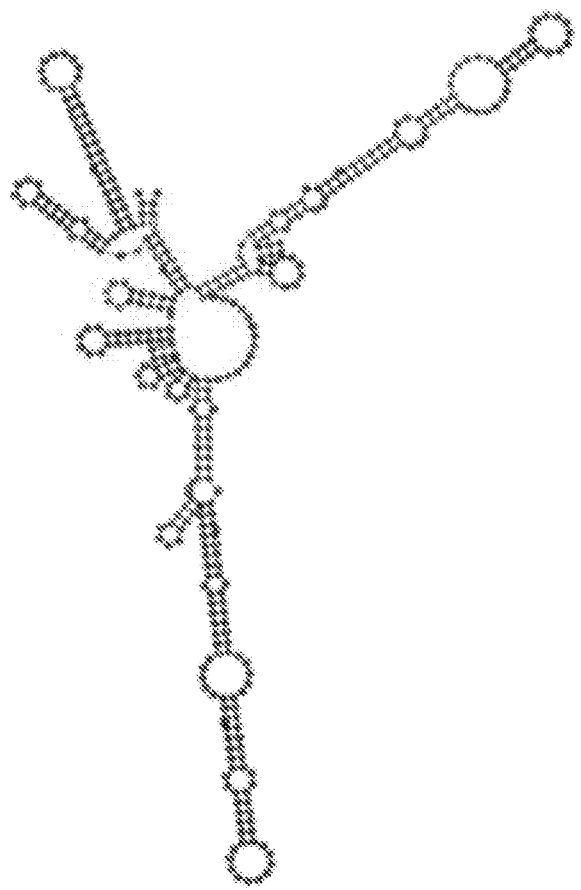
Figure 8D:
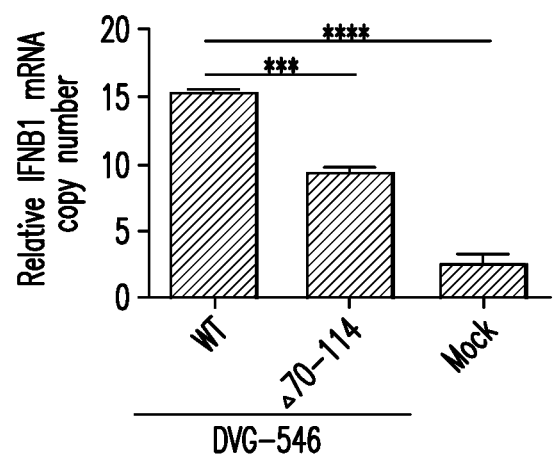

Example 3: $DVG_{70-114}$ is Necessary for the Strong Stimulatory Activity of SeV DVG RNA To determine whether $DVG_{70-114}$ is necessary for the strong stimulatory ability of SeV DVG RNA, the $DVG_{70-114}$ motif was removed from DVG-268 or the parental DVG-546. Removal of $DVG_{70-114}$ did not significantly affect other secondary structures of these molecules (FIGS. 4E and 8C). Quality controls can be found in FIGS. 8A and 8B. Removal of $DVG_{70-114}$ nearly abolished the stimulatory activity of DVG-268, and cells transfected with ivtDVG-268$_{\Delta 70-114}$ expressed significantly lower levels of IFNB1 and IFIT1 mRNA compared to cells transfected with ivtDVG-268 (FIG. 4F). This difference was recapitulated in murine cells and sustained at the RNA and protein levels over a 24-h time course (FIG. 4G). Significantly reduced activity was also observed in ivtDVG-546$_{\Delta 70-114}$ (FIGS. 8C and 8D) demonstrating that $DVG_{70-114}$ significantly augments the stimulatory activity of SeV iDVG RNA.

To further confirm the stimulatory role of $DVG_{70-114}$, point mutations were introduced into this motif. A nucleotide swap within the stem region of $DVG_{70-114}$(U106G) disrupted the complementarity structure of $DVG_{70-114}$ motif (FIG. 4E) resulting in reduced stimulatory activity of DVG-268 (FIG. 4F) and suggesting that the potent stimulatory activity of SeV iDVGs depends on the integrity of the $DVG_{70-114}$ motif. To address if specific non-complementary structures within $DVG_{70-114}$ are necessary for stimulation, single nucleotide swaps were introduced at the most distal loops of the $DVG_{70-114}$ motif (A89U and C97G) while preserving the overall predicted structure of the motif (FIG.

4E). Interestingly, the C97G mutation, but not the A89U mutation (SEQ ID NO:5) decreased the stimulatory activity compared to the parental DVG-268 (FIG. 4F), indicating that both structure and sequence influence the stimulatory activity of $DVG_{70-114}$.

Example 4: $DVG_{70-114}$ Promotes Strong Antiviral Responses During SeV Infection, Overcoming Viral Antagonism To test whether $DVG_{70-114}$ is involved in the stimulation of antiviral immunity during infection, SeV stocks including recombinant defective viral particles were generated containing the $DVG_{70-114}$ motif (rDVG-324) or lacking this motif (rDVG-354) as shown in FIGS. 4A and 9A (26). As shown in FIG. 9B, LL-CMK2 cells were infected with virus rDVG-324 or rDVG-354 at an MOI of 5 TCID50/cell and analyzed at 6 h postinfection by RT-qPCR for the expression of IFN-β1, IFIT1, and SeV NP mRNA. The relative copy number of DVGRNA was quantified by RT-qPCR with the DVGcomp primers (see Table 2).

TABLE 2

Primers(SEQ ID NOS 25-52, respectively, in order of appearance) used in mutagenesis and mutant verification

| Primers | Forward/reverse primers (5' to 3') |
|---|---|
| Δ70-114 | GTTCTTGTAAGTTTTTCTTGCTAGATTGGTAACTGGGTCATTCCC (SEQ ID NO: 25)/ GGGAATGACCCAGTTACCAATCTAGCAAGAAAAACTTACAAGAAC (SEQ ID NO: 26) |
| Δ5-51 | CGACTCACTATAGGGACCATGTAAGTTTTTCTTGCTATTGTC (SEQ ID NO: 27)/ GACAATAGCAAGAAAAACTTACATGGTCCCTATAGTGAGTCG (SEQ ID NO: 28) |
| T106G | GTCCAAGACTATCTTTATCTAGGTCCACAAGATTGGTAACTG (SEQ ID NO: 29)/ GTCCAAGACTATCTTTATCTAGGTCCACAAGATTGGTAACTG (SEQ ID NO: 30) |
| T106G_A77C | GTTTTTCTTGCTATTGTCATCTGGATAAGTCCAAGACTATC (SEQ ID NO: 31)/ GATAGTCTTGGACTTATCCAGATGACAATAGCAAGAAAAAC (SEQ ID NO: 32) |
| A89T | GCTATTGTCATATGGATAAGTCCTAGACTATCTTTATCTATGTCCAC (SEQ ID NO: 33)/ GTGGACATAGATAAAGATAGTCTAGGACTTATCCATATGACAATAGC (SEQ ID NO: 34) |
| C97G | GGATAAGTCCAAGACTATGTTTATCTATGTCCACAAGATTGG (SEQ ID NO: 35)/ CCAATCTTGTGGACATAGATAAACATAGTCTTGGACTTATCC (SEQ ID NO: 36) |
| Motif1+ | GCTATTGTCATATAGGATAAGTCCAAGACTATCTTTATCTTATGTCCAC (SEQ ID NO: 37)/ GTGGACATAAGATAAAGATAGTCTTGGACTTATCCTATATGACAATAGC (SEQ ID NO: 38) |
| Motif1- | CTATTGTCATAGGATAAGTCCAAGACTATCTTTATCTTGTCCACAAG (SEQ ID NO: 39)/ CTTGTGGACAAGATAAAGATAGTCTTGGACTTATCCTATGACAATAG (SEQ ID NO: 40) |
| HCV X-region | TAATACGACTCACTATAGGTGGCTCCATCTTAGCCCTA (SEQ ID NO: 41)/ ACTTGATCTGCAGAGAGGCCAGTATCA (SEQ ID NO: 42) |
| HCV PolyU/UC | TAATACGACTCACTATAGGCCATCCTGTTTTTTTCCC (SEQ ID NO: 43)/ AAAGGAAAGAAAAGGAAAAAAAGAGG (SEQ ID NO: 44) |
| X-region_DVG70-114 R[a] | TTGTGGACATAGATAAAGAT AGTCTTGGACTTATCCATATGACAAACTTGATCTGCAGAGAGGCCAGTATCA (SEQ ID NO: 45) |
| X-region_DVG5-51 R[a] | GAAGACAAGAAAATTTAAAAGGATACATATCTCTTAAACTCTTGTCACTTGATCTGCAGAGAGGCCAGTATCA (SEQ ID NO: 46) |
| DVG-324 | GGTGAGGAATCTATACGTTATAC (SEQ ID NO: 47)/ CCTCAGGTTCCTGATCTC (SEQ ID NO: 48) |

TABLE 2-continued

Primers(SEQ ID NOS 25-52, respectively, in order of appearance) used in mutagenesis and mutant verification

| Primers | Forward/reverse primers (5' to 3') |
|---|---|
| DVG-354 | GGTGAGGAATCTATACGTTATAC (SEQ ID NO: 49)/<br>CCTCAGGTTCCTGATCTC (SEQ ID NO: 50) |
| DVG Comp | ACCAGACAAGAGTTTAAGAGATATG (SEQ ID NO: 51)/<br>AGCAAGAAAAACTTACAAGAAGACA (SEQ ID NO: 52) |

[a]Only the reverse primer sequence is provided here. Use HCV X-region Forward primer for pairing the mutagenesis.

Infection with rDVG-324 stimulated significantly higher levels of IFN-β1 and IFIT1 mRNA expression in LLC-MK2 cells than did infection with rDVG-354, while the viral protein and DVG RNA expression levels were equivalent (FIG. 9C). These data show that $DVG_{70-114}$ functions to enhance the antiviral response during infection, demonstrating its biological relevance.

To further evaluate whether $DVG_{70-114}$ promotes antiviral immunity in the presence of a virus-encoded antagonist, cells were infected with SeV LD 24 h before transfection with either DVG-268 or $DVG-268_{\Delta 70-114}$. By the time of DVG RNA transfection, viral protein mRNA, including NP and P/V, had accumulated to high levels in the cells (FIG. 9C) and no antiviral gene expression was detected (FIG. 9D, NT [nontransfected]). Agreeing with their predicted stimulatory potential, transfection of DVG-268 resulted in the strong expression of antiviral genes while $DVG-268_{\Delta 70-114}$ maintained its reduced stimulatory potential under these conditions (FIG. 9D). These data further demonstrate that $DVG_{70-114}$ has strong immunostimulatory activity even in the presence of potent viral antagonists of detection.

Figure 10A:
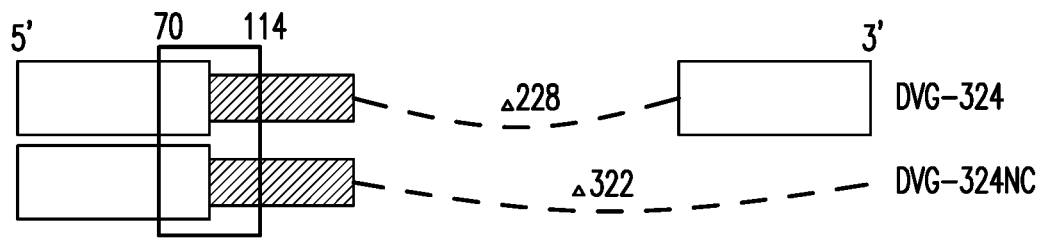
FIG. 10A-FIG. 10H. 3'-5' complementarity and additional secondary structures are not necessary for IFN induction by DVG-derived RNA.
Figure 10B:
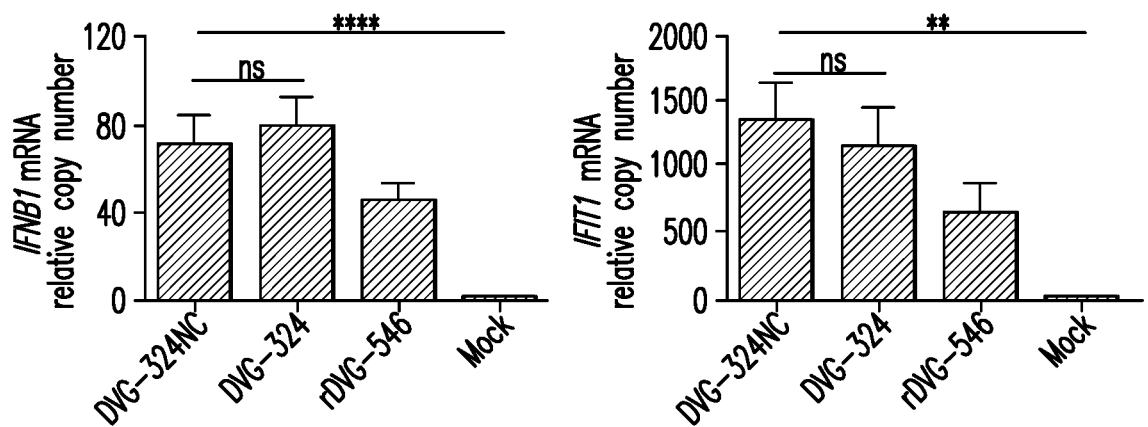

Example 5: The 3' Complementary End of iDVG RNA is not Required for Maximal IFN Induction Contrary to previous implications, the data strongly suggest that complementarity along the 5' and 3' ends of copy-back DVGs is not a requirement for strong stimulatory activity. To directly test if the 3'-complementary sequence is essential, the complete 3'-complementary sequence (94nt) from DVG-324 (FIG. 10A; DVG-324NC; SEQ ID NO:6) was deleted. Upon transfection, DVG-324NC induced the same level of expression of antiviral genes as the parental DVG-324, and both mutants showed higher potency than DVG-546 (FIG. 10B). As expected, the potent stimulatory activity of DVG-324NC depended on the $DVG_{70-114}$ motif as a $DVG-324NC_{\Delta 70-114}$ mutant significantly lost stimulatory potential (FIGS. 10C, 10D, and 10F).

Figure 10C:
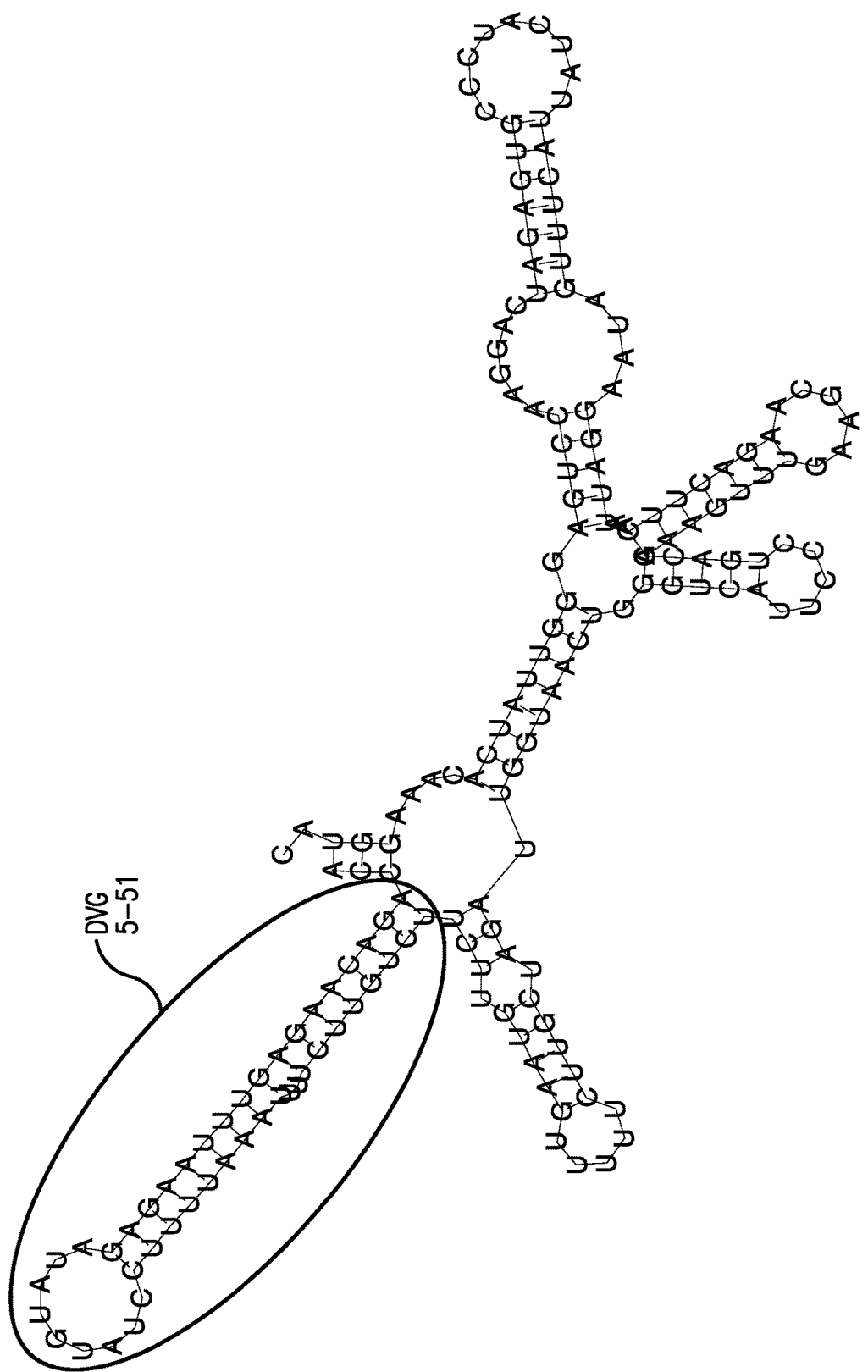
Figure 10C:
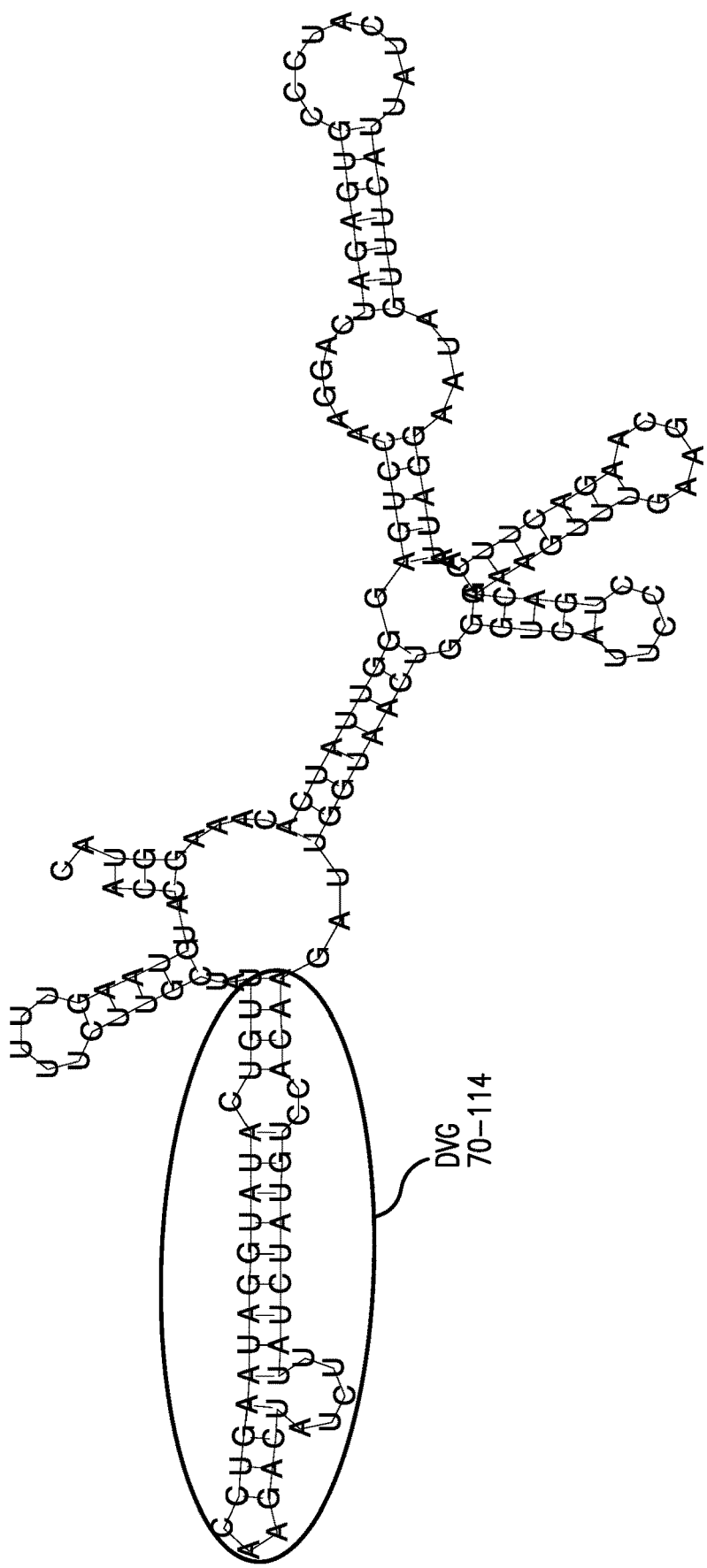
Figure 10D:
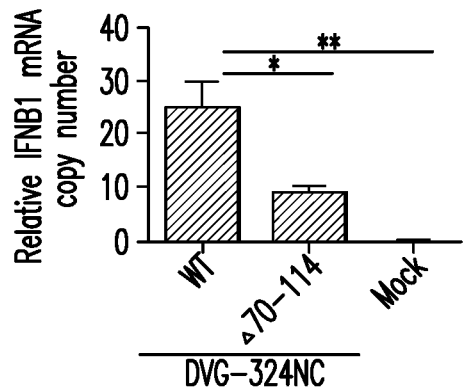
Figure 10E:
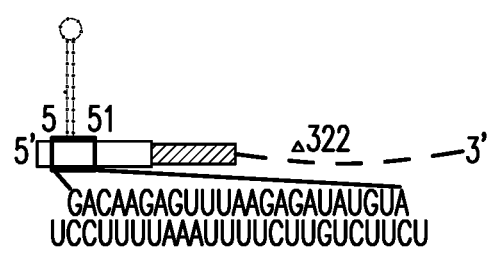
Figure 10F:
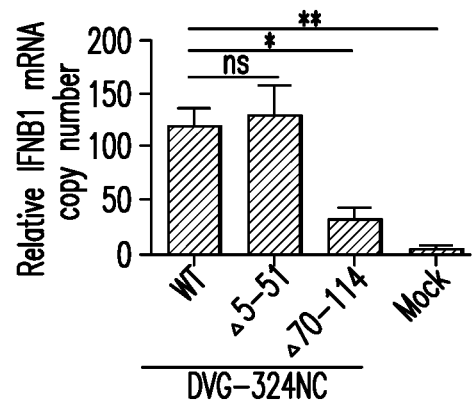

To control for the role of additional secondary structures in the stimulatory activity of DVG-324NC, an auxiliary secondary motif ($DVG_{5-51}$) located more proximal to the 5'-triphosphate end of RNA in relation to $DVG_{70-114}$ was next removed (FIG. 10C—blue circle and 10E). This motif is also preserved in all DVG mutants shown in FIG. 4. Deletion of $DVG_{5-51}$ in DVG-324NC did not affect the integrity of $DVG_{70-114}$ or the overall structure of the DVG (FIG. 10C) and did not impact the stimulatory activity of DVG-324NC (FIG. 10F). Overall, these data demonstrated that $DVG_{70-114}$ enhances the immunostimulatory activity of DVG RNA and functions independently of the 3'end complementary sequence or additional proximal secondary structures.

Example 6: Stabilization of $DVG_{70-114}$ Enhances its Stimulatory Potential

Figure 8E:
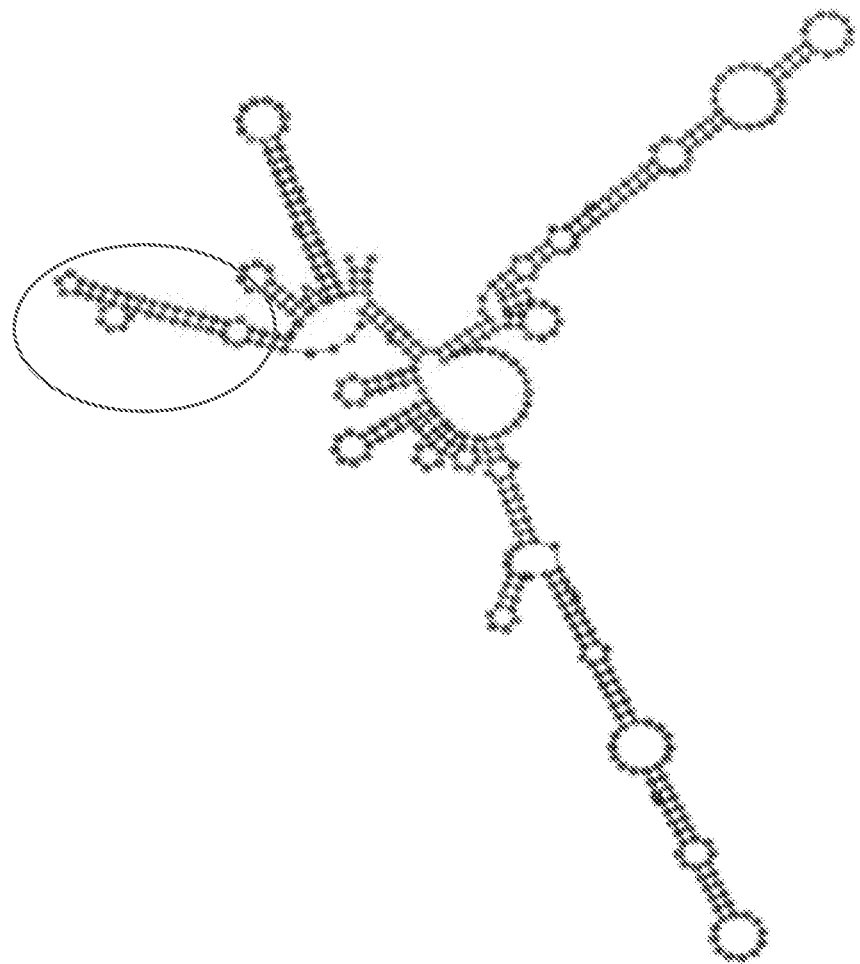
Figure 8E:
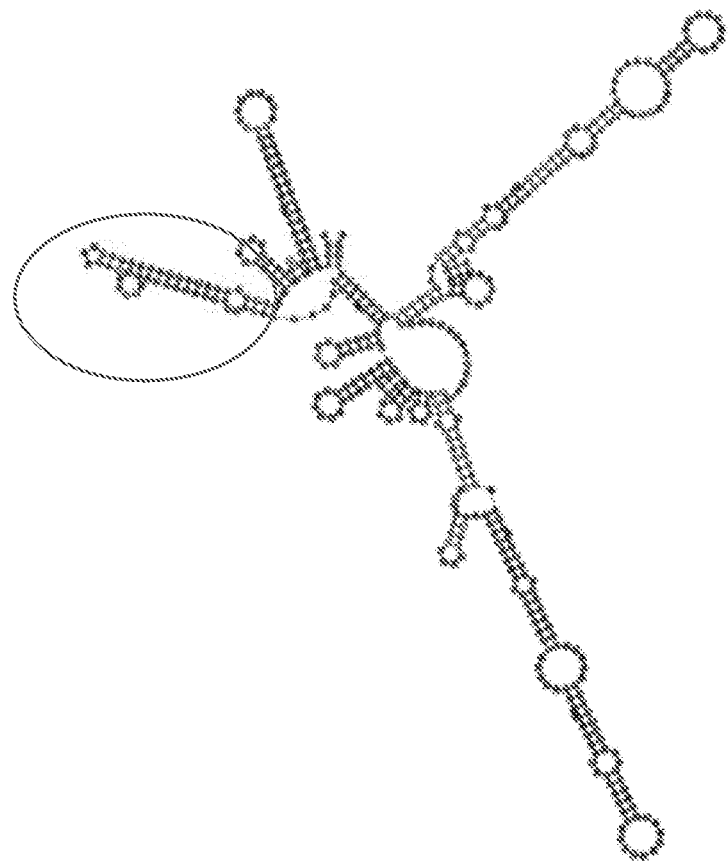
Figure 8F:
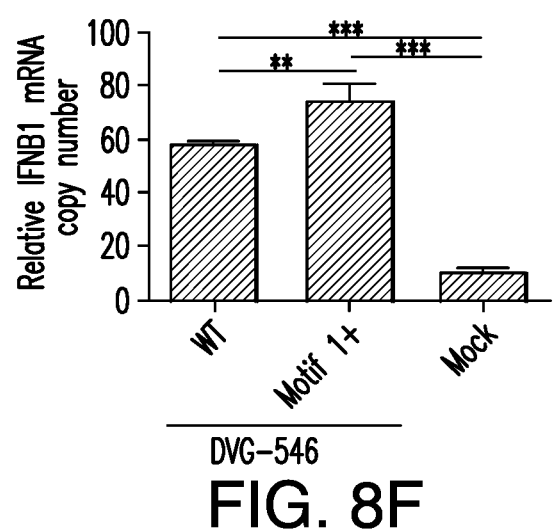
Figure 10G:
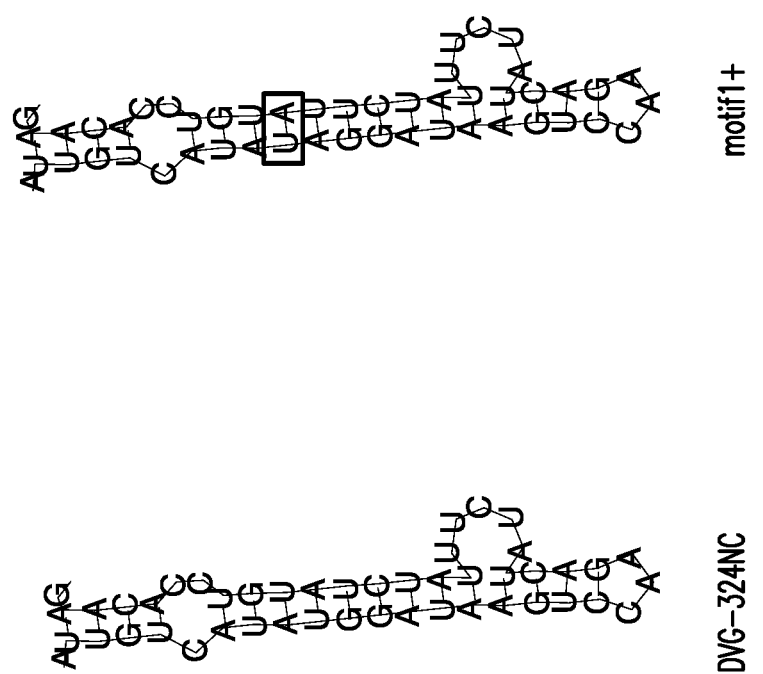
Figure 10H:
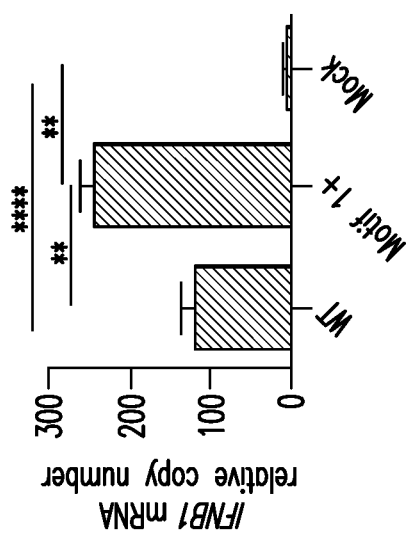

It was next evaluated whether modifying the $DVG_{70-114}$ motif could further optimize the stimulatory activity of DVG-derived RNAs. To do this, an additional A-U base pair was introduced into the $DVG_{70-114}$ long stem region of the DVG-324NC background. This insertion stabilized the stem structure as it increased its minimal free energy from −9.8 kcal/mol to −10.89 kcal/mol (FIG. 10G; $DVG-324NC_{motif-}$). Cells transfected with $DVG-324NC_{motif+}$ RNA expressed two-fold higher levels of IFNB1 and IFIT1 mRNA than cells transfected with unmodified DVG-324NC (FIG. 10H and data not shown) demonstrating that stabilization of $DVG_{70-114}$ motif improves its immunostimulatory potential. The stimulatory enhancement potential of stabilizing $DVG_{70-114}$ was further validated in DVG-546 (FIGS. 8E and 8F).

Figure 11A:
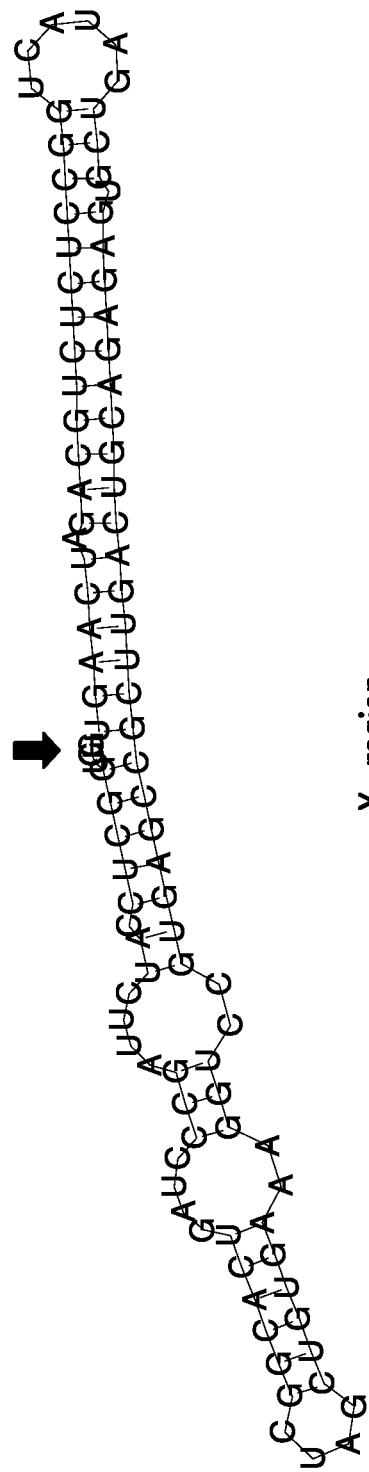
FIG. 11A-FIG. 11B. DVG$_{70-114}$ motif transfers strong immunostimulatory activity to inert RNA molecules.
Figure 11A:
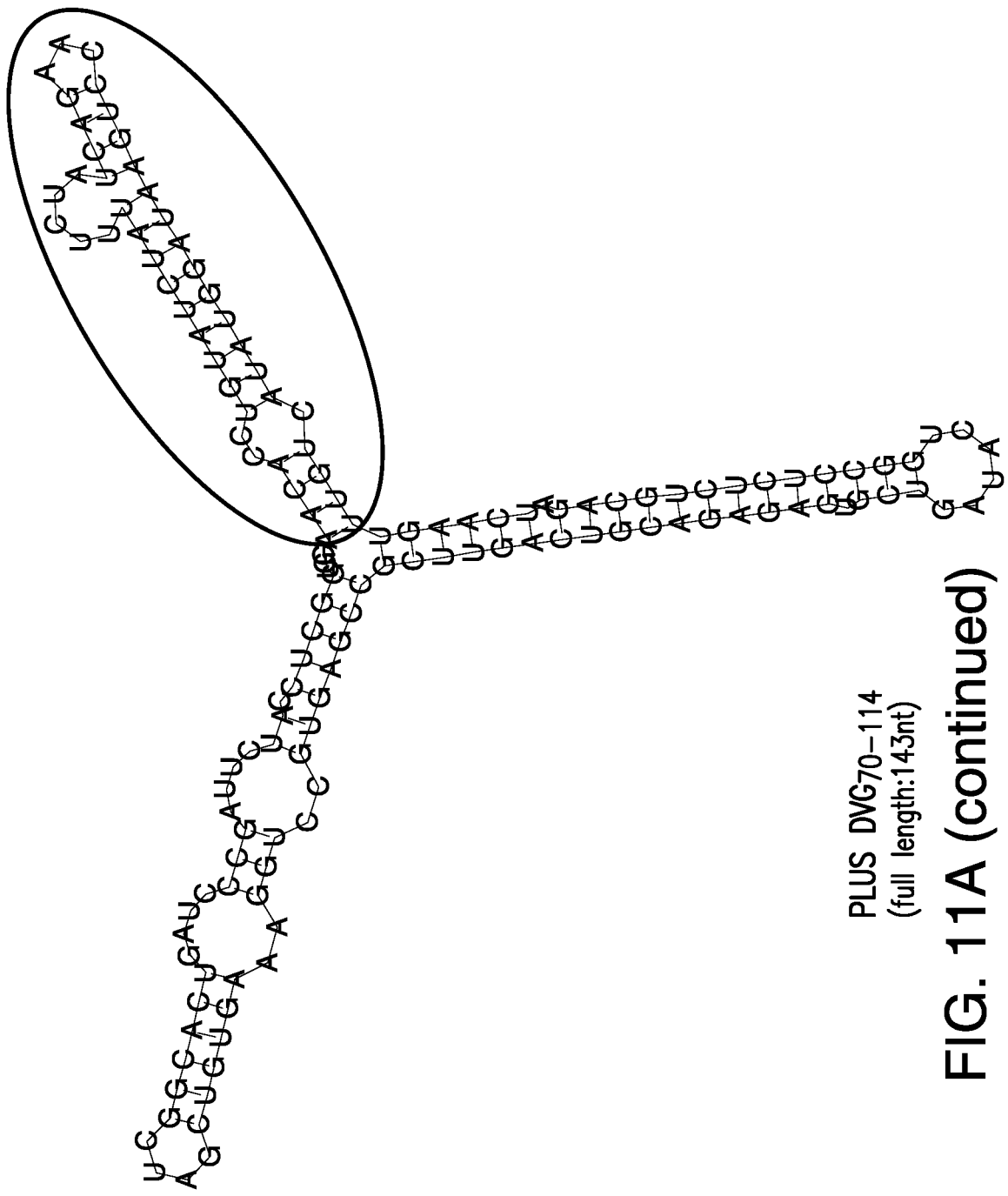
Figure 11A:
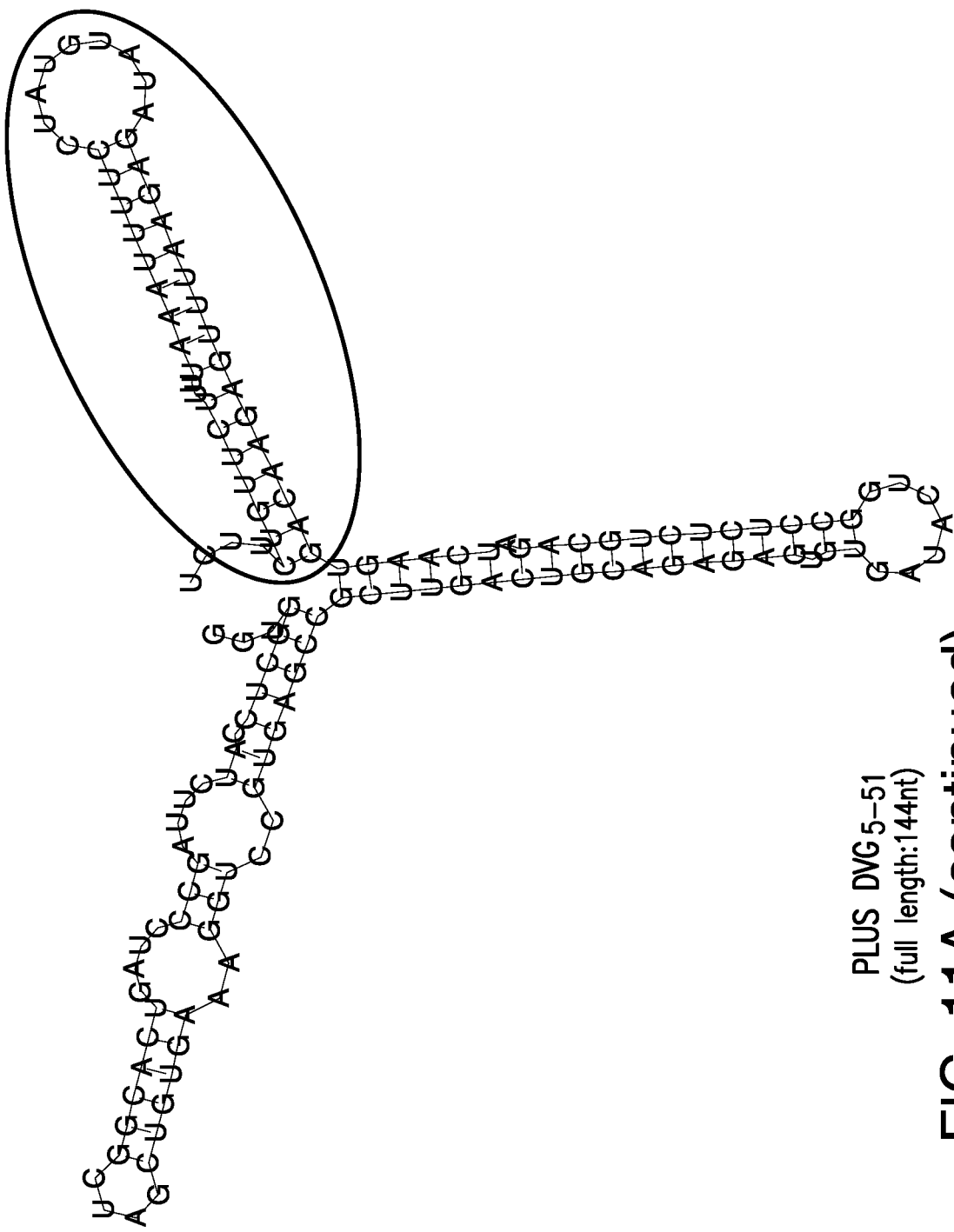
Figure 11B:
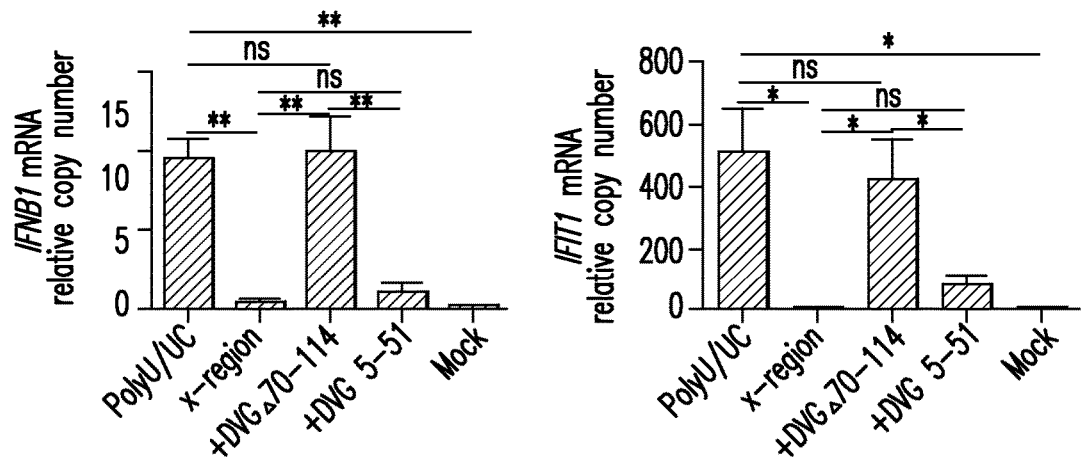
Figure 12A:
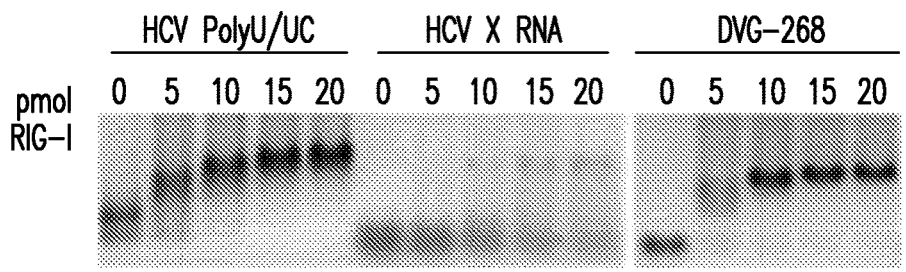
(FIG. 12A) EMSA of 6 pmol HCV poly U/UC, X-region and DVG-268 in the presence of ATP and increasing doses (0-20 pmol) of full length RIG-I. Product was resolved on a 2% agarose gel.
Figure 12B:
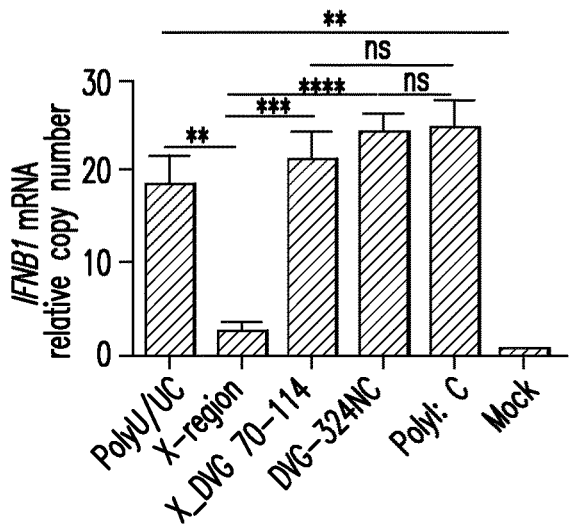
(FIG. 12B and FIG. 12C) Expression of IFNB1 and IFIT1 mRNA measured by RT-qPCR from LLC-MK2 cells transfected for 6 h with 4.15 pmol ivtDVGs or equivalent amounts of HCV poly U/UC, X-region or poly I:C (HMW). Data correspond to the mean±SEM of all experiments (total n=3/group). *p<0.05, p<0.01, *p<0.001, ****p<0.0001 by one-way ANOVA with Bonferroni post hoc test. Data are expressed as copy numbers relative to the housekeeping gene GAPDH.
Figure 12C:
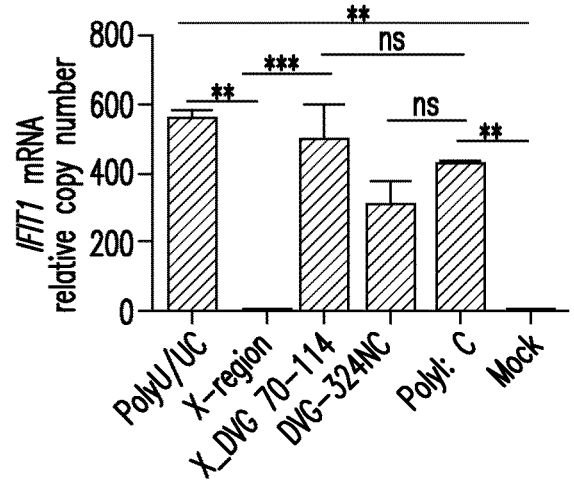

Example 7: $DVG_{70-114}$ Motif Confers Strong Immunostimulatory Activity to Inert RNA Molecules To assess if the immunostimulatory activity of $DVG_{70-114}$ could be transferred to inert 5'triphosphate-containing RNA molecules, the $DVG_{70-114}$ motif was cloned into the X-region from hepatitis C virus (HCV), a well-described non-immunostimulatory small RNA derived from the virus genome (13). The cloning strategy preserved the RNA stem-loop structures present in both the $DVG_{70-114}$ motif and the X-region (FIG. 11A). Remarkably, transfection of the ivtRNA X-region_$DVG_{70-114}$ (X-region based mutant that includes $DVG_{70-114}$) lead to pronounce induction of IFNB1 and IFIT1 mRNA compared to the X-region alone (FIG. 11B). X-region $DVG_{70-114}$ also demonstrated an equivalent ability to stimulate antiviral gene expression when compared with HCV polyU/UC (13) (FIG. 1B). To rule out the possibility that the potent activity of X-region_ $DVG_{70-114}$ resulted from adding an additional stem loop structure, independently of the sequence of the motif, the inventor also cloned into the X-region the auxiliary $DVG_{5-51}$ motif (FIGS. 10C and 10F). As mentioned previously, $DVG_{5-51}$ motif is not required for immunostimulatory activity of DVG RNA. $DVG_{5-51}$ is of a similar size as $DVG_{70-114}$ and causes equivalent disruption of the X region folding (FIG. 11A). Introduction of the $DVG_{5-51}$ motif did not alter the stimulatory activity of the X-region (FIG. 11B) demonstrating that $DVG_{70-114}$ has exceptional and transferrable immunostimulatory potential.

The activity of DVG RNA was compared with that of other known RIG-I ligands. As shown in FIG. S5A, DVG-derived RNA binds to RIG-I with an affinity equivalent to that of poly(U/UC) and RNA containing $DVG_{70-114}$ stimulates levels of antiviral expression equivalent to that of poly(U/UC) or the viral RNA synthetic analog poly(I-C) (see FIGS. S5B and C).

Example 8: The $DVG_{70-114}$ Motif Promotes Binding of the RNA to RIG-I

Figure 14:
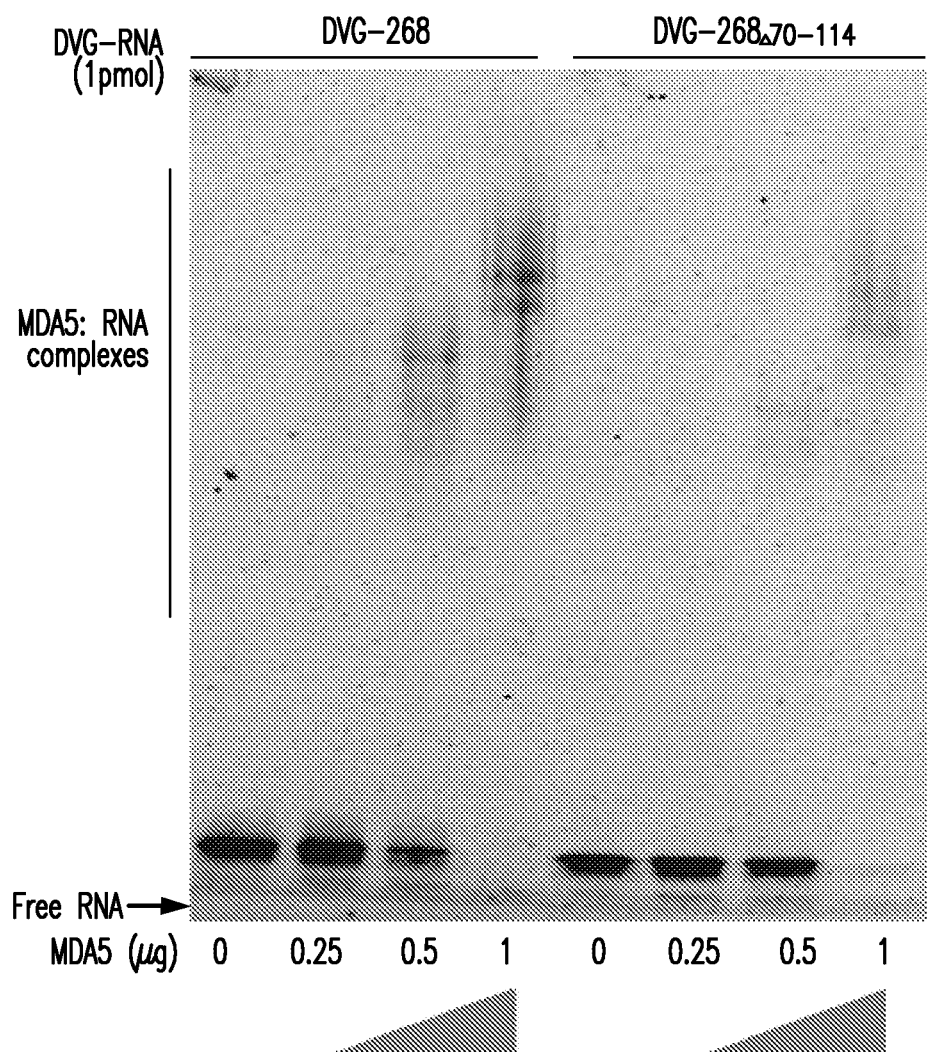
FIG. 14. DVG$_{70-114}$ improves the binding of DVGs to MDA5. EMSA of DVG-268 and DVG-268Δ70-114 RNA in the presence of increasing doses of MDA5 delta CARD.

To establish whether the strong stimulatory activity of DVG-268 and DVG-324NC were mediated by RIG-I, these constructs were transfected into mouse embryo fibroblast lacking the essential RLR signaling molecule MAVS or lacking the RIG-I sensor. Similar to other DVG constructs (26), Ifnb1 mRNA expression was completely dependent on MAVS and RIG-I activity for both mutants (FIG. 13A), while control polyI:C showed only MAVS, but not RIG-I dependency. In addition, Ifnb1 stimulation was largely dependent on the presence of uncapped 5'-triphosphates (FIG. 13B) and on RNA secondary structures (FIG. 13C). To determine if the $DVG_{70-114}$ motif augmented the binding of DVG RNA to RIG-I, electrophoretic mobility shift assay (EMSA) was performed on DVG-RNA exposed to purified RIG-I proteins that lacked the signaling (CARD) domain. Binding was tested in both the absence or presence of ATP, which promotes RIG-I polymerization upon association to RNA. RIG-I deltaCARD was used previously in characterizing specific RNA binding signatures and demonstrated equivalent RNA binding affinity as their full-length parental protein (10, 36). RNAs containing the $DVG_{70-114}$ motif were more profoundly displaced in the gels than RNAs lacking this motif both in the absence and presence of ATP (FIGS. 13D and 13E). These data indicate a stronger capacity of RNA containing the $DVG_{70-114}$ motif to promote RIG-I binding and polymerization, essential events in RLR signaling (37-39). In addition, a slight enhancement in the binding capacity of RNAs containing the $DVG_{70-114}$ motif to MDA5 deltaCARD was observed (FIG. 14), supporting previous reports of a supplementary role for MDA5 in the sensing of DVGs (34). Together, these results demonstrate that $DVG_{70-114}$ facilitates the binding of RNAs to RLRs and is critical for effective triggering of RIG-I signaling in response to SeV DVGs.

Example 9: $DVG_{70-114}$ has Immunostimulatory Activity In Vivo

C57BL6 mice were treated intranasally (i.n.) with 30 ul of PBS (mock) or 4 μg of polyI:C, DVG-324NC or DVG-324NC$_{A70-114}$. See FIG. 15. Expression of the antiviral gene Mx1 in whole lung homogenates collected 6 hpi and RNA in situ hybridization on lungs extracted 6h after inoculation of DVG-324NC indicates that nasal delivery of the $DVG_{70-114}$ motif in vivo results in the delivery of the motif to the lungs. This indicates that the RNA motif is stable within the subject and that nasal administration is appropriate. Importantly, it demonstrates that RNAs containing this motif are active in triggering antiviral immunity when administered this way.

Discussion

SeV iDVG-derived RNAs are natural RLR ligands that potentiate host antiviral innate immune responses (12, 26). The inventor has discovered an RNA secondary structure ($DVG_{70-114}$) that significantly enhances the activity of inert RNA and provides outstanding immunostimulatory activity.

$DVG_{70-114}$ folds into a stable stem-loop motif in the positive sense strand of the SeV DVGs. Folding predictions of the negative sense of the molecule failed to predict the formation of a similar structure (not shown) corresponding with the observed strong correlation between the enhanced relative accumulation of (+)DVG in infected cells and type I IFN expression. These observations demonstrate that in addition to the conventional 5'-triphosphate motif, sequences and/or structures present only in the (+) sense of the molecule maximize its immunostimulatory potential.

The $DVG_{70-114}$ stem-loop motif shares little sequence homology with the standard viral genome, as it forms in the copy-back iDVG's "junction region" where the polymerase starts extending (or copying back) the nascent strand after been released from the template strand (12, 43, 44). Similar stem-loop structures are found in other copy-back DVGs generated during infection with SeV strains Cantell and 52 (data not shown), suggesting that this structure is broadly present during SeV infection.

Without being bound by theory, the immunostimulatory activity of $DVG_{70-114}$ appears to depend on both its structure and sequence. Point mutation analyses demonstrated tolerance to nucleotide swaps at the most distal tip of the motif (A89U) while nucleotide stringency was shown in mutation at the bulge (C97G) and some areas of the stem (U106G). In addition, the data demonstrated that the 3'-complementary sequence is not required for the iDVG stimulatory activity. DVG-324NC (DVG-324 lacking the 3'-complementary sequence) induced IFN expression equal to DVG-324 and this activity depended on an intact $DVG_{70-114}$. This result contradicts a previous study that shows a requirement for both 5' and 3' complementary sequences for the maintenance of SeV DVGs immunostimulatory functions (35). The disparity likely results from an unexpected impact of truncations of the complementary region on the structure of the $DVG_{70-114}$ motif leading to a misinterpretation of the need for the complementary region.

Remarkably, the insertion of $DVG_{70-114}$ but not of $DVG_{5-51}$ into the inherently inert X-region of HCV conferred strong immunostimulatory activity to this molecule, comparable to that of the well-characterized polyU/UC region. These data demonstrate that $DVG_{70-114}$ retains its stimulatory potential even outside of the context of iDVGs. Previous studies demonstrated that 5'-triphosphates were necessary for non-self recognition of SeV iDVG by RIG-I (24). Here it is shown that 5'-triphosphates are not sufficient and that optimal recognition occurs only in the presence of $DVG_{70-114}$, as mutants DVG-IS and DVG-200 maintain their 5'triphosphate but do not stimulate RLR signaling. Here it is reported that $DVG_{70-114}$ facilitates the binding of the iDVG to RIG-I explaining its strong ability to trigger the antiviral response. In addition, a role for $DVG_{70-114}$ in enhancing binding of MDA5 to DVG RNA observed, supporting previous findings of a role for MDA5 in the early detection of SeV iDVGs (34).

The role of DVGs in promoting strong antiviral responses during infection with a number of viruses has been documented since the 1970s, (23) and most recently it was shown that DVGs occurring naturally in the lung during SeV infection drive the antiviral response in vivo (24). Facilitated binding to RLR by $DVG_{70-114}$, together with the faster accumulation of DVGs over the standard virus genome in infected cells (24), likely explain the ability of DVGs to overcome viral antagonism of the immune response.

In summary, a molecular motif has been identified that facilitates the activation of the antiviral immune response by enhancing the binding of RNAs to the intracellular viral sensor protein RIG-I. Importantly, this motif can be harnessed to maximize the immunostimulatory activity of uncapped 5'triphosphate-containing RNAs and thus it represents a novel immunostimulatory enhancer that can be used in the development of vaccine adjuvants or antivirals.
Materials and Methods Cell Lines and Viruses LLC-MK2 cells (Rhesus monkey kidney epithelial cells, ATCC, # DR-L2785), A549 cells (human type II alveolar cells, ATCC, # CCL185), and wild type, Ddx58$^{-/-}$ (RIG-I$^{-/-}$) and Mavs$^{-/-}$ MEFs (mouse embryo fibroblast, kindly provided by Drs. J. Kagan and J. Chen) were cultured in DMEM supplemented with 10% fetal bovine serum, 1 mM sodium pyruvate, 2 mL L-Glutamine, and 50 mg/ml gentamicin or penicillin and streptomycin (all from Invitrogen). All cell lines were treated with mycoplasma removal agent (MP Biomedicals) before use. SeV Cantell HD (SeV-HD; high DVG particle content) was prepared in embryonated hen eggs as described previously (25).

Plasmids and Constructs

A plasmid expressing DVG-546 flanked at the 3' end by the SpeI-T7 promoter sequence and at the 5' end by the hepatitis delta virus ribozyme and the T7 polymerase terminator sequence was prepared as described previously (26). To generate DVG mutants, restriction enzyme sites were introduced into the construct using the QuickChange II XL site-directed mutagenesis kit (Agilent Technologies). Specifically, DVG-268 was generated by the introduction of 6 nucleotides to generate a KpnI site at position 163 of the DVG-546 sequence. A second KpnI site at position 448 of the wild type DVG internal sequence allowed the deletion of 228 nucleotide-long fragment of the DVG. DVG-324 and DVG-354 were generated as previously described (26). DVG-324NC was generated by introduction of a second KpnI site at position 330 of the DVG-324 sequence allowing the deletion of a 100 nucleotide-long fragment between positions 230 and 330 of the DVG-324 sequence. Motif DVG$_{70-114}$ and DVG$_{5-51}$ deletions, single nucleotide swaps (T106G, A89U, C97G), and nucleotides additions (motif1+) were generated by site-directed mutagenesis (QuikChange XL II, Agilent Technologies). For nucleotide swaps, primers introduced T/G mutations at position 89, 97 or 106 of the DVG-268 sequence. Motif1+ includes an A insertion after position 78, and a T insertion after position 104 of the DVG-324NC sequence. Sequences for all mutagenesis primers are shown in FIG. 21. Poly U/UC and X-region plasmids were kindly provided by Dr. M. Gale (University of Washington).

HCV PAMP Preparation and Manipulation

DNA sequences bearing PolyU/UC or X-region were amplified by PCR (X-region for 5'-TAATACGACTCAC-TATAGGTGGCTCCATCTTAGCCCTA-3' (SEQ ID NO: 41), X-region rev 5'-ACTTGATCTGCAGAGAGGCCAG-TATCA-3' (SEQ ID NO: 42); HCV polyU/UC for 5'-TAATACGACTCACTATAGGCCATCCT-GTTTTTTTCCC-3' (SEQ ID NO: 43); HCV polyU/UC rev 5'-AAAGGAAAGAAAAGGAAAAAAAGAGG-3'(SEQ ID NO: 44)) using a high fidelity polymerase (Invitrogen). X-region mutants bearing DVG motifs were constructed by adding DVG motifs at the 3' end of molecule by PCR using the primers shown in FIG. 22. The resulting PCR products were gel-purified (QIAGEN) and subjected to in vitro transcription as described below.

ivtDVG Preparation

DVG-expressing plasmids were linearized and in vitro transcribed using the MEGAscript T7 kit (Ambion) in the presence of RNase inhibitor (Fermentas). RNA products were treated with DNase followed by LiCl precipitation. OD260/280 ratios of all ivtDVG were between 2.00 and 2.25 and OD260/230 between 2.20-2.60. The integrity of ivtDVG was analyzed in an Agilent Bioanalyzer 2100. Endotoxin level of all ivtDVG used in this study was tested by the Biomedical Research Core Facility, University of Pennsylvania and was reported to be below 1.2 EU/100 μg for all ivtDVG RNA preparations and <0.36 EU/100 μg for all HCV polyU/UC and X-region mutant ivtRNA preparations. As an additional control all ivtDVGs were gel-purified on 5% Urea-TBE gel and transfected into LLC-MK2 cells at the same molarity (4.15 pmol). Purified ivtDVGs had essentially identical activity than the non-purified ivtDVGs used to gather most of the data. Purified PCR products were used for in vitro transcription of PolyU/UC or X-region RNA using the MEGAscript T7 kit (Ambion) in the presence of RNase inhibitor (Fermentas).

RNA Treatments and Transfection

To remove 5'-triphosphates, 1 μg of ivtDVG was incubated with 10 U of Alkaline Phosphatase (AP, Thermo Scientific) for 60 min at 37° C. To cleave single stranded RNA, 1 μg of RNA was incubated with 1 ng of RNase A (Ambion) for 15 min at room temperature. To cleave double stranded RNA, RNA was incubated with 0.1 U of RNase V1 (Ambion) for 15 min at room temperature. After treatments, RNA was purified using TRIzol or precipitation/inactivation buffer according to the manufacturer's specifications. AP and RNase dual treatment was accomplished by incubating AP treated ivtDVG with RNases following same protocol mentioned above. Prior to transfection, RNAs were heated at 65° C. for 5 min, cooled down to room temperature for 5 min, and then chilled on ice to promote proper folding of the molecules before transfection into cells. 4.15 pmols of the structured RNAs were transfected into cells ($2.5 \times 10^5$) using Lipofectamine 2000 (Invitrogen). As controls, cells were transfected with equally molarity of High Molecular Weight (HMW) Poly I:C (InvivoGen).

Secondary Structure in Silico Prediction

DVG RNA folding was predicted using RNAfold server from the Vienna RNA package v.2.1.8 (rna.tbi.univie.ac.at/cgi-bin/RNAfold.cgi. University of Vienna) (46). For analysis default parameters were applied for minimum free energy (MFE) and partition functions fold algorithms (Turner model, 2004). The optimal secondary structure with minimum free energy of the thermodynamic ensemble is shown for each DVG RNA prediction.

Quantitative RT-PCR (RT-qPCR)

RT-qPCR was performed as previously described (24). Briefly, 1 μg of RNA was reverse transcribed using High Capacity RNA-to-cDNA kit (Applied Biosystems). qPCRs were performed using SYBR Green PCR Master Mix (Applied Biosystems) in a Viia7 Applied Biosystems Lightcycler. Primers used can be found in FIG. 22.

RNA Fluorescent In Situ Hybridization (FISH) and Immunofluorescence Assay (IFA)

Probes complementary to the positive sense (+) of the SeV genome were designed against the full-length genome (from position 1 to 11630) excluding the 5' end that encompasses the DVG sequence. A pool of 32 oligos targeting the (+) SeV genome was designed by Dr. Arjun Raj as previously described (47). These probes recognize (+) viral genome as well as all viral-encoded mRNAs. For probes identifying DVGs, a pool of 15 single-stranded 20 nucleotides-long oligos specific for the 3' end of the (+) SeV genome (from position 14965 to 15416) which covers the DVG sequences was designed using same methods. These probes will bind to DVGs, viral L protein mRNA, and (+) SeV genome. In both pools, oligos were complementary to a different region of the target RNA, with no less than two bases separating any two oligonucleotides. SeV genome probes were labeled with Quasar 570 and DVG probes were labeled with Quasar 670 (Biosearch Technologies). Since L protein mRNA and (+) SeV genome are recognized by both set of probes, pixels containing both colors were considered a representation of SeV genome/protein. Pixels only stained with Quasar 670 (pseudocolored green) represent (+) DVGs. For FISH, cells were plated onto plain glass coverslips (Fisher Scientific) at a density of $1 \times 10^6$ cells/well and grown overnight at 37° C. RNA-FISH was performed according to published protocols with minor modifications (48). Briefly, $2.5 \times 10^5$ LL-CMK2 cells were transfected with 4.15 pmol of ivtDVG RNA using Lipofectamine 2000. At different times after transfection the cells were washed with phosphate buffer saline (PBS), followed by fixation with 4% formaldehyde for 10 min at room temperature (RT). Fixed cells were then permeabilized with 70% ethanol for 1 h at RT. Permeabilized cells were incubated with anti-human IRF3 antibody (Santa Cruz, 1:100 dilution) followed by Alexa Fluor 594-labeled goat anti-rabbit IgG (Invitrogen, 1:500 dilution) diluted in 1% bovine albumin in presence of 40 U/ml RNase inhibitor (Invitrogen). Stained cells were incubated in 4% formaldehyde for 10 min prior to FISH and then washed with PBS and equilibrated in wash buffer containing 10% formamide and 2× saline sodium citrate (SSC). FISH was performed by hybridizing fixed cells with 10 nM of probes diluted in hybridization buffer consisting of 10% formamide, 2×SSC, and 10% dextran sulfate (w/v). Hybridization was performed overnight in a humidified chamber at 37° C. Imaging acquisition was performed on Nikon E600 Epifluorescent microscope equipped with a 100×, 1.4 numerical aperture (NA) oil-immersion objective (Zeiss) and a Zeiss AxiCam MRm camera.

FISH-IFA Image Quantification

Imaging quantification was performed using Volocity Quantitation module (Perkin-Elmer) (49). Exposure time, gain, and offset were held constant for all images. The fluorescent signal from the nuclei of cells was selected by drawing a region of interest (ROI) around each nucleus. The fluorescent signals of the (+)DVG was determined by drawing an ROI around the entire cell and following the same procedure as described above. The average ROI intensity of IRF3 and (+)DVG signals in mock infected cells was measured and used as reference to set threshold for defining nuclear IRF3 and (+)DVG positive cells. Nuclear IRF3 positive cells among (+)DVG positive populations were identified by performing "intersect module" while the nuclear IRF3 positive cells among (+)DVG negative populations were identified by the performing "exclude touching" module. For the analysis, at least 250 cells were quantified in each experimental group through three independent experiments.

Electrophoretic Mobility Shift Assay (EMSA)

RIG-I_deltaCARD and MDA5_deltaCARD protein (RIG-I or MDA5 without the two N-terminal CARDs) were kindly provided by Dr. Sun Hur (Harvard, Boston, Mass.) and were prepared as described elsewhere (36). EMSA was performed by incubating ivtRNA with 1 µg or indicated amount RIG-I_deltaCARD or MDA5_deltaCARD protein in buffer A (20 mM HEPES (pH 7.5), 150 mM NaCl, 1.5 mM MgCl2, and 2 mM dithiothreitol [DTT]) for 15 min at 37° C., and the complex was analyzed on 4-12% Bis-Tris NativePAGE (Bio-Rad). Gels were stained with SYBR Gold (Life Technologies), and fluorescent gel images were recorded and analyzed using a Gel Doc XR+ imaging system (Bio-Rad).

Statistical Analysis

Statistical analyses were performed using GraphPad Prism version 5.0. GraphPad Software, San Diego, Calif., USA. www.graphpad.com. A statistically significant difference was defined as a P value of <0.05 by either One-way ANOVA or Student's t test with or without post hoc test as indicated in each figure based on specific data set.

Example 10: DVG-Derived RNA Acts Synergistically with MF59 to Enhance Immunostimulatory Activity MF59 is an Adjuvant produced by Norvartis that is licensed for vaccines used in humans in Europe and others parts of the world, approved by the FDA for use in the USA in influenza vaccines for the elderly. It is an emulsion and presumably facilitates the delivery of the antigen to the target cells. It also has a mild immunostimulatory potential.

Samples for immunization were formulated with (in ratio of) 1 µg DVG, 40 µl MF59, 0.6 µg IAV Cal/09 HA protein as antigen per mouse/dose. In this experiment we used DVG-268 was used. Briefly, 1 µg DVG-268 was diluted in water, heated at 65 degree for 5 min and put on ice for 2 min to restore correct folding of the RNA. Then 40 µl of MF59 and 0.6 µg of IAV Cal/09 HA protein were mixed into the samples to get the complete formulation. Samples were kept in 4 degree before i.m.

Figure 23:
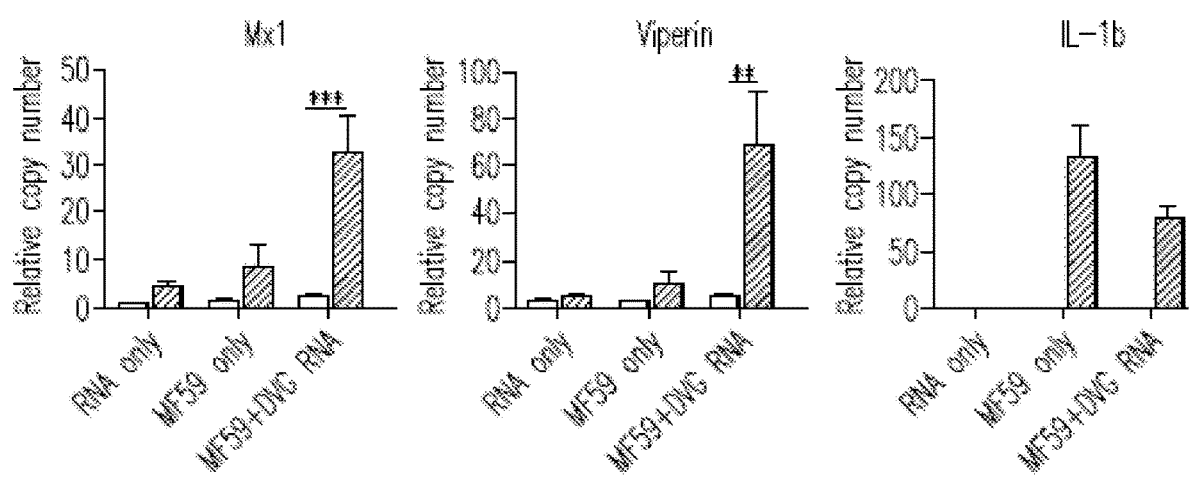
FIG. 23. Expression of various antiviral genes mRNA in tissue homogenate by RT-qPCR. Data are shown as mRNA copy number relative to house keeping gene Rps11 and Gapdh. ***<0.001 by Two way-ANOVA with Bonferroni pos-hoc test. ns=non-significant. n=5.
Figure 24:
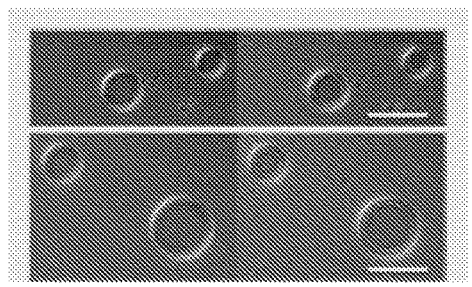
FIG. 24. DVG and MF59 complexes synergistically stimulate the innate immune response. Confocal microscopy of combination adjuvant consisting of DDO and MF59 showing the presence of multilamellar vesicle structures containing dye labeled DDO MRNA. Scalebar=20 micrometers.

Six-weeks old B129 mice were injected intramuscularly in the flank with 1 µg DVG-derived RNA alone or diluted in PBS mixed with MF59, (AddaVAX; InvivoGen) or MF59 alone. As vehicle control, the same volume of PBS was injected in the opposite flank. Flank muscle was collected 24 hours after injection. Total RNA was extracted from tissue homogenate with TRIzol (Invitrogen). Expression of various antiviral genes mRNA in tissue homogenate was analyzed by RT-qPCR. FIG. 23 demonstrated that MF59 and DVGs together synergize in their adjuvant capacity. FIG. 24 demonstrated the innate immune response is mice was synergistically stimulated.

Example 11: DVG-Derived RNA Induced Strong Protection to Infection Challenge

Figure 25:
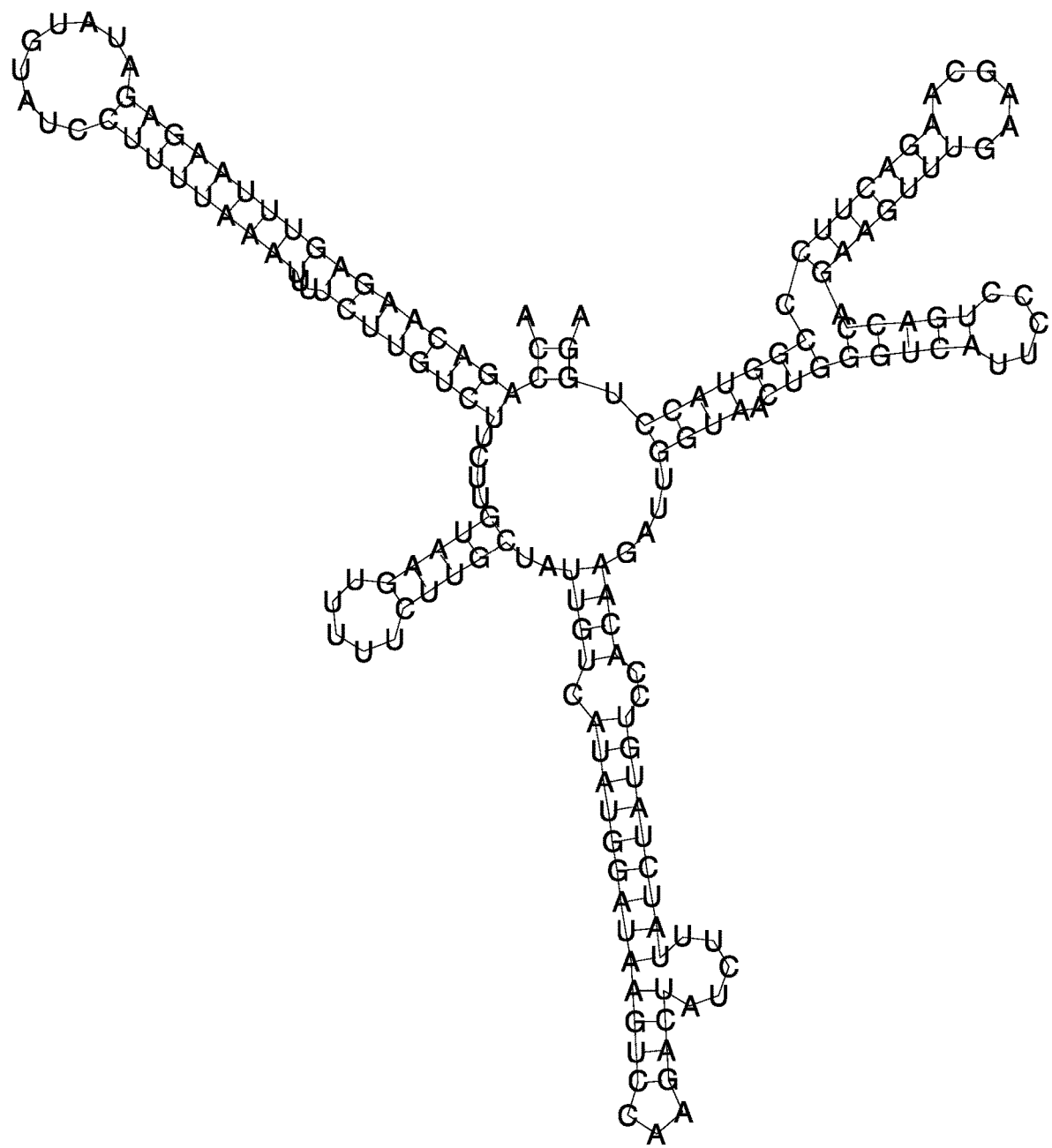
FIG. 25. DVG-268 induced strong protection to infectious challenge with single immunization. Flu HA specific IgG, IgG1 and IgG2b antibodies in the blood were measured by ELISA. *<0.0001 and *<0.001 by One way-ANOVA with Bonferroni pos-hoc test. Ns=non-significant.
Figure 25:
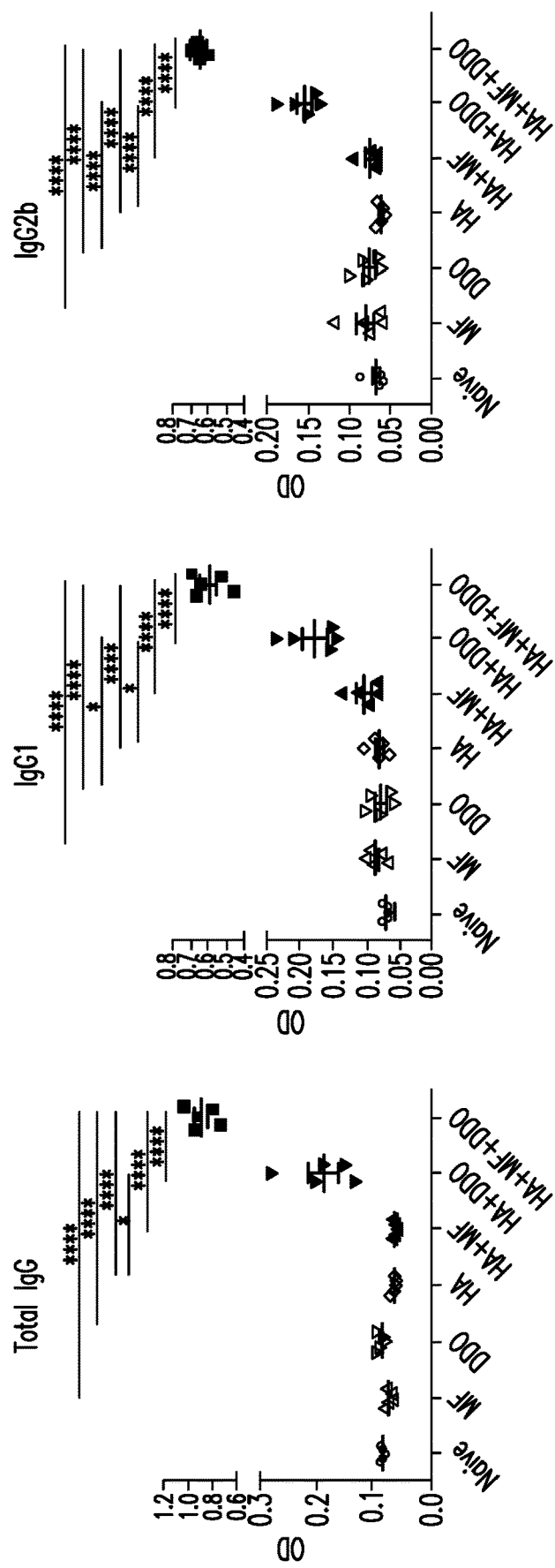
Figure 26:
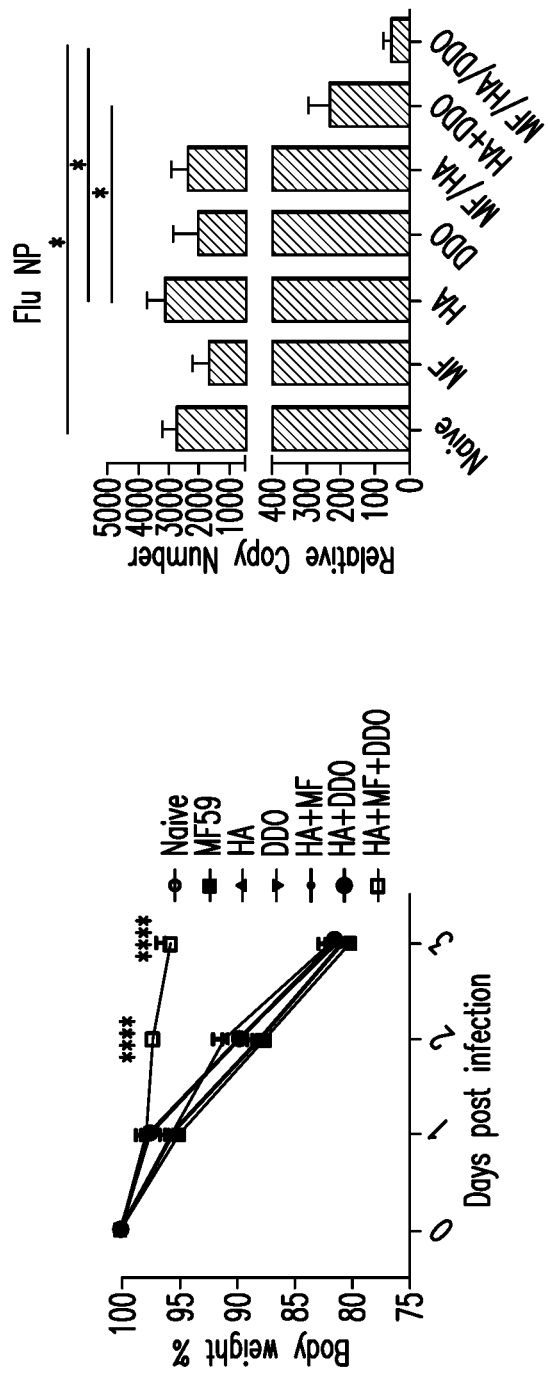
FIG. 26. DVG-268 induced strong protection to infectious challenge with single immunization. Expression of Flu NP mRNA in whole lung homogenate was analyzed by RT-qPCR as an indication of virus load in the lung. Data are shown as mRNA copy number relative to house keeping gene Rps11 and Gapdh. ***<0.001 by One way-ANOVA with Bonferroni pos-hoc test.
Figure 29:
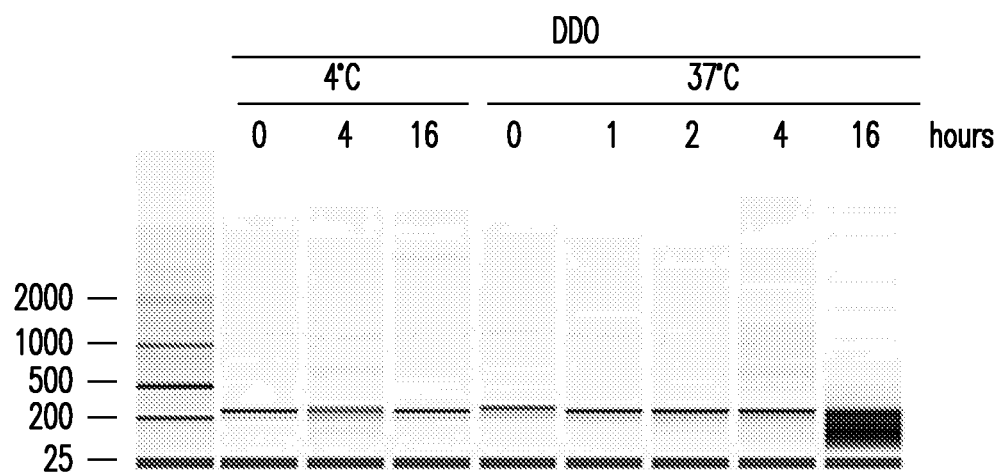
FIG. 29. DVG-derived RNA is stable at 4° C. and 37° C. RNA pico 6000 assay on Agilent 2100 Bioanalyzer.
Figure 30:
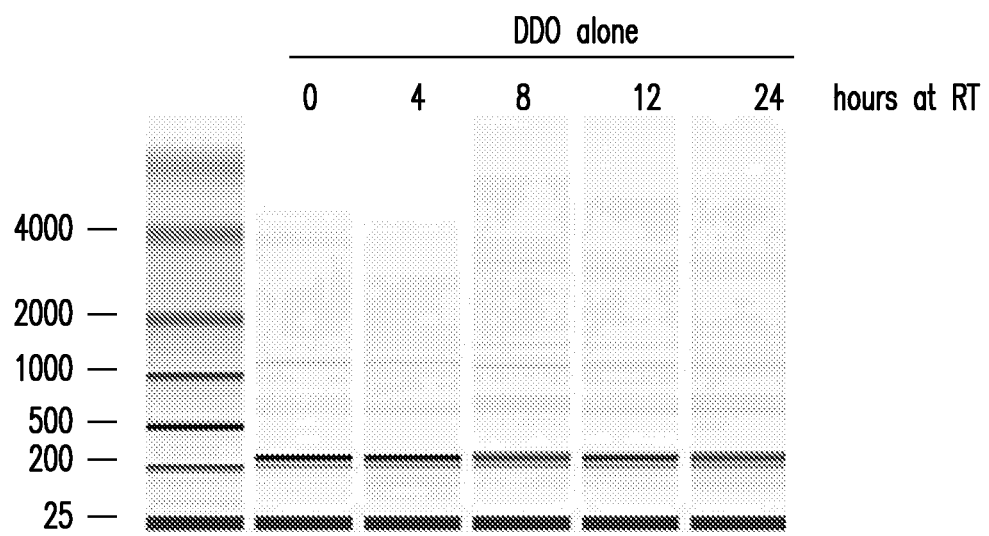
FIG. 30. DVG-derived RNA is stable at 37° C. for at least 24 hours. RNA pico 6000 assay on Agilent 2100 Bioanalyzer.
Figure 33:
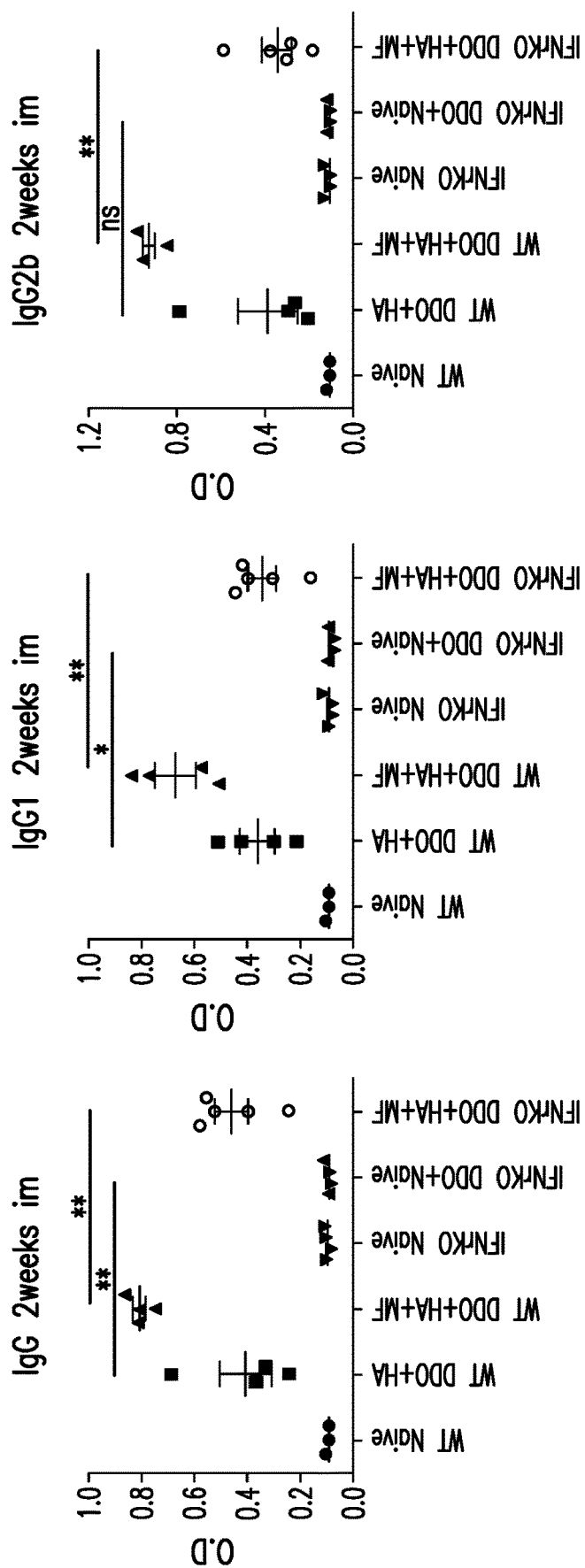
FIG. 33. Potent immunostimulatory activity of DVG-268 in vivo requires type I IFN signaling. Blood serum was collected 2 weeks post immunization. Level of IAV HA specific IgG, IgG1 and IgG2b antibody in blood serum was measured by ELISA assay. *<0.0001, <0.001 and *<0.05 by One way-ANOVA with Bonferroni pos-hoc test. ns=non-significant

In FIG. 25 six-weeks old B129 mice (n=5) were immunized intramuscularly with 1 µg DVG-268 RNA diluted in water mixed with 40 µl MF59 (InvivoGen), Flu Cal/09 D225G HA protein (HA=2.5 µg; BEI Resource). Blood serum was collected 3 weeks post immunization. Flu HA specific IgG, IgG1 and IgG2b antibodies in the blood were measured by ELISA. DVG-268 induced strong protection to infectious challenge when used in a single immunization together with an influenza HA protein vaccine. DVG-268 also acted synergistically with MF59 to create the enhanced immune response.

Twenty-seven days post immunization, mice were challenged with Flu Cal/09 D225G intranasally (2×104 TCID50/mice) and weighted in the following three consecutive days post infection. Whole lungs were collected 3 days post infection. Total RNA was extracted from the whole lung homogenate with TRIzol (Invitrogen). Expression of Flu NP mRNA in whole lung homogenate was analyzed by RT-qPCR as an indication of virus load in the lung and presented in FIG. 26. DVG-268 also acted synergistically with MF59 to create the enhanced immune response.

Example 12: Motif 70-114 Induced Strong Protection to Infection Challenge

In FIG. 27 six-weeks old B129 mice (n=5) were immunized intramuscularly with 1 μg modified $DVG_{70\text{-}114}$ 5' and 3' overhang motif (Motif; DVG$_{70-114}$ (RNA structure shown; SEQ ID NO. 23) diluted in water and mixed with 40 µl MF59 (InvivoGen) and Flu Cal/09 D225G HA protein (HA=2.5 µg; BEI Resource). Blood serum was collected 3 weeks post immunization. Level of Flu HA specific IgG, IgG1 and IgG2b antibodies in the serum were measured by ELISA. DVG$_{70-114}$ 5' and 3' overhang motif also acted synergistically with MF59 to create the enhanced immune response.

In FIG. 28 twenty-seven days post immunization, mice were challenged with Flu Cal/09 D225G intranasally (2×104 TCID50/mice) and weighted in the following three consecutive days post infection. Whole lungs were collected 3 days post infection. Total RNA was extracted from whole lung homogenate with TRIzol (Invitrogen). Expression of Flu NP mRNA in whole lung homogenate was analyzed by RT-qPCR. Data are shown as mRNA copy number relative to house keeping gene Rps11 and Gapdh. $DVG_{70-114}$ motif also acted synergistically with MF59 to create the enhanced immune response.

Example 13: DVG-Derived RNA is Stable at Room Temperature

DVG-268 is stable at 4° C. and 37° C. (FIG. 29), and continue to remain stable for at least 25 hours at room temperature (FIG. 30). DVG-268 (3 ng/µl) was diluted in water and analyzed for at the indicated times using the RNA pico 6000 assay on Agilent 2100 Bioanalyzer.

Example 14: DVG-Derived RNA can be Inserted into a Delivery Vector/DNA Vaccine to Enhance the Vaccine Immunostimulatory Activity For this study, DVG-324 was genetically engineered into a MERS DNA vaccine. A description of the MERS vaccine backbone can be found in *Science Trans Med* 301, 301ra312 (2015). The DNA vector encoding for the MERS S protein and DVG-324 was diluted in water and delivered via in vivo electroporation into the tibialis anterior muscle immunizations as indicated in FIG. 31.

DVG-324 increased the immunostimulatory activity of the MERS vaccine (FIG. 31). The MERS specific IFNgamma response was assessed on week three by ELISpot assays using six peptide pools encompassing the entire MERS S protein.

Example 15: $DVG_{70-114}$ Motif Alone Conserve Strong Immunostimulatory Activity in the Presence of a 5' Overhang For this study, Motif $DVG_{70-114}$ was modified by including 3' and/or 5' additional overhang nucleotides to test the minimal requirements for potent immunostimulatory activity. Recombinant $DVG_{70-114}$ was synthetized with various combination of 3' and 5' overhangs. In particular, a range of 5-15 nucleotide additional overhangs on both 5' and 3' prime of $DVG_{70-114}$ motif were tested.

LLC-MK2 cells were transfected with 250 ng of control or treated RNAs and analyzed 6h after transfection by RT-qPCR. Gene expression is shown as a copy number relative to the gene GAPDH. Error bars indicate the standard deviation of triplicate measurements in a representative experiment (p<0.01, *p<0.001, ****p<0.0001) by one way ANOVA with Bonferroni adjustment performed on PRISM. All treatments were run in triplicate.

3'-overhang consisted of an additional 10 nucleotide overhang sequence at 3' prime of $DVG_{70-114}$ motif (SEQ ID NO.: 22). 5' and 3'-overhang consisted of additional 5 nucleotides and 15 nucleotides at the 5' prime and 3' prime of $DVG_{70-114}$ motif (SEQ ID NO.: 23), respectively. Blunt consisted of $DVG_{70-114}$ motif alone (SEQ ID NO.: 1). Mock was the untreated control.

The data indicate an overhang at the 5' end was required for maximized IFN stimulation (FIG. 32). These mutant RNAs were then transfected into cells and innate immune responses were characterized using qPCR. Consistent with the previous experiment, the molecule with the motif placed at the 3' end failed to trigger an immune response. In addition, the blunt motif, lacking both a 5' and 3' overhangs, also failed to trigger an immune response. However, the mutant RNA with the motif flanked by overhangs at both the 3' and 5' successfully elicited an immune response comparable to the parent DVG-268 molecule.

Example 16: Potent Immunostimulatory Activity of DDO In Vivo Requires Type I IFN Signaling Six-weeks old WT and IFNb receptor knockout (IFNrKO) mice were immunized intramuscularly with 1 µg DVG-derived RNA (DVG-268) diluted in water mixing with 40 µl MF59 (MF; InvivoGen) and 0.625 µg IAV Cal/09 D225G HA protein (HA; BEI Resource). Blood serum was collected 2 weeks post immunization. Level of IAV HA specific IgG, IgG1 and IgG2b antibody in blood serum was measured by ELISA assay. *<0.0001, <0.001 and *<0.05 by One way-ANOVA with Bonferroni pos-hoc test. ns=non-significant Result show IFN dependency of DVG-268 working as an adjuvant in vivo (FIG. 33).

Various publications, patents and patent application are cited herein, the contents of which are hereby incorporated by reference in their entireties.

REFERENCES

1. Dixit E, Kagan J C. 2013. Intracellular pathogen detection by RIG-I-like receptors. Advances in immunology 117: 99-125.
2. Kumar H, Kawai T, Akira S. 2011. Pathogen recognition by the innate immune system. International reviews of immunology 30:16-34.
3. Yoo J S, Kato H, Fujita T. 2014. Sensing viral invasion by RIG-I like receptors. Current opinion in microbiology 20:131-138.
4. Seth R B, Sun L, Ea C K, Chen Z J. 2005. Identification and characterization of MAVS, a mitochondrial antiviral signaling protein that activates NF-kappaB and IRF 3. Cell 122:669-682.
5. Kawai T, Takahashi K, Sato S, Coban C, Kumar H, Kato H, Ishii K J, Takeuchi O, Akira S. 2005. IPS-1, an adaptor triggering RIG-I- and Mda5-mediated type I interferon induction. Nat Immunol 6:981-988.
6. Xu L G, Wang Y Y, Han K J, Li L Y, Zhai Z, Shu H B. 2005. VISA is an adapter protein required for virus-triggered IFN-beta signaling. Mol Cell 19:727-740.
7. Samuel C E. 2001. Antiviral actions of interferons. Clinical microbiology reviews 14:778-809.
8. Schlee M, Roth A, Hornung V, Hagmann C A, Wimmenauer V, Barchet W, Coch C, Janke M, Mihailovic A, Wardle G, Juranek S, Kato H, Kawai T, Poeck H, Fitzgerald K A, Takeuchi O, Akira S, Tuschl T, Latz E, Ludwig J, Hartmann G. 2009. Recognition of 5' triphosphate by 9. Yoneyama M, Onomoto K, Jogi M, Akaboshi T, Fujita T. 2015. Viral RNA detection by RIG-I-like receptors. Curr Opin Immunol 32C:48-53.
10. Anchisi S p, Guerra J, Garcin D. 2015. RIG-I ATPase Activity and Discrimination of Self-RNA versus Non-Self-RNA. mBio 6 (2) pii: e12349-14.
11. Nallagatla S R, Hwang J, Toroney R, Zheng X, Cameron C E, Bevilacqua P C. 2007. 5'-triphosphate-dependent activation of PKR by RNAs with short stem-loops. Science 318:1455-1458.
12. Strahle L, Garcin D, Kolakofsky D. 2006. Sendai virus defective-interfering genomes and the activation of interferon-beta. Virology 351:101-111.
13. Saito T, Owen D M, Jiang F, Marcotrigiano J, Gale M, Jr. 2008. Innate immunity induced by composition-dependent RIG-I recognition of hepatitis C virus RNA. Nature 454:523-527.
14. Schnell G, Loo Y M, Marcotrigiano J, Gale M, Jr. 2012. Uridine composition of the poly-U/UC tract of HCV RNA defines non-self recognition by RIG-I. PLoS pathogens 8:e1002839.
15. Uzri D, Gehrke L. 2009. Nucleotide sequences and modifications that determine RIG-I/RNA binding and signaling activities. J Virol 83:4174-4184.
16. Witteveldt J, Blundell R, Maarleveld J J, McFadden N, Evans D J, Simmonds P. 2013. The influence of viral RNA secondary structure on interactions with innate host cell defences. Nucleic Acids Research 42 (5): 3314-29.
17. Goubau D, Schlee M, Deddouche S, Pruijssers A J, Zillinger T, Goldeck M, Schuberth C, Van der Veen A G, Fujimura T, Rehwinkel J, Iskarpatyoti J A, Barchet W, Ludwig J, Dermody T S, Hartmann G, Reis e Sousa C. 2014. Antiviral immunity via RIG-I-mediated recognition of RNA bearing 5'-diphosphates. Nature 514:372-375.
18. Pichlmair A, Schulz O, Tan C-P, Rehwinkel J, Kato H, Takeuchi O, Akira S, Way M, Schiavo G, Reis e Sousa C. 2009. Activation of MIDAS Requires Higher-Order RNA Structures Generated during Virus Infection. Journal of virology 83:10761-10769.
19. Kato H, Takeuchi O, Sato S, Yoneyama M, Yamamoto M, Matsui K, Uematsu S, Jung A, Kawai T, Ishii K J, Yamaguchi O, Otsu K, Tsujimura T, Koh C S, Reis e Sousa C, Matsuura Y, Fujita T, Akira S. 2006. Differential roles of MIDAS and RIG-I helicases in the recognition of RNA viruses. Nature 441:101-105.
20. Moltedo B, Lopez C B, Pazos M, Becker M I, Hermesh T, Moran T M. 2009. Cutting edge: stealth influenza virus replication precedes the initiation of adaptive immunity. J Immunol 183:3569-3573.
21. Zhao L, Jha B K, Wu A, Elliott R, Ziebuhr J, Gorbalenya A E, Silverman R H, Weiss S R. 2012. Antagonism of the interferon-induced OAS-RNase L pathway by murine coronavirus ns2 protein is required for virus replication and liver pathology. Cell Host Microbe 11:607-616.
22. Hermesh T, Moltedo B, Lopez C B, Moran T M. 2010. Buying time—the immune system determinants of the incubation period to respiratory viruses. Viruses 2:2541-2558.
23. Lopez C B. 2014. Defective viral genomes: critical danger signals of viral infections. Journal of virology 88:8720-8723.
24. Tapia K, Kim W K, Sun Y, Mercado-Lopez X, Dunay E, Wise M, Adu M, Lopez C B. 2013. Defective viral genomes arising in vivo provide critical danger signals for the triggering of lung antiviral immunity. PLoS Pathog 9:e1003703.
25. Yount J S, Kraus T A, Horvath C M, Moran T M, Lopez C B. 2006. A novel role for viral-defective interfering particles in enhancing dendritic cell maturation. J Immunol 177:4503-4513.
26. Mercado-Lopez X, Cotter C R, Kim W K, Sun Y, Munoz L, Tapia K, Lopez C B. 2013. Highly immunostimulatory RNA derived from a Sendai virus defective viral genome. Vaccine 31:5713-5721.
27. Tapia K, Kim W K, Sun Y, Mercado-Lopez X, Dunay E, Wise M, Adu M, Lopez C B. 2013. Defective viral genomes arising in vivo provide critical danger signals for the triggering of lung antiviral immunity. PLoS pathogens 9:e1003703.
28. Re G G, Gupta K C, Kingsbury D W. 1983. Genomic and copy-back 3' termini in Sendai virus defective interfering RNA species. Journal of virology 45:659-664.
29. Calain P, Curran J, Kolakofsky D, Roux L. 1992. Molecular cloning of natural paramyxovirus copy-back defective interfering RNAs and their expression from DNA. Virology 191:62-71.
30. Engelhorn M, Stricker R, Roux L. 1993. Molecular cloning and characterization of a Sendai virus internal deletion defective RNA. J Gen Virol 74 (Pt 1):137-141.
31. Kolakofsky D. 1976. Isolation and characterization of Sendai virus DI-RNAs. Cell 8:547-555.
32. Salinas Y, Roux L. 2005. Replication and packaging properties of short Paramyxovirus defective RNAs. Virus Res 109:125-132.
33. Strahle L, Marq J B, Brini A, Hausmann S, Kolakofsky D, Garcin D. 2007. Activation of the beta interferon promoter by unnatural Sendai virus infection requires RIG-I and is inhibited by viral C proteins. J Virol 81:12227-12237.
34. Yount J S, Gitlin L, Moran T M, Lopez C B. 2008. MDA5 Participates in the Detection of Paramyxovirus Infection and Is Essential for the Early Activation of Dendritic Cells in Response to Sendai Virus Defective Interfering Particles. J Immunol 180:4910-4918.
35. Patel J R, Jain A, Chou Y Y, Baum A, Ha T, Garcia-Sastre A. 2013. ATPase-driven oligomerization of RIG-I on RNA allows optimal activation of type-I interferon. EMBO Rep 14:780-787.
36. Wu B, Peisley A, Tetrault D, Li Z, Egelman E H, Magor K E, Walz T, Penczek P A, Hur S. 2014. Molecular Imprinting as a Signal-Activation Mechanism of the Viral RNA Sensor RIG-I. Molecular Cell 55:511-523.
37. Peisley A, Lin C, Wu B, Orme-Johnson M, Liu M, Walz T, Hur S. 2011. Cooperative assembly and dynamic disassembly of MDA5 filaments for viral dsRNA recognition. Proc Natl Acad Sci USA 108:21010-21015.
38. Peisley A, Wu B, Yao H, Walz T, Hur S. 2013. RIG-I forms signaling-competent filaments in an ATP-dependent, ubiquitin-independent manner. Mol Cell 51:573-583.
39. Wu B, Peisley A, Richards C, Yao H, Zeng X, Lin C, Chu F, Walz T, Hur S. 2013. Structural basis for dsRNA recognition, filament formation, and antiviral signal activation by MDA5. Cell 152:276-289.
40. Pichlmair A, Schulz O, Tan C P, Naslund T I, Liljestrom P, Weber F, Reis e Sousa C. 2006. RIG-I-mediated antiviral responses to single-stranded RNA bearing 5'-phosphates. Science 314:997-1001.
41. Weber F, Wagner V, Rasmussen S B, Hartmann R, Paludan S R. 2006. Double-stranded RNA is produced by positive-strand RNA viruses and DNA viruses but not in detectable amounts by negative-strand RNA viruses. J Virol 80:5059-5064.
42. Schonborn J, Oberstrass J, Breyel E, Tittgen J, Schumacher J, Lukacs N. 1991. Monoclonal antibodies to double-stranded RNA as probes of RNA structure in crude nucleic acid extracts. Nucleic Acids Res 19:2993-3000.
43. Shioda T, Iwasaki K, Shibuta H. 1986. Determination of the complete nucleotide sequence of the Sendai virus genome RNA and the predicted amino acid sequences of the F, HN and L proteins. Nucleic Acids Res 14:1545-1563.
44. Plattet P, Strahle L, le Mercier P, Hausmann S p, Garcin D, Kolakofsky D. 2007. Sendai virus RNA polymerase scanning for mRNA start sites at gene junctions. Virology 362:411-420.
45. Gosai S J, Foley S W, Wang D, Silverman I M, Selamoglu N, Nelson A D, Beilstein M A, Daldal F, Deal R B, Gregory B D. 2015. Global Analysis of the RNA-Protein Interaction and RNA Secondary Structure Landscapes of the *Arabidopsis* Nucleus. Mol Cell 57:376-388.
46. Deutsch V, Brun G. 1983. Nongenetic complementation in VSV: asymmetric contribution of the L proteins of each parent in the rescue of group I ts mutants. Virology 124:366-379.
47. Raj A, van den Bogaard P, Rifkin S A, van Oudenaarden A, Tyagi S. 2008. Imaging individual mRNA molecules using multiple singly labeled probes. Nat Meth 5:877-879.
48. Zavada J, Zavadova Z, Russ G, Polakova K, Rajcani J, Stencl J, Loksa J. 1983. Human cell surface proteins selectively assembled into vesicular stomatitis virus virions. Virology 127:345-360.
49. Peluso R W, Moyer S A. 1983. Initiation and replication of vesicular stomatitis virus genome RNA in a cell-free system. Proceedings of the National Academy of Sciences of the United States of America 80:3198-3202.

What is claimed is:

1. An isolated RNA molecule comprising the nucleotide sequence set forth in SEQ ID NO:1, SEQ ID NO:2, SEQ ID NO:5, or SEQ ID NO:23.

2. The isolated RNA molecule of claim 1 comprising the nucleotide sequence set forth in SEQ ID NO: 1, wherein 5-15 nucleotides are added to the 5' end of the nucleotide sequence.

3. The isolated RNA molecule of claim 2, wherein 5-15 nucleotides are added to the 3' end of the nucleotide sequence.

4. A pharmaceutical composition comprising:
the isolated RNA molecule of claim 1; and
a pharmaceutically acceptable carrier.

5. The pharmaceutical composition of claim 4, further comprising an adjuvant.

6. The pharmaceutical composition of claim 4 further comprising one or more antigens.

7. The pharmaceutical composition of claim 6, wherein the one or more antigens are selected from the group consisting of virus, bacterial, fungal, parasite, nucleotide, polysaccharides, lipids, tumor antigens, allergens, and peptide antigens.

8. The isolated RNA molecule of claim 1, wherein the isolated RNA molecule has immunostimulatory activity.

* * * * *